(12) United States Patent
Moon et al.

(10) Patent No.: US 8,680,113 B2
(45) Date of Patent: Mar. 25, 2014

(54) BMI-1 PROTEIN EXPRESSION MODULATORS

(75) Inventors: Young-Choon Moon, Belle Mead, NJ (US); Nadiya Sydorenko, Piscataway, NJ (US); Thomas Davis, South Orange, NJ (US); Liangxian Cao, Parlin, NJ (US); Daniel J. Medina, Hampton, NJ (US); Marites A. Rafanan, Belle Mead, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 490 days.

(21) Appl. No.: 13/000,711

(22) PCT Filed: Jul. 1, 2009

(86) PCT No.: PCT/US2009/049395
§ 371 (c)(1),
(2), (4) Date: Apr. 1, 2011

(87) PCT Pub. No.: WO2010/002985
PCT Pub. Date: Jan. 7, 2010

(65) Prior Publication Data
US 2011/0190239 A1      Aug. 4, 2011

Related U.S. Application Data

(60) Provisional application No. 61/077,367, filed on Jul. 1, 2008.

(51) Int. Cl.
| | | |
|---|---|---|
| *A61K 31/655* | (2006.01) | |
| *A61K 31/44* | (2006.01) | |
| *A61K 31/519* | (2006.01) | |
| *A61K 31/505* | (2006.01) | |
| *C07D 487/14* | (2006.01) | |
| *C07D 401/14* | (2006.01) | |
| *C07D 491/04* | (2006.01) | |

(52) U.S. Cl.
USPC ........ 514/300; 514/150; 514/259.1; 514/275; 544/281; 544/331; 546/121

(58) Field of Classification Search
USPC ............... 514/275, 259.1, 150, 300; 544/331, 544/281; 546/121
See application file for complete search history.

(56) References Cited

U.S. PATENT DOCUMENTS

| 7,084,159 B2 | 8/2006 | Cao et al. |
| 2007/0004711 A1 | 1/2007 | Zhang et al. |
| 2007/0184979 A1 | 8/2007 | Maier et al. |

FOREIGN PATENT DOCUMENTS

| WO | 01/14375 A1 | 3/2001 |
| WO | 01/64674 A1 | 9/2001 |
| WO | 02/066480 A2 | 8/2002 |
| WO | 02/066481 A1 | 8/2002 |
| WO | 03/015773 A2 | 2/2003 |
| WO | 2009/023402 A2 | 2/2009 |

OTHER PUBLICATIONS

Kate F Byth et al.: "Imidazo[1,2-a]pyridines. Part 2: SAR and optimisation of a potent and selective class of cyclin-dependent kinase inhibitors," Bioorganic & Medicinal Chemistry Letters, Pergamon, (2004) pp. 2245-2248, 14:9, Elsevier Science, Great Britain.
Extended European Search Report EP 09774435.3, mailed Nov. 22, 2011.
International Search Report for PCT/US2009/049395, dated Sep. 16, 2009.
Written Opinion for PCT/US2009/049395, dated Sep. 16, 2009.

*Primary Examiner* — James O Wilson
*Assistant Examiner* — Ebenezer O Sackey
(74) *Attorney, Agent, or Firm* — Hoffmann & Baron, LLP

(57) ABSTRACT

Compounds having Formula I:

Compounds having Formula I:

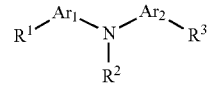

wherein the variables $Ar_1$, $Ar_2$, $R^1$, $R^2$ and $R^3$ are defined herein, pharmaceutical compositions, and methods of using such compounds or compositions for inhibiting Bmi-1 expression.

16 Claims, 2 Drawing Sheets

BMI-1 PROTEIN EXPRESSION MODULATORS

CROSS-REFERENCE TO RELATED APPLICATIONS

This application is the National Stage of International Application No. PCT/US09/49395, filed Jul. 1, 2009 which claims the benefit of U.S. Provisional Application 61/077,367, filed Jul. 1, 2008, the contents of which are incorporated by reference herein.

Compounds, pharmaceutical compositions, and methods of using such compounds or compositions thereof for treating a disease modulated by B-cell specific Moloney murine leukemia virus integration site 1 (Bmi-1) protein expression are described. The compounds or compositions and methods of using such compounds or compositions are useful for treating cancer by down-regulating Bmi-1 protein expression.

BACKGROUND

The Bmi-1 gene was originally identified by its over-expression in various lymphomas. Subsequently, Bmi-1 has been shown to have oncogenic activity when over-expressed in normal cells and to play a role in maintenance of adult stem cell populations (asymmetric cell division). The Bmi-1 protein is elevated in many tumor types and is particularly important in hematologic cancers and brain cancers. Experimental reduction of Bmi-1 protein levels by siRNA causes apoptosis and/or cell senescence in tumor cells in vitro and increases their susceptibility to cytotoxic agents such as 5-fluorouracil. The Bmi-1 protein has no enzymatic activity, but serves as the key regulatory component of the PRC1 complex (polycomb repressive complex-1). As a nonenzymatic but key regulatory member of the PRC1 complex, targeting Bmi-1 by traditional drug discovery methods is problematic. Bmi-1 protein levels are tightly regulated within cells through both transcriptional and post-transcriptional mechanisms.

Accordingly, there still remains a need for anticancer drugs that effect tumor regulatory mechanisms with reduced side effects.

SUMMARY

Certain compounds and to their use in modulating Bmi-1 protein production and methods for treating diseases modulated by the Bmi-1 protein are described. The applicants have discovered that Bmi-1 protein production is highly regulated by elements found within the 5' and 3'UTRs of the Bmi-1 gene and Bmi-1 mRNA. Accordingly, compounds that target any of the 5'-UTR and 3'-UTR, or the 5'-UTR or the 3'-UTR of Bmi-1 mRNA and modulate post-transcriptional expression of Bmi-1 protein can be used to treat diseases mediated by Bmi-1 expression in human subjects in need thereof.

In one embodiment, compounds that target any of the 5'-UTR and 3'-UTR, or the 5'-UTR or the 3'-UTR of Bmi-1 mRNA and down-regulate post-transcriptional Bmi-1 protein expression may be be used to treat cancer and solid tumors in human subjects in need thereof.

In one embodiment is a compound of Formula (I):

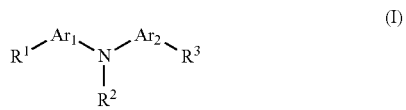

wherein $Ar_1$, $Ar_2$, $R^1$, $R^2$ and $R^3$ are as defined herein, and forms and pharmaceutical compositions thereof, and methods of using such compounds, forms or compositions thereof to treat diseases mediated by Bmi-1 expression.

In one embodiment is a compound of Formula (I) selected from a compound of Formula (Ia):

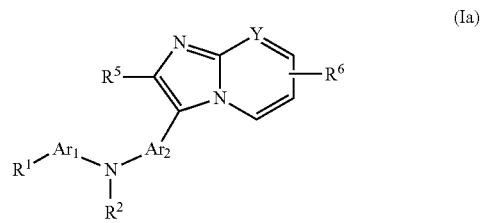

wherein $Ar_1$, $Ar_2$, $R^1$, $R^2$, $R^5$, $R^6$ and Y are as defined herein, and forms and pharmaceutical compositions thereof, and methods of using such compounds, forms or compositions thereof to treat diseases mediated by Bmi-1 expression.

In one embodiment is a compound of Formula (I) selected from a compound of Formula (Ib) or Formula (Ic):

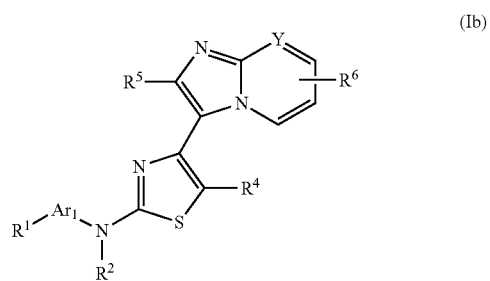

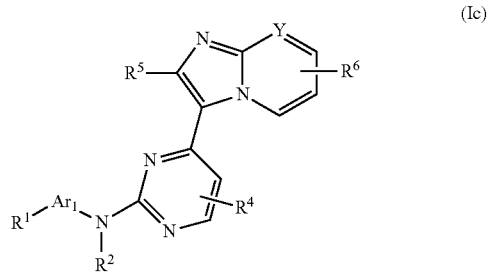

wherein $Ar_1$, $R^1$, $R^2$, $R^4$, $R^5$, $R^6$ and Y are as defined herein, and forms and pharmaceutical compositions thereof, and methods of using such compounds, forms or compositions thereof to treat diseases mediated by Bmi-1 expression.

In one embodiment is a compound of Formula (I) selected from a compound of Formula (Id), Formula (Ie), Formula (If) or Formula (Ig):

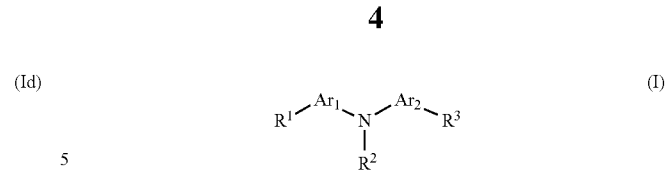

(I)

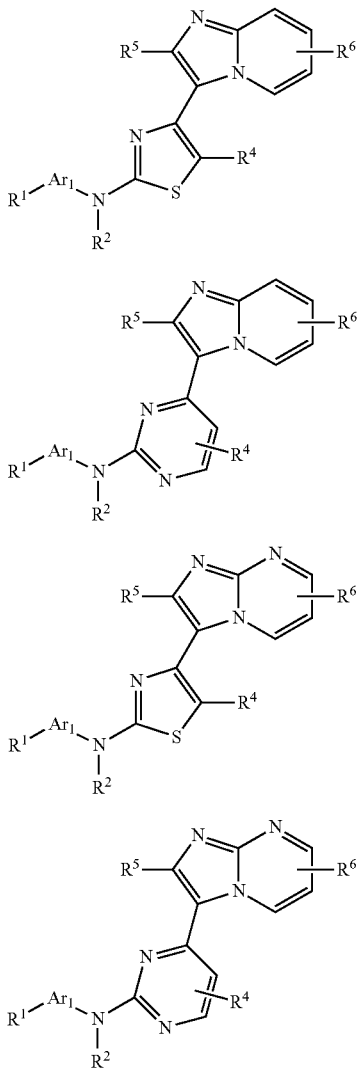

wherein Ar$_1$, R$^1$, R$^2$, R$^4$, R$^5$ and R$^6$ are as defined herein, and forms and pharmaceutical compositions thereof, and methods of using such compounds, forms or compositions thereof to treat diseases mediated by Bmi-1 expression.

DETAILED DESCRIPTION

Figure 1:
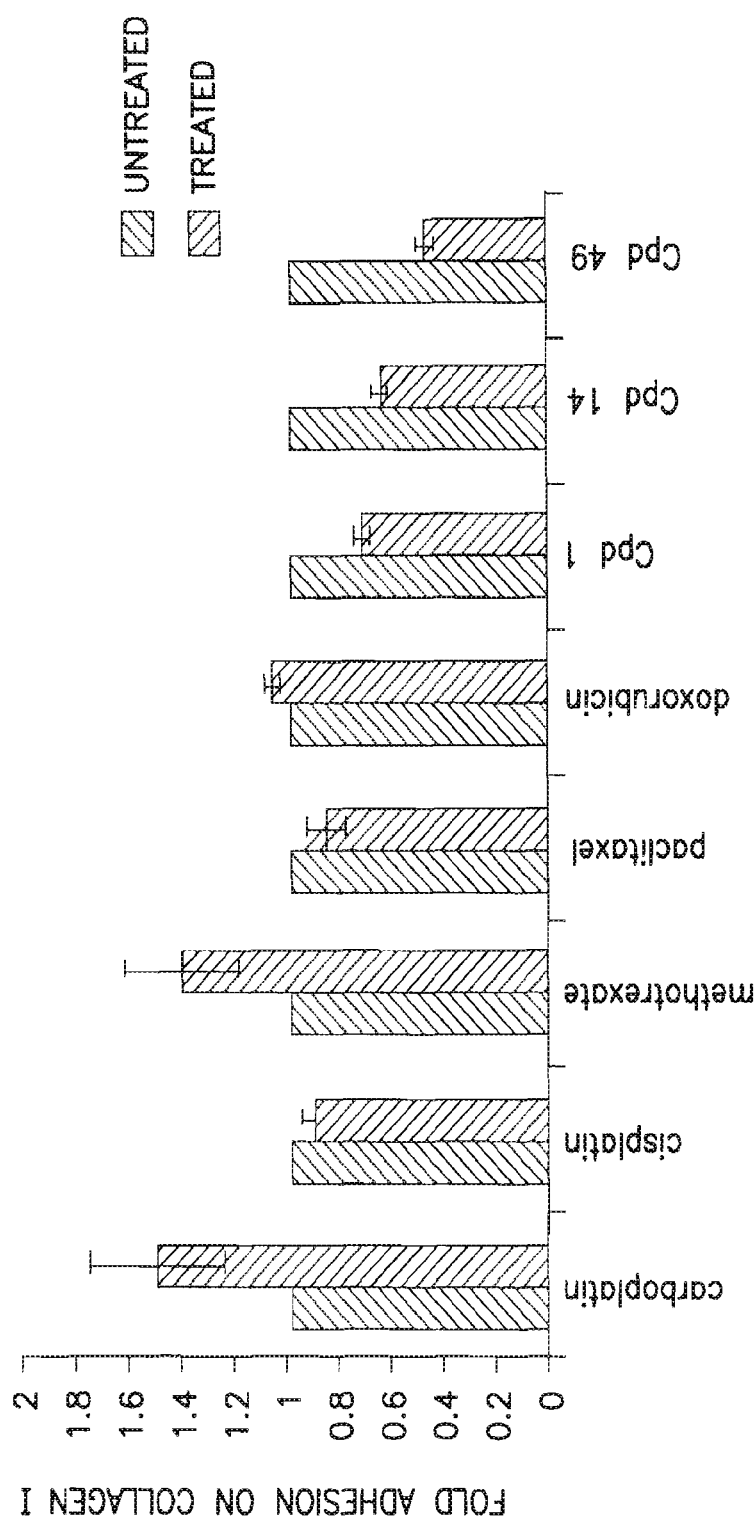
FIG. 1 shows that BMI-1 inhibitor compounds described herein demonstrated inhibition of Bmi-1 in a prostate cancer cell line.

Compounds and their use in modulating Bmi-1 protein production and methods for treating diseases modulated by the Bmi-1 protein are described.

In one embodiment is a compound of Formula (I):

and forms thereof, wherein
Ar$_1$ is phenyl or benzo[1,3]dioxolyl;
Ar$_2$ is thiazolyl or pyrimidinyl substituted with R$^4$;
R$^1$ is hydrogen or one, two, three or four substituents each selected from halogen, cyano, hydroxy, C$_{1-8}$alkyl, C$_{2-8}$alkenyl, C$_{2-8}$alkynyl, C$_{1-8}$alkoxy, halo-C$_{1-8}$alkyl, halo-C$_{1-8}$alkoxy, hydroxy-C$_{1-8}$alkyl, C$_{1-8}$alkoxy-C$_{1-8}$alkyl, C$_{1-8}$alkoxy-C$_{1-8}$alkoxy, C$_{1-8}$alkoxy-C$_{1-8}$alkoxy-C$_{1-8}$alkoxy, carboxy, amino, C$_{1-8}$alkyl-amino, amino-C$_{1-8}$alkyl, C$_{1-8}$alkyl-amino-C$_{1-8}$alkyl, C$_{1-8}$alkyl-carbonyl, C$_{1-8}$alkoxy-carbonyl, aminosulfonyl, C$_{1-8}$alkyl-aminosulfonyl, C$_{1-8}$alkyl-carbonyl-amino and C$_{1-8}$alkoxy-carbonyl-amino;
R$^2$ is hydrogen or C$_{1-8}$-alkyl;
R$^3$ is imidazo[1,2-a]pyridin-3-yl or imidazo[1,2-a]pyrimidin-3-yl each substituted with R$^5$ and R$^6$;
R$^4$ and R$^5$ are each hydrogen, C$_{1-8}$alkyl or halo-C$_{1-8}$alkyl; and
R$^6$ is hydrogen or one, two, three or four substituents each selected from halogen, hydroxy or C$_{1-8}$alkyl; with the proviso that the compound of Formula (I) is other than:
N-(2,6-dibromo-4-methoxyphenyl)-4-(2-methylimidazo[1,2-a]pyrimidin-3-yl)thiazol-2-amine,
N-(3-chloro-2-methylphenyl)-4-(2-methylimidazo[1,2-a]pyrimidin-3-yl)thiazol-2-amine,
N-(2,5-dimethoxyphenyl)-4-(2-methylimidazo[1,2-a]pyrimidin-3-yl)thiazol-2-amine,
N-(2-ethoxyphenyl)-4-(2-methylimidazo[1,2-a]pyrimidin-3-yl)thiazol-2-amine,
N-(2-chlorophenyl)-4-(2-methylimidazo[1,2-a]pyrimidin-3-yl)thiazol-2-amine,
4-(2-methylimidazo[1,2-a]pyrimidin-3-yl)-N-m-tolylthiazol-2-amine,
N,N-diethyl-N'-(4-(2-methylimidazo[1,2-a]pyrimidin-3-yl)thiazol-2-yl)benzene-1,4-diamine,
N-(2-methoxyphenyl)-4-(2-methylimidazo[1,2-a]pyrimidin-3-yl)thiazol-2-amine,
1-(3-(4-(2-methylimidazo[1,2-a]pyrimidin-3-yl)thiazol-2-ylamino)phenyl)ethanone,
4-(4-(2-methylimidazo[1,2-a]pyrimidin-3-yl)thiazol-2-ylamino)benzenesulfonamide,
N-(4-(4-(2-methylimidazo[1,2-a]pyrimidin-3-yl)thiazol-2-ylamino)phenyl)acetamide,
N,N-dimethyl-N'-(4-(2-methylimidazo[1,2-a]pyrimidin-3-yl)thiazol-2-yl)benzene-1,4-diamine,
N-(4-ethoxyphenyl)-4-(2-methylimidazo[1,2-a]pyrimidin-3-yl)thiazol-2-amine,
N-(4-methoxyphenyl)-4-(2-methylimidazo[1,2-a]pyrimidin-3-yl)thiazol-2-amine,
4-(4-(2-methylimidazo[1,2-a]pyrimidin-3-yl)thiazol-2-ylamino)benzoic acid,
4-(4-(2,7-dimethylimidazo[1,2-a]pyridin-3-yl)thiazol-2-ylamino)phenol,
4-(2,7-dimethylimidazo[1,2-a]pyridin-3-yl)-N-(4-methoxyphenyl)thiazol-2-amine, and
4-(2,7-dimethylimidazo[1,2-a]pyridin-3-yl)-N-(2-methoxyphenyl)thiazol-2-amine.
In another embodiment is a compound of Formula (I) wherein R$^1$ is hydrogen or one, two, three or four substituents each selected from halogen, hydroxy, C$_{1-8}$alkyl, C$_{1-8}$alkoxy, $C_{1-8}$alkoxy-$C_{1-8}$alkoxy, carboxy, $C_{1-8}$alkyl-amino, $C_{1-8}$alkyl-carbonyl, aminosulfonyl or $C_{1-8}$alkyl-carbonyl-amino.

In another embodiment is a compound of Formula (I) wherein $R^1$ is hydrogen or one, two or three substituents each selected from chloro, fluoro, bromo, iodo, hydroxy, methyl, ethyl, isopropyl, tert-butyl, methoxy, ethoxy, methoxyethoxy, carboxy, dimethyl-amino, diethyl-amino, methyl-carbonyl, aminosulfonyl or methyl-carbonyl-amino.

In another embodiment is a compound of Formula (I) wherein
$R^2$ is hydrogen or methyl;
$R^4$ and $R^5$ are each hydrogen, methyl, ethyl, n-propyl or trifluoromethyl; and
$R^6$ is hydrogen or one, two, three or four substituents each selected from fluoro, chloro, bromo, hydroxy, methyl or n-propyl.

In another embodiment is a compound of Formula (I) wherein the form is selected from a free acid, free base, salt, ester, hydrate, solvate, chelate, clathrate, isotopologue, geometric isomer, stereoisomer, racemate, enantiomer, diastereomer, tautomer or polymorph thereof. In certain embodiments, the form of the compound of Formula (I) is pharmaceutically acceptable.

In another embodiment is a compound of Formula (I) or a form thereof for use in the methods and compositions provided herein.

In one embodiment is a compound of Formula (I) selected from a compound of Formula (Ia):

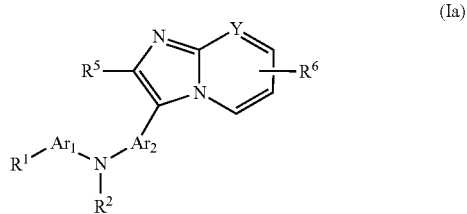

(Ia)

and forms thereof, wherein
Y is CH or N;
$Ar_1$ is phenyl or benzo[1,3]dioxolyl;
$Ar_2$ is thiazolyl or pyrimidinyl substituted with $R^4$;
$R^1$ is hydrogen or one, two, three or four substituents each selected from halogen, cyano, hydroxy, $C_{1-8}$alkyl, $C_{2-8}$alkenyl, $C_{1-8}$alkynyl, $C_{1-8}$alkoxy, halo-$C_{1-8}$alkyl, halo-$C_{1-8}$alkoxy, hydroxy-$C_{1-8}$alkyl, $C_{1-8}$alkoxy-$C_{1-8}$alkyl, $C_{1-8}$alkoxy-$C_{1-8}$alkoxy, $C_{1-8}$alkoxy-$C_{1-8}$alkoxy-$C_{1-8}$alkoxy, carboxy, amino, $C_{1-8}$alkyl-amino, amino-$C_{1-8}$alkyl, $C_{1-8}$alkyl-amino-$C_{1-8}$alkyl, $C_{1-8}$alkyl-carbonyl, $C_{1-8}$alkoxy-carbonyl, aminosulfonyl, $C_{1-8}$alkyl-aminosulfonyl, $C_{1-8}$alkyl-carbonyl-amino and $C_{1-8}$alkoxy-carbonyl-amino;
$R^2$ is hydrogen or $C_{1-8}$alkyl;
$R^4$ and $R^5$ are each hydrogen, $C_{1-8}$alkyl or halo-$C_{1-8}$alkyl; and
$R^6$ is hydrogen or one, two, three or four substituents each selected from halogen, hydroxy or $C_{1-8}$alkyl;
with the proviso that the compound of Formula (Ia) is other than:
N-(2,6-dibromo-4-methoxyphenyl)-4-(2-methylimidazo[1,2-a]pyrimidin-3-yl)thiazol-2-amine,
N-(3-chloro-2-methylphenyl)-4-(2-methylimidazo[1,2-a]pyrimidin-3-yl)thiazol-2-amine,
N-(2,5-dimethoxyphenyl)-4-(2-methylimidazo[1,2-a]pyrimidin-3-yl)thiazol-2-amine,
N-(2-ethoxyphenyl)-4-(2-methylimidazo[1,2-a]pyrimidin-3-yl)thiazol-2-amine,
N-(2-chlorophenyl)-4-(2-methylimidazo[1,2-a]pyrimidin-3-yl)thiazol-2-amine,
4-(2-methylimidazo[1,2-a]pyrimidin-3-yl)-N-m-tolylthiazol-2-amine,
N,N-diethyl-N'-(4-(2-methylimidazo[1,2-a]pyrimidin-3-yl)thiazol-2-yl)benzene-1,4-diamine,
N-(2-methoxyphenyl)-4-(2-methylimidazo[1,2-a]pyrimidin-3-yl)thiazol-2-amine,
1-(3-(4-(2-methylimidazo[1,2-a]pyrimidin-3-yl)thiazol-2-ylamino)phenyl)ethanone,
4-(4-(2-methylimidazo[1,2-a]pyrimidin-3-yl)thiazol-2-ylamino)benzenesulfonamide,
N-(4-(4-(2-methylimidazo[1,2-a]pyrimidin-3-yl)thiazol-2-ylamino)phenyl)acetamide,
N,N-dimethyl-N'-(4-(2-methylimidazo[1,2-a]pyrimidin-3-yl)thiazol-2-yl)benzene-1,4-diamine,
N-(4-ethoxyphenyl)-4-(2-methylimidazo[1,2-a]pyrimidin-3-yl)thiazol-2-amine,
N-(4-methoxyphenyl)-4-(2-methylimidazo[1,2-a]pyrimidin-3-yl)thiazol-2-amine,
4-(4-(2-methylimidazo[1,2-a]pyrimidin-3-yl)thiazol-2-ylamino)benzoic acid,
4-(4-(2,7-dimethylimidazo[1,2-a]pyridin-3-yl)thiazol-2-ylamino)phenol,
4-(2,7-dimethylimidazo[1,2-a]pyridin-3-yl)-N-(4-methoxyphenyl)thiazol-2-amine, and
4-(2,7-dimethylimidazo[1,2-a]pyridin-3-yl)-N-(2-methoxyphenyl)thiazol-2-amine.

In one embodiment is a compound of Formula (I) selected from a compound of Formula (Ib) or Formula (Ic):

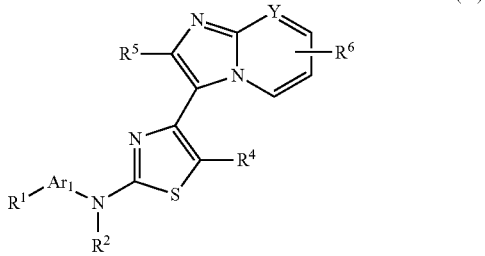

(Ib)

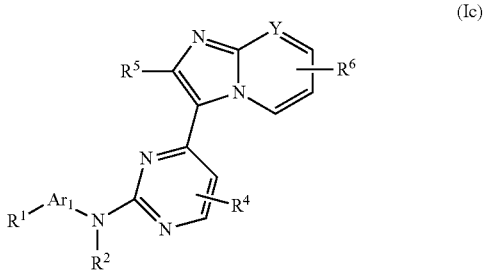

(Ic)

and forms thereof, wherein
Y is CH or N;
$Ar_1$ is phenyl or benzo[1,3]dioxolyl;
$R^1$ is hydrogen or one, two, three or four substituents each selected from halogen, cyano, hydroxy, $C_{1-8}$alkyl, $C_{2-8}$alkenyl, $C_{2-8}$alkynyl, $C_{1-8}$alkoxy, halo-$C_{1-8}$alkyl, halo-$C_{1-8}$alkoxy, hydroxy-$C_{1-8}$alkyl, $C_{1-8}$alkoxy-$C_{1-8}$alkyl, $C_{1-8}$alkoxy-$C_{1-8}$alkoxy, $C_{1-8}$alkoxy-$C_{1-8}$alkoxy-$C_{1-8}$alkoxy, carboxy, amino, $C_{1-8}$alkyl-amino, amino-$C_{1-8}$alkyl, $C_{1-8}$alkyl-carbonyl, $C_{1-8}$alkoxy-carbonyl, aminosulfonyl, $C_{1-8}$alkyl-aminosulfonyl, $C_{1-8}$alkyl-carbonyl-amino and $C_{1-8}$alkoxy-carbonyl-amino;

$R^2$ is hydrogen or $C_{1-8}$alkyl;

$R^4$ and $R^5$ are each hydrogen, $C_{1-8}$alkyl or halo-$C_{1-8}$alkyl; and $R^6$ is hydrogen or one, two, three or four substituents each selected from halogen, hydroxy or $C_{1-8}$alkyl;

with the proviso that the compound of Formula (Ib) or Formula (Ic) is other than:

N-(2,6-dibromo-4-methoxyphenyl)-4-(2-methylimidazo[1,2-a]pyrimidin-3-yl)thiazol-2-amine, N-(3-chloro-2-methylphenyl)-4-(2-methylimidazo[1,2-a]pyrimidin-3-yl)thiazol-2-amine, N-(2,5-dimethoxyphenyl)-4-(2-methylimidazo[1,2-a]pyrimidin-3-yl)thiazol-2-amine, N-(2-ethoxyphenyl)-4-(2-methylimidazo[1,2-a]pyrimidin-3-yl)thiazol-2-amine, N-(2-chlorophenyl)-4-(2-methylimidazo[1,2-a]pyrimidin-3-yl)thiazol-2-amine, 4-(2-methylimidazo[1,2-a]pyrimidin-3-yl)-N-m-tolylthiazol-2-amine, N,N-diethyl-N'-(4-(2-methylimidazo[1,2-a]pyrimidin-3-yl)thiazol-2-yl)benzene-1,4-diamine, N-(2-methoxyphenyl)-4-(2-methylimidazo[1,2-a]pyrimidin-3-yl)thiazol-2-amine, 1-(3-(4-(2-methylimidazo[1,2-a]pyrimidin-3-yl)thiazol-2-ylamino)phenyl)ethanone, 4-(4-(2-methylimidazo[1,2-a]pyrimidin-3-yl)thiazol-2-ylamino)benzenesulfonamide, N-(4-(4-(2-methylimidazo[1,2-a]pyrimidin-3-yl)thiazol-2-ylamino)phenyl)acetamide, N,N-dimethyl-N'-(4-(2-methylimidazo[1,2-a]pyrimidin-3-yl)thiazol-2-yl)benzene-1,4-diamine, N-(4-ethoxyphenyl)-4-(2-methylimidazo[1,2-a]pyrimidin-3-yl)thiazol-2-amine, N-(4-methoxyphenyl)-4-(2-methylimidazo[1,2-a]pyrimidin-3-yl)thiazol-2-amine, 4-(4-(2-methylimidazo[1,2-a]pyrimidin-3-yl)thiazol-2-ylamino)benzoic acid, 4-(4-(2,7-dimethylimidazo[1,2-a]pyridin-3-yl)thiazol-2-ylamino)phenol, 4-(2,7-dimethylimidazo[1,2-a]pyridin-3-yl)-N-(4-methoxyphenyl)thiazol-2-amine, and 4-(2,7-dimethylimidazo[1,2-a]pyridin-3-yl)-N-(2-methoxyphenyl)thiazol-2-amine.

In one embodiment is a compound of Formula (I) selected from a compound of Formula (Id), Formula (Ie), Formula (If) or Formula (Ig):

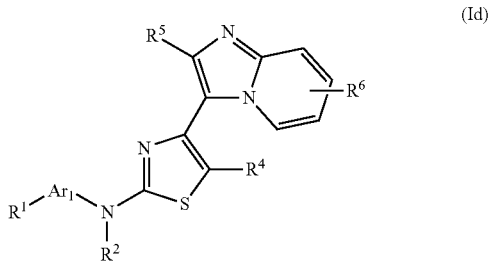
(Id)

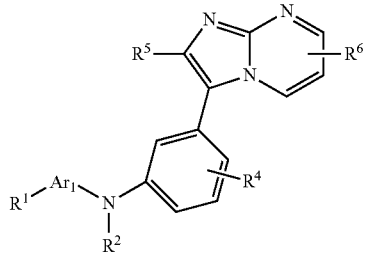
(Ie)

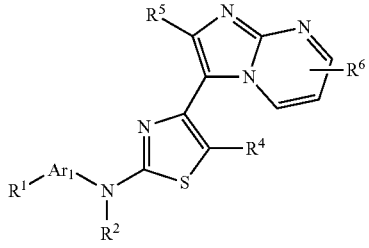
(If)

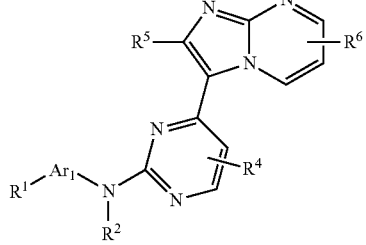
(Ig)

and forms thereof, wherein $Ar_1$ is phenyl or benzo[1,3]dioxolyl;

$R^1$ is hydrogen or one, two, three or four substituents each selected from halogen, cyano, hydroxy, $C_{1-8}$alkyl, $C_{2-8}$alkenyl, $C_{2-8}$alkynyl, $C_{1-8}$alkoxy, halo-$C_{1-8}$alkyl, halo-$C_{1-8}$alkoxy, hydroxy-$C_{1-8}$alkyl, $C_{1-8}$alkoxy-$C_{1-8}$alkyl, $C_{1-8}$alkoxy-$C_{1-8}$ alkoxy, $C_{1-8}$alkoxy-$C_{1-8}$alkoxy-$C_{1-8}$alkoxy, carboxy, amino, $C_{1-8}$alkyl-amino, amino-$C_{1-8}$alkyl, $C_{1-8}$alkyl-amino-$C_{1-8}$alkyl, $C_{1-8}$alkyl-carbonyl, $C_{1-8}$alkoxy-carbonyl, aminosulfonyl, $C_{1-8}$alkyl-aminosulfonyl, $C_{1-8}$alkyl-carbonyl-amino and $C_{1-8}$alkoxy-carbonyl-amino;

$R^2$ is hydrogen or $C_{1-8}$alkyl;

$R^4$ and $R^5$ are each hydrogen, $C_{1-8}$alkyl or halo-$C_{1-8}$alkyl; and $R^6$ is hydrogen or one, two, three or four substituents each selected from halogen, hydroxy or $C_{1-8}$alkyl;

with the proviso that the compound of Formula (Id), Formula (Ie), Formula (If) or Formula (Ig) is other than:

N-(2,6-dibromo-4-methoxyphenyl)-4-(2-methylimidazo[1,2-a]pyrimidin-3-yl)thiazol-2-amine, N-(3-chloro-2-methylphenyl)-4-(2-methylimidazo[1,2-a]pyrimidin-3-yl)thiazol-2-amine, N-(2,5-dimethoxyphenyl)-4-(2-methylimidazo[1,2-a]pyrimidin-3-yl)thiazol-2-amine, N-(2-ethoxyphenyl)-4-(2-methylimidazo[1,2-a]pyrimidin-3-yl)thiazol-2-amine, N-(2-chlorophenyl)-4-(2-methylimidazo[1,2-a]pyrimidin-3-yl)thiazol-2-amine, 4-(2-methylimidazo[1,2-a]pyrimidin-3-yl)-N-m-tolylthiazol-2-amine, N,N-diethyl-N'-(4-(2-methylimidazo[1,2-a]pyrimidin-3-yl)thiazol-2-yl)benzene-1,4-diamine, N-(2-methoxyphenyl)-4-(2-methylimidazo[1,2-a]pyrimidin-3-yl)thiazol-2-amine, 1-(3-(4-(2-methylimidazo[1,2-a]pyrimidin-3-yl)thiazol-2-ylamino)phenyl)ethanone,
4-(4-(2-methylimidazo[1,2-a]pyrimidin-3-yl)thiazol-2-ylamino)benzenesulfonamide,
N-(4-(4-(2-methylimidazo[1,2-a]pyrimidin-3-yl)thiazol-2-ylamino)phenyl)acetamide,
N,N-dimethyl-N'-(4-(2-methylimidazo[1,2-a]pyrimidin-3-yl)thiazol-2-yl)benzene-1,4-diamine,
N-(4-ethoxyphenyl)-4-(2-methylimidazo[1,2-a]pyrimidin-3-yl)thiazol-2-amine,
N-(4-methoxyphenyl)-4-(2-methylimidazo[1,2-a]pyrimidin-3-yl)thiazol-2-amine,
4-(4-(2-methylimidazo[1,2-a]pyrimidin-3-yl)thiazol-2-ylamino)benzoic acid,
4-(4-(2,7-dimethylimidazo[1,2-a]pyridin-3-yl)thiazol-2-ylamino)phenol,
4-(2,7-dimethylimidazo[1,2-a]pyridin-3-yl)-N-(4-methoxyphenyl)thiazol-2-amine, and
4-(2,7-dimethylimidazo[1,2-a]pyridin-3-yl)-N-(2-methoxyphenyl)thiazol-2-amine.

In one embodiment is a compound of Formula (Id) selected from a compound of Formula (Ih) or a form thereof:

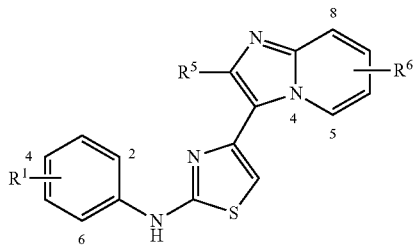

(Ih)

wherein $R^1$, $R^5$ and $R^6$ are each dependently selected from:

| Cpd | $R^1$ | $R^5$ | $R^6$ |
|---|---|---|---|
| 16 | 4-OH | Me | 7-Me |
| 17 | 4-OMe | Me | 7-Me |
| 18 | 2-OMe | Me | 7-Me |
| 24 | 2,6-Br$_2$-4-OMe | H | 6-Cl |
| 25 | 2,6-Br$_2$-4-Me | H | 6-Cl |
| 26 | 2,6-Cl$_2$-4-OMe | H | 6-Cl |
| 27 | 2,6-Me$_2$-4-OMe | H | 6-Cl |
| 29 | 4-I | Me | 6-Cl |
| 31 | 3-OH | Me | 7-Me |
| 32 | 4-Me | Me | 7-Me |
| 33 | 4-C(O)Me | Me | 7-Me |
| 35 | 3-OH | Me | H |
| 36 | 4-OH | Me | H |
| 41 | 4-N(Me)$_2$ | Me | H |
| 44 | 4-OMe | Me | H |
| 50 | 3-Cl-4-OMe | Me | H |
| 51 | 3-F-4-OMe | Me | H |
| 52 | 4-(OEt—OMe) | Me | H |
| 53 | 4-I | Me | H |
| 54 | 2,6-Br$_2$-4-(OEt—OMe) | Me | H |
| 55 | 4-C(O)Me | Me | H |
| 57 | 2,6-F$_2$-4-OMe | Me | H |
| 58 | 4-N(Me)$_2$ | Me | 6-Cl |
| 59 | 4-OMe | Me | 6-Cl |
| 60 | 4-Cl | Me | 6-Cl |
| 61 | 4-Br | Me | 6-Cl |
| 62 | 4-C(O)Me | Me | 6-Cl |
| 64 | 4-N(Me)$_2$ | Me | 7-Me |
| 65 | 4-Cl | Me | 7-Me |
| 66 | 3-F-4-OMe | Me | 7-Me |
| 67 | 3-Cl-4-OMe | Me | 7-Me |
| 68 | 4-Br | Me | 7-Me |
| 69 | 4-I | Me | 7-Me |
| 70 | 4-N(Me)$_2$ | Me | 6-Me |
| 71 | 4-OMe | Me | 6-Me |
| 73 | 3-Cl-4-OMe | Me | 6-Me |
| 74 | 4-(OEt—OMe) | Me | 6-Me |
| 75 | 4-N(Et)$_2$ | Me | 6-Me |
| 76 | 4-I | Me | 6-Me |
| 77 | 4-Br | Me | 6-Me |
| 78 | 4-Cl | Me | 6-Me |
| 79 | 4-I | H | H |
| 81 | 4-N(Me)$_2$ | Me | 6-Br |
| 88 | 4-OEt | Me | 6-Cl |
| 89 | 4-Me | Me | 6-Cl |
| 90 | 4-Et | Me | 6-Cl |
| 91 | 4-i-Pr | Me | 6-Cl |
| 92 | 4-OH | Me | 6-Cl |
| 93 | 4-(OEt—OMe) | Me | 6-Cl |
| 95 | 3-Cl-4-OMe | Me | 6-Cl |
| 96 | 3-F-4-OMe | Me | 6-Cl |
| 97 | 4-NHC(O)Me | Me | 6-Cl |
| 98 | 2,6-Cl$_2$ | Me | 6-Cl |
| 99 | 4-C(O)Me | Me | 6-Br |
| 100 | 4-Cl | Me | 6-Br |
| 101 | 4-I | Me | 6-Br |
| 102 | 4-Br | Me | 6-Br |
| 103 | 3-Cl-4-OMe | Me | 6-Br |
| 104 | 3-F-4-OMe | Me | 6-Br |
| 105 | 4-OMe | H | 6-Cl |
| 106 | 4-N(Me)$_2$ | H | 6-Cl |
| 107 | 4-C(O)Me | H | 6-Cl |
| 108 | 4-I | H | 6-Cl |
| 109 | 3-Cl-4-OMe | H | 6-Cl |
| 110 | 3-F-4-OMe | H | 6-Cl |
| 111 | 3,4-Cl$_2$ | Me | 6-Cl |
| 112 | 4-t-Bu | Me | 6-Cl |
| 132 | 2-Cl-4-Br | Me | 6-Cl |
| 133 | H | Me | 6-Cl |
| 134 | 2,6-Br$_2$-4-(OEt—OMe) | H | 6-Cl |
| 135 | 2,4,6-Br$_3$ | H | 6-Cl |
| 136 | 2,4,6-Cl$_3$ | H | 6-Cl |
| 155 | 3-F-4-OMe | Me | 6-F |
| 156 | 4-I | Me | 6-F |
| 157 | 4-N(Me)$_2$ | Me | 6-F |
| 159 | 4-C(O)Me | Me | 6-F |
| 160 | 4-OMe | Me | 6-F |
| 161 | 4-Cl | Me | 6-F |
| 162 | 4-Br | Me | 6-F |
| 163 | 4-OEt | Me | 6-F |
| 164 | 4-t-Bu | Me | 6-F |
| 165 | 2-Cl-4-Br | Me | 6-F |
| 171 | 3-F-4-OMe | n-Pr | H |
| 172 | 3-Cl-4-OMe | n-Pr | H |
| 173 | 4-OEt | n-Pr | H |
| 174 | 4-I | n-Pr | H |
| 176 | 4-N(Me)$_2$ | n-Pr | H |
| 177 | 4-C(O)Me | n-Pr | H |
| 178 | 4-Cl | n-Pr | H |
| 179 | 4-Br | n-Pr | H |
| 180 | 4-Me | n-Pr | H |
| 188 | 3-OMe | Me | H |
| 191 | 4-Me | Me | H |
| 192 | 4-Et | Me | H |
| 193 | 4-N(Et)$_2$ | Me | H |
| 194 | 4-NHC(O)Me | Me | H |
| 197 | 4-Br | Me | H |
| 198 | 3,4-Cl$_2$ | Me | H |
| 199 | 4-Cl | Me | H |
| 200 | 2-Cl-4-Br | Me | H |
| 201 | 3,4-(OH)$_2$ | Me | H |
| 202 | 3,4-(OMe)$_2$ | Me | H |
| 203 | 2,4-F$_2$ | Me | H |
| 204 | 4-OEt | Me | H |
| 205 | 2-Br-4-Me | Me | 6-Cl |
| 206 | 4-N(Et)$_2$ | Me | 6-Cl |
| 207 | 3,4-(OMe)$_2$ | Me | 6-Cl |
| 208 | 2-Br-4-OMe | Me | 6-Cl |

| Cpd | R¹ | R⁵ | R⁶ |
|---|---|---|---|
| 209 | 3-Me | Me | 6-Cl |
| 210 | 3-OH | Me | 6-Cl |
| 211 | 3-C(O)Me | Me | 6-Cl |
| 212 | 3-Br | Me | 6-Cl |
| 213 | 3-Cl | Me | 6-Cl |
| 214 | 2,4-Me$_2$ | Me | 6-Cl |
| 215 | 3-F | Me | 6-Cl |
| 216 | 2-Me-4-Br | Me | 6-Cl |
| 217 | 3-OMe | Me | 6-Cl |
| 218 | 2,4-Cl$_2$ | Me | 6-Cl |
| 221 | 4-N(Me)$_2$ | Me | 8-Me |
| 222 | 4-OMe | Me | 8-Me |
| 223 | 4-Me | Me | 8-Me |
| 224 | 4-Cl | Me | 8-Me |
| 225 | 3-OMe | Me | 8-Me |
| 227 | 4-N(Me)$_2$ | Me | 8-Br |
| 228 | 4-OMe | Me | 8-Br |
| 229 | 4-Me | Me | 8-Br |
| 230 | 4-Cl | Me | 8-Br |
| 231 | H | Me | 8-Br |
| 232 | 3-OMe | Me | 8-Br |
| 233 | 2-Cl | Me | 8-Br |
| 234 | 2-OMe | Me | 8-Br |
| 236 | 3-OMe | Me | 6-F |
| 237 | 4-Me | Me | 6-F |
| 238 | 3-C(O)Me | Me | 6-F |
| 239 | 2,6-Br$_2$ | Me | 6-F |
| 240 | 4-Cl | Me | 7-Cl |
| 241 | 4-OMe | Me | 7-Cl |
| 242 | 4-N(Me)$_2$ | Me | 7-Cl |
| 243 | 4-Me | Me | 7-Cl |
| 244 | 4-C(O)Me | Me | 7-Cl |

In one embodiment is a compound of Formula (Ie) selected from a compound of Formula (Ii) or a form thereof:

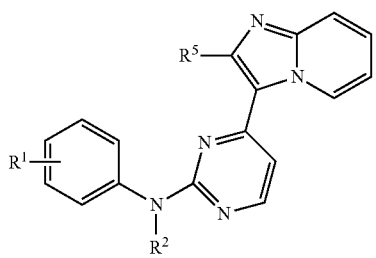

(Ii)

wherein R¹, R² and R⁵ are each dependently selected from:

| Cpd | R¹ | R² | R⁵ |
|---|---|---|---|
| 28 | 3-OMe | H | H |
| 113 | 4-Cl | H | Me |
| 114 | 4-Br | H | Me |
| 115 | 4-OMe | H | Me |
| 116 | 4-OEt | H | Me |
| 117 | 4-C(O)Me | H | Me |
| 118 | 4-N(Me)$_2$ | H | Me |
| 119 | 4-I | H | Me |
| 127 | 3-Br | H | Me |
| 128 | 4-OEt | H | Me |
| 129 | 4-N(Me)$_2$ | H | Me |
| 130 | 4-N(Et)$_2$ | H | Me |
| 137 | 4-N(Me)$_2$ | Me | Me |
| 138 | 4-N(Et)$_2$ | Me | Me |
| 141 | 2,6-Me$_2$-4-OMe | H | Me |
| 142 | 4-OEt | Me | Me |
| 143 | 4-I | Me | Me |
| 166 | 2-F | H | H |
| 167 | 4-C(O)Me | Me | Me |
| 169 | 4-Me | H | Me |
| 189 | 4-Me | Me | Me |
| 190 | 3-OH | H | Me |
| 196 | 4-CO$_2$H | H | Me |
| 245 | 4-OMe | H | H |
| 246 | 3-Cl | H | H |
| 247 | 2-Cl | H | H |
| 248 | 4-F | H | H |
| 249 | 2,6-Br$_2$-4-OMe | H | H |
| 250 | 4-C(O)Me | H | H |
| 252 | 4-OEt | H | H |
| 253 | 4-N(Et)$_2$ | H | H |
| 254 | 4-N(Me)$_2$ | H | H |
| 255 | 3-F | H | H |
| 256 | 3-Br | H | H |

In one embodiment is a compound of Formula (Id) selected from a compound of Formula (Ij) or a form thereof:

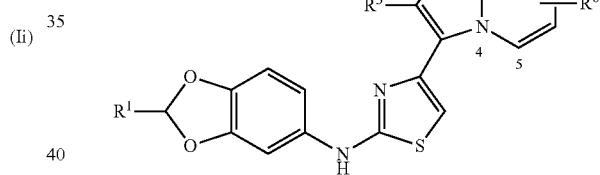

(Ij)

wherein Ar$_1$, R¹, R⁵ and R⁶ are each dependently selected from:

| Cpd | R¹ | R⁵ | R⁶ |
|---|---|---|---|
| 30 | H | Me | 6-Cl |
| 56 | H | Me | H |
| 63 | H | Me | 7-Me |
| 72 | H | Me | 6-Me |
| 82 | H | Me | 6-Br |
| 94 | H | Me | 8-OH |
| 158 | H | Me | 6-F |
| 175 | H | n-Pr | H |
| 195 | H | CF$_3$ | H |
| 219 | 2,2-Me$_2$ | Me | 6-Cl |
| 220 | H | Me | 6,8-Cl$_2$ |
| 226 | H | Me | 8-Me |
| 235 | H | Me | 8-Br |

In one embodiment is a compound of Formula (Ie) selected from a compound of Formula (Ik) or a form thereof:

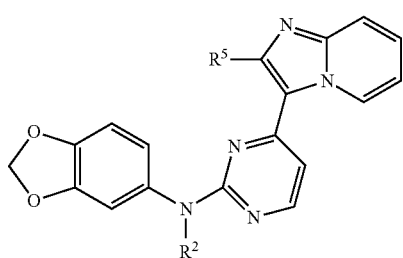

(Ik)

wherein $Ar_1$, $R^2$ and $R^5$ are each dependently selected from:

| Cpd | $R^2$ | $R^5$ |
|---|---|---|
| 123 | H | Me |
| 139 | Me | Me |
| 251 | H | H |

In one embodiment is a compound of Formula (If) selected from a compound of Formula (Il) or a form thereof:

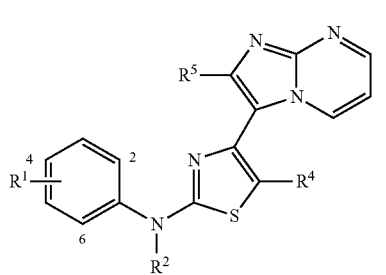

(Il)

wherein $R^1$, $R^2$, $R^4$ and $R^5$ are each dependently selected from:

| Cpd | $R^1$ | $R^2$ | $R^4$ | $R^5$ |
|---|---|---|---|---|
| 1 | 2,6-Br$_2$-4-OMe | H | H | Me |
| 2 | 3-Cl-2-Me | H | H | Me |
| 3 | 2,5-(OMe)$_2$ | H | H | Me |
| 4 | 2-OEt | H | H | Me |
| 5 | 2-Cl | H | H | Me |
| 6 | 3-Me | H | H | Me |
| 7 | 4-N(Et)$_2$ | H | H | Me |
| 8 | 2-OMe | H | H | Me |
| 9 | 3-C(O)Me | H | H | Me |
| 10 | 4-SO$_2$NH$_2$ | H | H | Me |
| 11 | 4-NHC(O)Me | H | H | Me |
| 12 | 4-N(Me)$_2$ | H | H | Me |
| 13 | 4-OEt | H | H | Me |
| 14 | 4-OMe | H | H | Me |
| 15 | 4-CO$_2$H | H | H | Me |
| 19 | 2,6-Cl$_2$-4-OMe | H | H | Me |
| 20 | 2,6-F$_2$-4-OMe | H | H | Me |
| 21 | 2,6-Br$_2$-4-Me | H | H | Me |
| 22 | 2,4,6-Br$_3$ | H | H | Me |
| 23 | 2,6-Br$_2$-4-(OEt—OMe) | H | H | Me |
| 34 | 4-C(O)Me | H | H | Me |
| 38 | 2,6-Cl$_2$ | H | H | Me |
| 39 | 4-I | H | H | Me |
| 45 | 3-F-4-OMe | H | H | Me |
| 46 | 3-Cl-4-OMe | H | H | Me |
| 48 | 4-Br | H | H | Me |
| 49 | 4-Cl | H | H | Me |
| 80 | 4-Br | Me | H | Me |
| 83 | 4-I | H | H | H |
| 84 | 3,4-(OMe)$_2$ | H | H | Me |
| 85 | 4-Me | H | H | Me |
| 86 | 4-Et | H | H | Me |
| 87 | 4-i-Pr | H | H | Me |
| 121 | 4-Br | H | Me | Me |
| 122 | 4-I | H | Me | Me |
| 144 | 4-OMe | H | H | Et |
| 145 | 4-N(Me)$_2$ | H | H | Et |
| 146 | 2,6-Br$_2$-4-Me | H | H | Et |
| 147 | 4-Cl | H | H | Et |
| 148 | 4-Br | H | H | Et |
| 149 | 4-I | H | H | Et |
| 150 | 4-C(O)Me | H | H | Et |
| 152 | 3-F-4-OMe | H | H | Et |
| 153 | 3-Cl-4-OMe | H | H | Et |
| 181 | 3-F-4-OMe | H | H | n-Pr |
| 183 | 4-N(Me)$_2$ | H | H | n-Pr |
| 184 | 4-Br | H | H | n-Pr |
| 185 | 4-I | H | H | n-Pr |
| 186 | 4-OMe | H | H | n-Pr |
| 187 | H | H | H | n-Pr |

In one embodiment is a compound of Formula (Ig) selected from a compound of Formula (Im) or a form thereof:

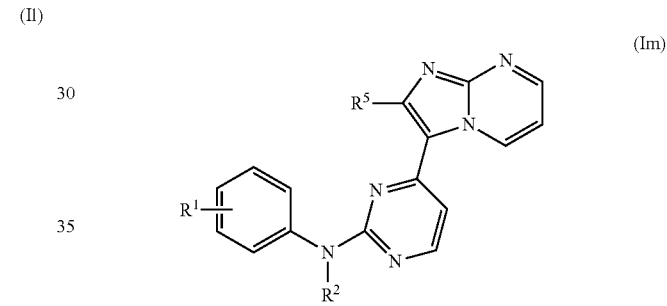

(Im)

wherein $R^1$, $R^2$ and $R^5$ are each dependently selected from:

| Cpd | $R^1$ | $R^2$ | $R^5$ |
|---|---|---|---|
| 42 | 4-OMe | H | Me |
| 43 | 4-N(Me)$_2$ | H | Me |
| 47 | 4-OMe | Me | Me |
| 120 | 4-I | H | Me |
| 125 | 4-I | Me | Me |
| 126 | 4-Br | H | Me |
| 131 | 4-C(O)Me | H | Me |
| 140 | 2-Cl | Me | Me |
| 168 | 4-Me | H | Me |
| 170 | 4-Me | Me | Me |
| 257 | 2,6-Br$_2$-4-OMe | H | H |
| 258 | 4-C(O)Me | H | H |
| 260 | 3-OMe | H | H |
| 261 | 4-OMe | H | H |
| 262 | 4-OEt | H | H |
| 263 | 4-N(Et)$_2$ | H | H |
| 264 | 3-N(Me)$_2$ | H | H |
| 265 | 4-N(Me)$_2$ | H | H |
| 266 | 2-F | H | H |
| 267 | 3-F | H | H |
| 268 | 4-F | H | H |
| 269 | 3-Cl | H | H |
| 270 | 4-Br | H | H |
| 271 | 4-Br | H | Et |

In one embodiment is a compound of Formula (If) selected from a compound of Formula (In) or a form thereof:

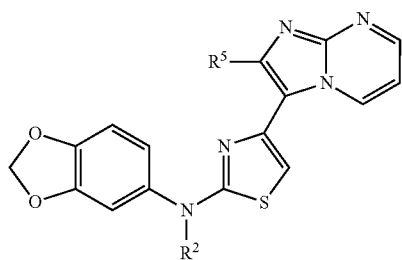

(In)

wherein $R^1$, $R^2$, $R^5$ and $R^6$ are each dependently selected from:

| Cpd | $R^2$ | $R^5$ |
|---|---|---|
| 37 | H | Me |
| 40 | Me | Me |
| 151 | H | Et |
| 154 | H | $CF_3$ |
| 182 | H | n-Pr |

In one embodiment is a compound of Formula (Ig) selected from a compound of Formula (Io) or a form thereof:

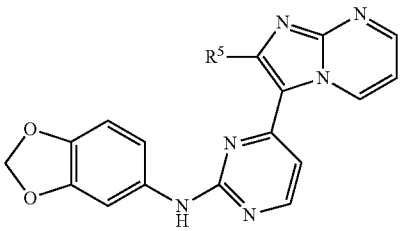

(Io)

wherein $R^1$, $R^2$, $R^5$ and $R^6$ are each dependently selected from:

| Cpd | $R^5$ |
|---|---|
| 124 | Me |
| 259 | H |

In another embodiment is a compound selected from a compound of any of Formula (Ia)-Formula (Io) or a form thereof, wherein the form is selected from a free acid, free base, salt, ester, hydrate, solvate, chelate, clathrate, isotopologue, geometric isomer, stereoisomer, racemate, enantiomer, diastereomer, tautomer or polymorph thereof. In certain embodiments, the form of the compound of Formula (I) is pharmaceutically acceptable.

Alternatively, a compound of Formula (I) is selected from the group consisting of:

| Cpd | Name |
|---|---|
| 19 | N-(2,6-dichloro-4-methoxyphenyl)-4-(2-methylimidazo[1,2-a]pyrimidin-3-yl)thiazol-2-amine, |
| 20 | N-(2,6-difluoro-4-methoxyphenyl)-4-(2-methylimidazo[1,2-a]pyrimidin-3-yl)thiazol-2-amine, |
| 21 | N-(2,6-dibromo-4-methylphenyl)-4-(2-methylimidazo[1,2-a]pyrimidin-3-yl)thiazol-2-amine, |
| 22 | 4-(2-methylimidazo[1,2-a]pyrimidin-3-yl)-N-(2,4,6-tribromophenyl)thiazol-2-amine, |
| 23 | N-(2,6-dibromo-4-(2-methoxyethoxy)phenyl)-4-(2-methylimidazo[1,2-a]pyrimidin-3-yl)thiazol-2-amine, |
| 24 | 4-(6-chloroimidazo[1,2-a]pyridine-3-yl)-N-(2,6-dibromo-4-methoxyphenyl)thiazol-2-amine, |
| 25 | 4-(6-chloroimidazo[1,2-a]pyridine-3-yl)-N-(2,6-dibromo-4-methylphenyl)thiazol-2-amine, |
| 26 | 4-(6-chloroimidazo[1,2-a]pyridine-3-yl)-N-(2,6-dichloro-4-methoxyphenyl)thiazol-2-amine, |
| 27 | 4-(6-chloroimidazo[1,2-a]pyridine-3-yl)-N-(4-methoxy-2,6-dimethylphenyl)thiazol-2-amine, |
| 28 | 4-(imidazo[1,2-a]pyridine-3-yl)-N-(3-methoxyphenyl)pyrimidin-2-amine, |
| 29 | 4-(6-chloro-2-methylimidazo[1,2-a]pyridin-3-yl)-N-(4-iodophenyl)thiazol-2-amine, |
| 30 | N-(benzo[d][1,3]dioxol-5-yl)-4-(6-chloro-2-methylimidazo[1,2-a]pyridin-3-yl)thiazol-2-amine, |
| 31 | 3-{[4-(2,7-dimethylimidazo[1,2-a]pyridin-3-yl)-1,3-thiazol-2-yl]amino}phenol, |
| 32 | 4-(2,7-dimethylimidazo[1,2-a]pyridin-3-yl)-N-(4-methylphenyl)-1,3-thiazol-2-amine, |
| 33 | 1-(4-{[4-(2,7-dimethylimidazo[1,2-a]pyridin-3-yl)-1,3-thiazol-2-yl]amino}phenyl)ethanone, |
| 34 | 1-(4-{[4-(2-methylimidazo[1,2-a]pyrimidin-3-yl)-1,3-thiazol-2-yl]amino}phenyl)ethanone, |
| 35 | 3-{[4-(2-methylimidazo[1,2-a]pyridin-3-yl)-1,3-thiazol-2-yl]amino}phenol, |
| 36 | 4-{[4-(2-methylimidazo[1,2-a]pyridin-3-yl)-1,3-thiazol-2-yl]amino}phenol, |
| 37 | N-(1,3-benzodioxol-5-yl)-4-(2-methylimidazo[1,2-a]pyrimidin-3-yl)-1,3-thiazol-2-amine, |
| 38 | N-(2,6-dichlorophenyl)-4-(2-methylimidazo[1,2-a]pyrimidin-3-yl)-1,3-thiazol-2-amine, |
| 39 | N-(4-iodophenyl)-4-(2-methylimidazo[1,2-a]pyrimidin-3-yl)-1,3-thiazol-2-amine, |
| 40 | N-(1,3-benzodioxol-5-yl)-N-methyl-4-(2-methylimidazo[1,2-a]pyrimidin-3-yl)-1,3-thiazol-2-amine, |
| 41 | N,N-dimethyl-N'-[4-(2-methylimidazo[1,2-a]pyridin-3-yl)-1,3-thiazol-2-yl]benzene-1,4-diamine, |
| 42 | N-(4-methoxyphenyl)-4-(2-methylimidazo[1,2-a]pyridin-3-yl)pyrimidin-2-amine, |
| 43 | N,N-dimethyl-N'-[4-(2-methylimidazo[1,2-a]pyridin-3-yl)pyrimidin-2-yl]benzene-1,4-diamine, |

-continued

| Cpd | Name |
|---|---|
| 44 | N-(4-methoxyphenyl)-4-(2-methylimidazo[1,2-a]pyridin-3-yl)-1,3-thiazol-2-amine, |
| 45 | N-(3-fluoro-4-methoxyphenyl)-4-(2-methylimidazo[1,2-a]pyrimidin-3-yl)-1,3-thiazol-2-amine, |
| 46 | N-(3-chloro-4-methoxyphenyl)-4-(2-methylimidazo[1,2-a]pyrimidin-3-yl)-1,3-thiazol-2-amine, |
| 47 | N-(4-methoxyphenyl)-N-methyl-4-(2-methylimidazo[1,2-a]pyrimidin-3-yl)pyrimidin-2-amine, |
| 48 | N-(4-bromophenyl)-4-(2-methylimidazo[1,2-a]pyrimidin-3-yl)-1,3-thiazol-2-amine, |
| 49 | N-(4-chlorophenyl)-4-(2-methylimidazo[1,2-a]pyrimidin-3-yl)-1,3-thiazol-2-amine, |
| 50 | N-(3-chloro-4-methoxyphenyl)-4-(2-methylimidazo[1,2-a]pyridin-3-yl)-1,3-thiazol-2-amine, |
| 51 | N-(3-fluoro-4-methoxyphenyl)-4-(2-methylimidazo[1,2-a]pyridin-3-yl)-1,3-thiazol-2-amine, |
| 52 | N-[4-(2-methoxyethoxy)phenyl]-4-(2-methylimidazo[1,2-a]pyridin-3-yl)-1,3-thiazol-2-amine, |
| 53 | N-(4-iodophenyl)-4-(2-methylimidazo[1,2-a]pyridin-3-yl)-1,3-thiazol-2-amine, |
| 54 | N-[2,6-dibromo-4-(2-methoxyethoxy)phenyl]-4-(2-methylimidazo[1,2-a]pyridin-3-yl)-1,3-thiazol-2-amine, |
| 55 | 1-(4-{[4-(2-methylimidazo[1,2-a]pyridin-3-yl)-1,3-thiazol-2-yl]amino}phenyl)ethanone, |
| 56 | N-(1,3-benzodioxol-5-yl)-4-(2-methylimidazo[1,2-a]pyridin-3-yl)-1,3-thiazol-2-amine, |
| 57 | N-(2,6-difluoro-4-methoxyphenyl)-4-(2-methylimidazo[1,2-a]pyridin-3-yl)-1,3-thiazol-2-amine, |
| 58 | N'-[4-(6-chloro-2-methylimidazo[1,2-a]pyridin-3-yl)-1,3-thiazol-2-yl]-N,N-dimethylbenzene-1,4-diamine, |
| 59 | 4-(6-chloro-2-methylimidazo[1,2-a]pyridin-3-yl)-N-(4-methoxyphenyl)-1,3-thiazol-2-amine, |
| 60 | 4-(6-chloro-2-methylimidazo[1,2-a]pyridin-3-yl)-N-(4-chlorophenyl)-1,3-thiazol-2-amine, |
| 61 | N-(4-bromophenyl)-4-(6-chloro-2-methylimidazo[1,2-a]pyridin-3-yl)-1,3-thiazol-2-amine, |
| 62 | 1-(4-{[4-(6-chloro-2-methylimidazo[1,2-a]pyridin-3-yl)-1,3-thiazol-2-yl]amino}phenyl)ethanone, |
| 63 | N-(1,3-benzodioxol-5-yl)-4-(2,7-dimethylimidazo[1,2-a]pyridin-3-yl)-1,3-thiazol-2-amine, |
| 64 | N'-[4-(2,7-dimethylimidazo[1,2-a]pyridin-3-yl)-1,3-thiazol-2-yl]-N,N-dimethylbenzene-1,4-diamine, |
| 65 | N-(4-chlorophenyl)-4-(2,7-dimethylimidazo[1,2-a]pyridin-3-yl)-1,3-thiazol-2-amine, |
| 66 | 4-(2,7-dimethylimidazo[1,2-a]pyridin-3-yl)-N-(3-fluoro-4-methoxyphenyl)-1,3-thiazol-2-amine, |
| 67 | N-(3-chloro-4-methoxyphenyl)-4-(2,7-dimethylimidazo[1,2-a]pyridin-3-yl)-1,3-thiazol-2-amine, |
| 68 | N-(4-bromophenyl)-4-(2,7-dimethylimidazo[1,2-a]pyridin-3-yl)-1,3-thiazol-2-amine, |
| 69 | 4-(2,7-dimethylimidazo[1,2-a]pyridin-3-yl)-N-(4-iodophenyl)-1,3-thiazol-2-amine, |
| 70 | N'-[4-(2,6-dimethylimidazo[1,2-a]pyridin-3-yl)-1,3-thiazol-2-yl]-N,N-dimethylbenzene-1,4-diamine, |
| 71 | 4-(2,6-dimethylimidazo[1,2-a]pyridin-3-yl)-N-(4-methoxyphenyl)-1,3-thiazol-2-amine, |
| 72 | N-(1,3-benzodioxol-5-yl)-4-(2,6-dimethylimidazo[1,2-a]pyridin-3-yl)-1,3-thiazol-2-amine, |
| 73 | N-(3-chloro-4-methoxyphenyl)-4-(2,6-dimethylimidazo[1,2-a]pyridin-3-yl)-1,3-thiazol-2-amine, |
| 74 | 4-(2,6-dimethylimidazo[1,2-a]pyridin-3-yl)-N-[4-(2-methoxyethoxy)phenyl]-1,3-thiazol-2-amine, |
| 75 | N'-[4-(2,6-dimethylimidazo[1,2-a]pyridin-3-yl)-1,3-thiazol-2-yl]-N,N-diethylbenzene-1,4-diamine, |
| 76 | 4-(2,6-dimethylimidazo[1,2-a]pyridin-3-yl)-N-(4-iodophenyl)-1,3-thiazol-2-amine, |
| 77 | N-(4-bromophenyl)-4-(2,6-dimethylimidazo[1,2-a]pyridin-3-yl)-1,3-thiazol-2-amine, |
| 78 | N-(4-chlorophenyl)-4-(2,6-dimethylimidazo[1,2-a]pyridin-3-yl)-1,3-thiazol-2-amine, |
| 79 | 4-(imidazo[1,2-a]pyridin-3-yl)-N-(4-iodophenyl)-1,3-thiazol-2-amine, |
| 80 | N-(4-bromophenyl)-N-methyl-4-(2-methylimidazo[1,2-a]pyridin-3-yl)-1,3-thiazol-2-amine, |
| 81 | N'-[4-(6-bromo-2-methylimidazo[1,2-a]pyridin-3-yl)-1,3-thiazol-2-yl]-N,N-dimethylbenzene-1,4-diamine, |
| 82 | N-(1,3-benzodioxol-5-yl)-4-(6-bromo-2-methylimidazo[1,2-a]pyridin-3-yl)-1,3-thiazol-2-amine, |
| 83 | 4-(imidazo[1,2-a]pyrimidin-3-yl)-N-(4-iodophenyl)-1,3-thiazol-2-amine, |
| 84 | N-(3,4-dimethoxyphenyl)-4-(2-methylimidazo[1,2-a]pyrimidin-3-yl)-1,3-thiazol-2-amine, |
| 85 | 4-(2-methylimidazo[1,2-a]pyrimidin-3-yl)-N-(4-methylphenyl)-1,3-thiazol-2-amine, |
| 86 | N-(4-ethylphenyl)-4-(2-methylimidazo[1,2-a]pyrimidin-3-yl)-1,3-thiazol-2-amine, |
| 87 | 4-(2-methylimidazo[1,2-a]pyrimidin-3-yl)-N-[4-(propan-2-yl)phenyl]-1,3-thiazol-2-amine, |
| 88 | 4-(6-chloro-2-methylimidazo[1,2-a]pyridin-3-yl)-N-(4-ethoxyphenyl)-1,3-thiazol-2-amine, |
| 89 | 4-(6-chloro-2-methylimidazo[1,2-a]pyridin-3-yl)-N-(4-methylphenyl)-1,3-thiazol-2-amine, |
| 90 | 4-(6-chloro-2-methylimidazo[1,2-a]pyridin-3-yl)-N-(4-ethylphenyl)-1,3-thiazol-2-amine, |
| 91 | 4-(6-chloro-2-methylimidazo[1,2-a]pyridin-3-yl)-N-[4-(propan-2-yl)phenyl]-1,3-thiazol-2-amine, |
| 92 | 4-{[4-(6-chloro-2-methylimidazo[1,2-a]pyridin-3-yl)-1,3-thiazol-2-yl]amino}phenol, |

-continued

| Cpd | Name |
|---|---|
| 93 | 4-(6-chloro-2-methylimidazo[1,2-a]pyridin-3-yl)-N-[4-(2-methoxyethoxy)phenyl]-1,3-thiazol-2-amine, |
| 94 | 3-[2-(1,3-benzodioxol-5-ylamino)-1,3-thiazol-4-yl]-2-methylimidazo[1,2-a]pyridin-8-ol, |
| 95 | N-(3-chloro-4-methoxyphenyl)-4-(6-chloro-2-methylimidazo[1,2-a]pyridin-3-yl)-1,3-thiazol-2-amine, |
| 96 | 4-(6-chloro-2-methylimidazo[1,2-a]pyridin-3-yl)-N-(3-fluoro-4-methoxyphenyl)-1,3-thiazol-2-amine, |
| 97 | N-(4-{[4-(6-chloro-2-methylimidazo[1,2-a]pyridin-3-yl)-1,3-thiazol-2-yl]amino}phenyl)acetamide, |
| 98 | 4-(6-chloro-2-methylimidazo[1,2-a]pyridin-3-yl)-N-(2,6-dichlorophenyl)-1,3-thiazol-2-amine, |
| 99 | 1-(4-{[4-(6-bromo-2-methylimidazo[1,2-a]pyridin-3-yl)-1,3-thiazol-2-yl]amino}phenyl)ethanone, |
| 100 | 4-(6-bromo-2-methylimidazo[1,2-a]pyridin-3-yl)-N-(4-chlorophenyl)-1,3-thiazol-2-amine, |
| 101 | 4-(6-bromo-2-methylimidazo[1,2-a]pyridin-3-yl)-N-(4-iodophenyl)-1,3-thiazol-2-amine, |
| 102 | 4-(6-bromo-2-methylimidazo[1,2-a]pyridin-3-yl)-N-(4-bromophenyl)-1,3-thiazol-2-amine, |
| 103 | 4-(6-bromo-2-methylimidazo[1,2-a]pyridin-3-yl)-N-(3-chloro-4-methoxyphenyl)-1,3-thiazol-2-amine, |
| 104 | 4-(6-bromo-2-methylimidazo[1,2-a]pyridin-3-yl)-N-(3-fluoro-4-methoxyphenyl)-1,3-thiazol-2-amine, |
| 105 | 4-(6-chloroimidazo[1,2-a]pyridin-3-yl)-N-(4-methoxyphenyl)-1,3-thiazol-2-amine, |
| 106 | N'-[4-(6-chloroimidazo[1,2-a]pyridin-3-yl)-1,3-thiazol-2-yl]-N,N-dimethylbenzene-1,4-diamine, |
| 107 | 1-(4-{[4-(6-chloroimidazo[1,2-a]pyridin-3-yl)-1,3-thiazol-2-yl]amino}phenyl)ethanone, |
| 108 | 4-(6-chloroimidazo[1,2-a]pyridin-3-yl)-N-(4-iodophenyl)-1,3-thiazol-2-amine, |
| 109 | 4-(6-chloroimidazo[1,2-a]pyridin-3-yl)-N-(3-chloro-4-methoxyphenyl)-1,3-thiazol-2-amine, |
| 110 | 4-(6-chloroimidazo[1,2-a]pyridin-3-yl)-N-(3-fluoro-4-methoxyphenyl)-1,3-thiazol-2-amine, |
| 111 | 4-(6-chloro-2-methylimidazo[1,2-a]pyridin-3-yl)-N-(3,4-dichlorophenyl)-1,3-thiazol-2-amine, |
| 112 | N-(4-tert-butylphenyl)-4-(6-chloro-2-methylimidazo[1,2-a]pyridin-3-yl)-1,3-thiazol-2-amine, |
| 113 | N-(4-chlorophenyl)-4-(2-methylimidazo[1,2-a]pyridin-3-yl)pyrimidin-2-amine, |
| 114 | N-(4-bromophenyl)-4-(2-methylimidazo[1,2-a]pyridin-3-yl)pyrimidin-2-amine, |
| 115 | N-(4-methoxyphenyl)-4-(2-methylimidazo[1,2-a]pyrimidin-3-yl)pyrimidin-2-amine, |
| 116 | N-(4-ethoxyphenyl)-4-(2-methylimidazo[1,2-a]pyrimidin-3-yl)pyrimidin-2-amine, |
| 117 | 1-(4-{[4-(2-methylimidazo[1,2-a]pyridin-3-yl)pyrimidin-2-yl]amino}phenyl)ethanone, |
| 118 | N,N-dimethyl-N'-[4-(2-methylimidazo[1,2-a]pyridin-3-yl)pyrimidin-2-yl]benzene-1,3-diamine, |
| 119 | N-(4-iodophenyl)-4-(2-methylimidazo[1,2-a]pyridin-3-yl)pyrimidin-2-amine, |
| 120 | N-(4-iodophenyl)-4-(2-methylimidazo[1,2-a]pyrimidin-3-yl)pyrimidin-2-amine, |
| 121 | N-(4-bromophenyl)-5-methyl-4-(2-methylimidazo[1,2-a]pyrimidin-3-yl)-1,3-thiazol-2-amine, |
| 122 | N-(4-iodophenyl)-5-methyl-4-(2-methylimidazo[1,2-a]pyrimidin-3-yl)-1,3-thiazol-2-amine, |
| 123 | N-(1,3-benzodioxol-5-yl)-4-(2-methylimidazo[1,2-a]pyridin-3-yl)pyrimidin-2-amine, |
| 124 | N-(1,3-benzodioxol-5-yl)-4-(2-methylimidazo[1,2-a]pyrimidin-3-yl)pyrimidin-2-amine, |
| 125 | N-(4-iodophenyl)-N-methyl-4-(2-methylimidazo[1,2-a]pyrimidin-3-yl)pyrimidin-2-amine, |
| 126 | N-(4-bromophenyl)-4-(2-methylimidazo[1,2-a]pyrimidin-3-yl)pyrimidin-2-amine, |
| 127 | N-(3-bromophenyl)-4-(2-methylimidazo[1,2-a]pyridin-3-yl)pyrimidin-2-amine, |
| 128 | N-(4-ethoxyphenyl)-4-(2-methylimidazo[1,2-a]pyridin-3-yl)pyrimidin-2-amine, |
| 129 | N,N-dimethyl-N'-[4-(2-methylimidazo[1,2-a]pyridin-3-yl)pyrimidin-2-yl]benzene-1,4-diamine, |
| 130 | N,N-diethyl-N'-[4-(2-methylimidazo[1,2-a]pyridin-3-yl)pyrimidin-2-yl]benzene-1,4-diamine, |
| 131 | 1-(4-{[4-(2-methylimidazo[1,2-a]pyrimidin-3-yl)pyrimidin-2-yl]amino}phenyl)ethanone, |
| 132 | N-(4-bromo-2-chlorophenyl)-4-(6-chloro-2-methylimidazo[1,2-a]pyridin-3-yl)-1,3-thiazol-2-amine, |
| 133 | 4-(6-chloro-2-methylimidazo[1,2-a]pyridin-3-yl)-N-phenyl-1,3-thiazol-2-amine, |
| 134 | 4-(6-chloroimidazo[1,2-a]pyridin-3-yl)-N-[2,6-dibromo-4-(2-methoxyethoxy)phenyl]-1,3-thiazol-2-amine, |
| 135 | 4-(6-chloroimidazo[1,2-a]pyridin-3-yl)-N-(2,4,6-tribromophenyl)-1,3-thiazol-2-amine, |
| 136 | 4-(6-chloroimidazo[1,2-a]pyridin-3-yl)-N-(2,4,6-trichlorophenyl)-1,3-thiazol-2-amine, |
| 137 | N,N,N'-trimethyl-N'-[4-(2-methylimidazo[1,2-a]pyridin-3-yl)pyrimidin-2-yl]benzene-1,4-diamine, |
| 138 | N,N-diethyl-N'-methyl-N'-[4-(2-methylimidazo[1,2-a]pyridin-3-yl)pyrimidin-2-yl]benzene-1,4-diamine, |
| 139 | N-(1,3-benzodioxol-5-yl)-N-methyl-4-(2-methylimidazo[1,2-a]pyridin-3-yl)pyrimidin-2-amine, |
| 140 | N-(2-chlorophenyl)-N-methyl-4-(2-methylimidazo[1,2-a]pyridin-3-yl)pyrimidin-2-amine, |
| 141 | N-(4-methoxy-2,6-dimethylphenyl)-4-(2-methylimidazo[1,2-a]pyridin-3-yl)pyrimidin-2-amine, |

-continued

| Cpd | Name |
|---|---|
| 142 | N-(4-ethoxyphenyl)-N-methyl-4-(2-methylimidazo[1,2-a]pyridin-3-yl)pyrimidin-2-amine, |
| 143 | N-(4-iodophenyl)-N-methyl-4-(2-methylimidazo[1,2-a]pyridin-3-yl)pyrimidin-2-amine, |
| 144 | 4-(2-ethylimidazo[1,2-a]pyrimidin-3-yl)-N-(4-methoxyphenyl)-1,3-thiazol-2-amine, |
| 145 | N'-[4-(2-ethylimidazo[1,2-a]pyrimidin-3-yl)-1,3-thiazol-2-yl]-N,N-dimethylbenzene-1,4-diamine, |
| 146 | N-(2,6-dibromo-4-methoxyphenyl)-4-(2-ethylimidazo[1,2-a]pyrimidin-3-yl)-1,3-thiazol-2-amine, |
| 147 | N-(4-chlorophenyl)-4-(2-ethylimidazo[1,2-a]pyrimidin-3-yl)-1,3-thiazol-2-amine, |
| 148 | N-(4-bromophenyl)-4-(2-ethylimidazo[1,2-a]pyrimidin-3-yl)-1,3-thiazol-2-amine, |
| 149 | 4-(2-ethylimidazo[1,2-a]pyrimidin-3-yl)-N-(4-iodophenyl)-1,3-thiazol-2-amine, |
| 150 | 1-(4-{[4-(2-ethylimidazo[1,2-a]pyrimidin-3-yl)-1,3-thiazol-2-yl]amino}phenyl)ethanone, |
| 151 | N-(1,3-benzodioxol-5-yl)-4-(2-ethylimidazo[1,2-a]pyrimidin-3-yl)-1,3-thiazol-2-amine, |
| 152 | 4-(2-ethylimidazo[1,2-a]pyrimidin-3-yl)-N-(3-fluoro-4-methoxyphenyl)-1,3-thiazol-2-amine, |
| 153 | N-(3-chloro-4-methoxyphenyl)-4-(2-ethylimidazo[1,2-a]pyrimidin-3-yl)-1,3-thiazol-2-amine, |
| 154 | N-(1,3-benzodioxol-5-yl)-4-[2-(trifluoromethyl)imidazo[1,2-a]pyrimidin-3-yl]-1,3-thiazol-2-amine, |
| 155 | N-(3-fluoro-4-methoxyphenyl)-4-(6-fluoro-2-methylimidazo[1,2-a]pyridin-3-yl)-1,3-thiazol-2-amine, |
| 156 | 4-(6-fluoro-2-methylimidazo[1,2-a]pyridine-3-yl)-N-(4-iodophenyl)-1,3-thiazol-2-amine, |
| 157 | N'-[4-(6-fluoro-2-methylimidazo[1,2-a]pyridin-3-yl)-1,3-thiazol-2-yl]-N,N-dimethylbenzene-1,4-diamine, |
| 158 | N-(1,3-benzodioxol-5-yl)-4-(6-fluoro-2-methylimidazo[1,2-a]pyridin-3-yl)-1,3-thiazol-2-amine, |
| 159 | 1-(4-{[4-(6-fluoro-2-methylimidazo[1,2-a]pyridin-3-yl)-1,3-thiazol-2-yl]amino}phenyl)ethanone, |
| 160 | 4-(6-fluoro-2-methylimidazo[1,2-a]pyridin-3-yl)-N-(4-methoxyphenyl)-1,3-thiazol-2-amine, |
| 161 | N-(4-chlorophenyl)-4-(6-fluoro-2-methylimidazo[1,2-a]pyridin-3-yl)-1,3-thiazol-2-amine, |
| 162 | N-(4-bromophenyl)-4-(6-fluoro-2-methylimidazo[1,2-a]pyridin-3-yl)-1,3-thiazol-2-amine, |
| 163 | N-(4-ethoxyphenyl)-4-(6-fluoro-2-methylimidazo[1,2-a]pyridin-3-yl)-1,3-thiazol-2-amine, |
| 164 | N-(4-tert-butylphenyl)-4-(6-fluoro-2-methylimidazo[1,2-a]pyridin-3-yl)-1,3-thiazol-2-amine, |
| 165 | N-(4-bromo-2-chlorophenyl)-4-(6-fluoro-2-methylimidazo[1,2-a]pyridin-3-yl)-1,3-thiazol-2-amine, |
| 166 | N-(2-fluorophenyl)-4-(imidazo[1,2-a]pyridin-3-yl)pyrimidin-2-amine, |
| 167 | 1-(4-{methyl[4-(2-methylimidazo[1,2-a]pyridin-3-yl)pyrimidin-2-yl]amino}phenyl)ethanone, |
| 168 | 4-(2-methylimidazo[1,2-a]pyrimidin-3-yl)-N-(4-methylphenyl)pyrimidin-2-amine, |
| 169 | 4-(2-methylimidazo[1,2-a]pyridin-3-yl)-N-(4-methylphenyl)pyrimidin-2-amine, |
| 170 | N-methyl-4-(2-methylimidazo[1,2-a]pyrimidin-3-yl)-N-(4-methylphenyl)pyrimidin-2-amine, |
| 171 | N-(3-fluoro-4-methoxyphenyl)-4-(2-propylimidazo[1,2-a]pyridin-3-yl)-1,3-thiazol-2-amine, |
| 172 | N-(3-chloro-4-methoxyphenyl)-4-(2-propylimidazo[1,2-a]pyridin-3-yl)-1,3-thiazol-2-amine, |
| 173 | N-(4-ethoxyphenyl)-4-(2-propylimidazo[1,2-a]pyridin-3-yl)-1,3-thiazol-2-amine, |
| 174 | N-(4-iodophenyl)-4-(2-propylimidazo[1,2-a]pyridin-3-yl)-1,3-thiazol-2-amine, |
| 175 | N-(1,3-benzodioxol-5-yl)-4-(2-propylimidazo[1,2-a]pyridin-3-yl)-1,3-thiazol-2-amine, |
| 176 | N,N-dimethyl-N'-[4-(2-propylimidazo[1,2-a]pyridin-3-yl)-1,3-thiazol-2-yl]benzene-1,4-diamine, |
| 177 | 1-(4-{[4-(2-propylimidazo[1,2-a]pyridin-3-yl)-1,3-thiazol-2-yl]amino}phenyl)ethanone, |
| 178 | N-(4-chlorophenyl)-4-(2-propylimidazo[1,2-a]pyridin-3-yl)-1,3-thiazol-2-amine, |
| 179 | N-(4-bromophenyl)-4-(2-propylimidazo[1,2-a]pyridin-3-yl)-1,3-thiazol-2-amine, |
| 180 | N-(4-methoxyphenyl)-4-(2-propylimidazo[1,2-a]pyridin-3-yl)-1,3-thiazol-2-amine, |
| 181 | N-(3-fluoro-4-methoxyphenyl)-4-(2-propylimidazo[1,2-a]pyrimidin-3-yl)-1,3-thiazol-2-amine, |
| 182 | N-(1,3-benzodioxol-5-yl)-4-(2-propylimidazo[1,2-a]pyrimidin-3-yl)-1,3-thiazol-2-amine, |
| 183 | N,N-dimethyl-N'-[4-(2-propylimidazo[1,2-a]pyrimidin-3-yl)-1,3-thiazol-2-yl]benzene-1,4-diamine, |
| 184 | N-(4-bromophenyl)-4-(2-propylimidazo[1,2-a]pyrimidin-3-yl)-1,3-thiazol-2-amine, |
| 185 | N-(4-iodophenyl)-4-(2-propylimidazo[1,2-a]pyrimidin-3-yl)-1,3-thiazol-2-amine, |
| 186 | N-(4-methoxyphenyl)-4-(2-propylimidazo[1,2-a]pyrimidin-3-yl)-1,3-thiazol-2-amine, |
| 187 | N-phenyl-4-(2-propylimidazo[1,2-a]pyrimidin-3-yl)-1,3-thiazol-2-amine, |
| 188 | N-(3-methoxyphenyl)-4-(2-methylimidazo[1,2-a]pyridin-3-yl)-1,3-thiazol-2-amine, |
| 189 | N-methyl-4-(2-methylimidazo[1,2-a]pyridin-3-yl)-N-(4-methylphenyl)pyrimidin-2-amine, |
| 190 | 3-{[4-(2-methylimidazo[1,2-a]pyridin-3-yl)pyrimidin-2-yl]amino}phenol, |
| 191 | 4-(2-methylimidazo[1,2-a]pyridin-3-yl)-N-(4-methylphenyl)-1,3-thiazol-2-amine, |
| 192 | N-(4-ethylphenyl)-4-(2-methylimidazo[1,2-a]pyridin-3-yl)-1,3-thiazol-2-amine, |
| 193 | N,N-diethyl-N'-[4-(2-methylimidazo[1,2-a]pyridin-3-yl)-1,3-thiazol-2-yl]benzene-1,4-diamine, |

-continued

| Cpd | Name |
|---|---|
| 194 | N-(4-{[4-(2-methylimidazo[1,2-a]pyridin-3-yl)-1,3-thiazol-2-yl]amino}phenyl)acetamide, |
| 195 | N-(1,3-benzodioxol-5-yl)-4-[2-(trifluoromethyl)imidazo[1,2-a]pyridin-3-yl]-1,3-thiazol-2-amine, |
| 196 | 4-{[4-(2-methylimidazo[1,2-a]pyridin-3-yl)pyrimidin-2-yl]amino}benzoic acid, |
| 197 | N-(4-bromophenyl)-4-(2-methylimidazo[1,2-a]pyridin-3-yl)-1,3-thiazol-2-amine, |
| 198 | N-(3,4-dichlorophenyl)-4-(2-methylimidazo[1,2-a]pyridin-3-yl)-1,3-thiazol-2-amine, |
| 199 | N-(4-chlorophenyl)-4-(2-methylimidazo[1,2-a]pyridin-3-yl)-1,3-thiazol-2-amine, |
| 200 | N-(4-bromo-2-chlorophenyl)-4-(2-methylimidazo[1,2-a]pyridin-3-yl)-1,3-thiazol-2-amine, |
| 201 | 4-{[4-(2-methylimidazo[1,2-a]pyridin-3-yl)-1,3-thiazol-2-yl]amino}benzene-1,2-diol, |
| 202 | N-(3,4-dimethoxyphenyl)-4-(2-methylimidazo[1,2-a]pyridin-3-yl)-1,3-thiazol-2-amine, |
| 203 | N-(2,4-difluorophenyl)-4-(2-methylimidazo[1,2-a]pyridin-3-yl)-1,3-thiazol-2-amine, |
| 204 | N-(4-ethoxyphenyl)-4-(2-methylimidazo[1,2-a]pyridin-3-yl)-1,3-thiazol-2-amine, |
| 205 | N-(2-bromo-4-methylphenyl)-4-(6-chloro-2-methylimidazo[1,2-a]pyridin-3-yl)-1,3-thiazol-2-amine, |
| 206 | N'-[4-(6-chloro-2-methylimidazo[1,2-a]pyridin-3-yl)-1,3-thiazol-2-yl]-N,N-diethylbenzene-1,4-diamine, |
| 207 | 4-(6-chloro-2-methylimidazo[1,2-a]pyridin-3-yl)-N-(3,4-dimethoxyphenyl)-1,3-thiazol-2-amine, |
| 208 | N-(2-bromo-4-methoxyphenyl)-4-(6-chloro-2-methylimidazo[1,2-a]pyridin-3-yl)-1,3-thiazol-2-amine, |
| 209 | 4-(6-chloro-2-methylimidazo[1,2-a]pyridin-3-yl)-N-(3-methylphenyl)-1,3-thiazol-2-amine, |
| 210 | 3-{[4-(6-chloro-2-methylimidazo[1,2-a]pyridin-3-yl)-1,3-thiazol-2-yl]amino}phenol, |
| 211 | 1-(3-{[4-(6-chloro-2-methylimidazo[1,2-a]pyridin-3-yl)-1,3-thiazol-2-yl]amino}phenyl)ethanone, |
| 212 | N-(3-bromophenyl)-4-(6-chloro-2-methylimidazo[1,2-a]pyridin-3-yl)-1,3-thiazol-2-amine, |
| 213 | 4-(6-chloro-2-methylimidazo[1,2-a]pyridin-3-yl)-N-(3-chlorophenyl)-1,3-thiazol-2-amine, |
| 214 | 4-(6-chloro-2-methylimidazo[1,2-a]pyridin-3-yl)-N-(2,4-dimethylphenyl)-1,3-thiazol-2-amine, |
| 215 | 4-(6-chloro-2-methylimidazo[1,2-a]pyridin-3-yl)-N-(3-fluorophenyl)-1,3-thiazol-2-amine, |
| 216 | N-(4-bromo-2-methylphenyl)-4-(6-chloro-2-methylimidazo[1,2-a]pyridin-3-yl)-1,3-thiazol-2-amine, |
| 217 | 4-(6-chloro-2-methylimidazo[1,2-a]pyridin-3-yl)-N-(3-methoxyphenyl)-1,3-thiazol-2-amine, |
| 218 | 4-(6-chloro-2-methylimidazo[1,2-a]pyridin-3-yl)-N-(2,4-dichlorophenyl)-1,3-thiazol-2-amine, |
| 219 | 4-(6-chloro-2-methylimidazo[1,2-a]pyridin-3-yl)-N-(2,2-dimethyl-1,3-benzodioxol-5-yl)-1,3-thiazol-2-amine, |
| 220 | N-(1,3-benzodioxol-5-yl)-4-(6,8-dichloro-2-methylimidazo[1,2-a]pyridin-3-yl)-1,3-thiazol-2-amine, |
| 221 | N'-[4-(2,8-dimethylimidazo[1,2-a]pyridin-3-yl)-1,3-thiazol-2-yl]-N,N-dimethylbenzene-1,4-diamine, |
| 222 | 4-(2,8-dimethylimidazo[1,2-a]pyridin-3-yl)-N-(4-methoxyphenyl)-1,3-thiazol-2-amine, |
| 223 | 4-(2,8-dimethylimidazo[1,2-a]pyridin-3-yl)-N-(4-methylphenyl)-1,3-thiazol-2-amine, |
| 224 | N-(4-chlorophenyl)-4-(2,8-dimethylimidazo[1,2-a]pyridin-3-yl)-1,3-thiazol-2-amine, |
| 225 | 4-(2,8-dimethylimidazo[1,2-a]pyridin-3-yl)-N-(3-methoxyphenyl)-1,3-thiazol-2-amine, |
| 226 | N-(1,3-benzodioxol-5-yl)-4-(2,8-dimethylimidazo[1,2-a]pyridin-3-yl)-1,3-thiazol-2-amine, |
| 227 | N'-[4-(8-bromo-2-methylimidazo[1,2-a]pyridin-3-yl)-1,3-thiazol-2-yl]-N,N-dimethylbenzene-1,4-diamine, |
| 228 | 4-(8-bromo-2-methylimidazo[1,2-a]pyridin-3-yl)-N-(4-methoxyphenyl)-1,3-thiazol-2-amine, |
| 229 | 4-(8-bromo-2-methylimidazo[1,2-a]pyridin-3-yl)-N-(4-methylphenyl)-1,3-thiazol-2-amine, |
| 230 | 4-(8-bromo-2-methylimidazo[1,2-a]pyridin-3-yl)-N-(4-chlorophenyl)-1,3-thiazol-2-amine, |
| 231 | 4-(8-bromo-2-methylimidazo[1,2-a]pyridin-3-yl)-N-phenyl-1,3-thiazol-2-amine, |
| 232 | 4-(8-bromo-2-methylimidazo[1,2-a]pyridin-3-yl)-N-(3-methoxyphenyl)-1,3-thiazol-2-amine, |
| 233 | 4-(8-bromo-2-methylimidazo[1,2-a]pyridin-3-yl)-N-(2-chlorophenyl)-1,3-thiazol-2-amine, |
| 234 | 4-(8-bromo-2-methylimidazo[1,2-a]pyridin-3-yl)-N-(2-methoxyphenyl)-1,3-thiazol-2-amine, |
| 235 | N-(1,3-benzodioxol-5-yl)-4-(8-bromo-2-methylimidazo[1,2-a]pyridin-3-yl)-1,3-thiazol-2-amine, |
| 236 | 4-(6-fluoro-2-methylimidazo[1,2-a]pyridin-3-yl)-N-(3-methoxyphenyl)-1,3-thiazol-2-amine, |
| 237 | 4-(6-fluoro-2-methylimidazo[1,2-a]pyridin-3-yl)-N-(4-methylphenyl)-1,3-thiazol-2-amine, |
| 238 | 1-(3-{[4-(6-fluoro-2-methylimidazo[1,2-a]pyridin-3-yl)-1,3-thiazol-2-yl]amino}phenyl)ethanone, |
| 239 | N-(2,6-dibromophenyl)-4-(6-fluoro-2-methylimidazo[1,2-a]pyridin-3-yl)-1,3-thiazol-2-amine, |

-continued

| Cpd | Name |
|---|---|
| 240 | 4-(7-chloro-2-methylimidazo[1,2-a]pyridin-3-yl)-N-(4-chlorophenyl)-1,3-thiazol-2-amine, |
| 241 | 4-(7-chloro-2-methylimidazo[1,2-a]pyridin-3-yl)-N-(4-methoxyphenyl)-1,3-thiazol-2-amine, |
| 242 | N'-[4-(7-chloro-2-methylimidazo[1,2-a]pyridin-3-yl)-1,3-thiazol-2-yl]-N,N-dimethylbenzene-1,4-diamine, |
| 243 | 4-(7-chloro-2-methylimidazo[1,2-a]pyridin-3-yl)-N-(4-methylphenyl)-1,3-thiazol-2-amine, |
| 244 | 1-(4-{[4-(7-chloro-2-methylimidazo[1,2-a]pyridin-3-yl)-1,3-thiazol-2-yl]amino}phenyl)ethanone, |
| 245 | 4-(imidazo[1,2-a]pyridin-3-yl)-N-(4-methoxyphenyl)pyrimidin-2-amine, |
| 246 | N-(3-chlorophenyl)-4-(imidazo[1,2-a]pyridin-3-yl)pyrimidin-2-amine, |
| 247 | N-(2-chlorophenyl)-4-(imidazo[1,2-a]pyridin-3-yl)pyrimidin-2-amine, |
| 248 | N-(4-fluorophenyl)-4-(imidazo[1,2-a]pyridin-3-yl)pyrimidin-2-amine, |
| 249 | N-(2,6-dibromo-4-methoxyphenyl)-4-(imidazo[1,2-a]pyridin-3-yl)pyrimidin-2-amine, |
| 250 | 1-(4-{[4-(imidazo[1,2-a]pyridin-3-yl)pyrimidin-2-yl]amino}phenyl)ethanone, |
| 251 | N-(1,3-benzodioxol-5-yl)-4-(imidazo[1,2-a]pyridin-3-yl)pyrimidin-2-amine, |
| 252 | N-(4-ethoxyphenyl)-4-(imidazo[1,2-a]pyridin-3-yl)pyrimidin-2-amine, |
| 253 | N,N-diethyl-N'-[4-(imidazo[1,2-a]pyridin-3-yl)pyrimidin-2-yl]benzene-1,4-diamine, |
| 254 | N'-[4-(imidazo[1,2-a]pyridin-3-yl)pyrimidin-2-yl]-N,N-dimethylbenzene-1,4-diamine, |
| 255 | N-(3-fluorophenyl)-4-(imidazo[1,2-a]pyridin-3-yl)pyrimidin-2-amine, |
| 256 | N-(3-bromophenyl)-4-(imidazo[1,2-a]pyridin-3-yl)pyrimidin-2-amine, |
| 257 | N-(2,6-dibromo-4-methoxyphenyl)-4-(imidazo[1,2-a]pyrimidin-3-yl)pyrimidin-2-amine, |
| 258 | 1-(4-{[4-(imidazo[1,2-a]pyrimidin-3-yl)pyrimidin-2-yl]amino}phenyl)ethanone, |
| 259 | N-(1,3-benzodioxol-5-yl)-4-(imidazo[1,2-a]pyrimidin-3-yl)pyrimidin-2-amine, |
| 260 | 4-(imidazo[1,2-a]pyrimidin-3-yl)-N-(3-methoxyphenyl)pyrimidin-2-amine, |
| 261 | 4-(imidazo[1,2-a]pyrimidin-3-yl)-N-(4-methoxyphenyl)pyrimidin-2-amine, |
| 262 | N-(4-ethoxyphenyl)-4-(imidazo[1,2-a]pyrimidin-3-yl)pyrimidin-2-amine, |
| 263 | N,N-diethyl-N'-[4-(imidazo[1,2-a]pyrimidin-3-yl)pyrimidin-2-yl]benzene-1,4-diamine, |
| 264 | N'-[4-(imidazo[1,2-a]pyrimidin-3-yl)pyrimidin-2-yl]-N,N-dimethylbenzene-1,3-diamine, |
| 265 | N'-[4-(imidazo[1,2-a]pyrimidin-3-yl)pyrimidin-2-yl]-N,N-dimethylbenzene-1,4-diamine, |
| 266 | N-(2-fluorophenyl)-4-(imidazo[1,2-a]pyrimidin-3-yl)pyrimidin-2-amine, |
| 267 | N-(3-fluorophenyl)-4-(imidazo[1,2-a]pyrimidin-3-yl)pyrimidin-2-amine, |
| 268 | N-(4-fluorophenyl)-4-(imidazo[1,2-a]pyrimidin-3-yl)pyrimidin-2-amine, |
| 269 | N-(3-chlorophenyl)-4-(imidazo[1,2-a]pyrimidin-3-yl)pyrimidin-2-amine, |
| 270 | N-(4-bromophenyl)-4-(imidazo[1,2-a]pyrimidin-3-yl)pyrimidin-2-amine, |
| 271 | N-(4-bromophenyl)-4-(2-ethylimidazo[1,2-a]pyrimidin-3-yl)pyrimidin-2-amine. |

Compounds 1 to 18, shown and listed in the above embodiments, are commercially available and have been excluded from the scope of the Compound of Formula (I).

and are useful in a method for treating cancer in a subject in need thereof.

Chemical Definitions

As used herein, the term "$C_{1-8}$alcyl" generally refers to saturated hydrocarbon radicals having from one to eight carbon atoms in a straight or branched chain configuration, including methyl, ethyl, n-propyl, isopropyl, n-butyl, isobutyl, sec-butyl, tert-butyl, n-pentyl, n-hexyl, n-heptyl, n-octyl and the like. In some embodiments, $C_{1-8}$alkyl includes $C_{1-6}$alkyl, $C_{1-4}$alkyl and the like. A $C_{1-8}$alkyl radical may be optionally substituted where allowed by available valences.

As used herein, the term "$C_{2-8}$alkenyl" generally refers to partially unsaturated hydrocarbon radicals having from two to eight carbon atoms in a straight or branched chain configuration and one or more carbon-carbon double bonds therein, including ethenyl, allyl, propenyl and the like. In some embodiments, $C_{2-8}$alkenyl includes $C_{2-6}$alkenyl, $C_{2-4}$alkenyl and the like. A $C_{2-8}$alkenyl radical may be optionally substituted where allowed by available valences.

As used herein, the term "$C_{2-8}$alkynyl" generally refers to partially unsaturated hydrocarbon radicals having from two to eight carbon atoms in a straight or branched chain configuration and one or more carbon-carbon triple bonds therein, including ethynyl, propynyl and the like. In some embodiments, $C_{2-8}$alkynyl includes $C_{2-6}$alkynyl, $C_{2-4}$alkynyl and the like. A $C_{2-8}$alkynyl radical may be optionally substituted where allowed by available valences.

As used herein, the term "$C_{1-8}$alkoxy" generally refers to saturated hydrocarbon radicals of from one to eight carbon atoms having a straight or branched chain configuration of the formula: —O—$C_{1-8}$alkyl, including methoxy, ethoxy, n-propoxy, isopropoxy, n-butoxy, isobutoxy, sec-butoxy, tert-butoxy, n-pentoxy, n-hexoxy and the like. In some embodiments, $C_{1-8}$alkoxy includes $C_{1-6}$alkoxy, $C_{1-4}$alkoxy and the like. A $C_{1-8}$alkoxy radical may be optionally substituted where allowed by available valences.

As used herein, the term "$C_{3-14}$cycloalkyl" generally refers to a saturated monocyclic, bicyclic or polycyclic hydrocarbon radical, including cyclopropyl, cyclobutyl, cyclopentyl, cyclohexyl, cycloheptyl, cyclooctyl, 1H-indanyl, indenyl, tetrahydro-naphthalenyl and the like. In some embodiments, $C_{3-14}$cycloalkyl includes $C_{3-8}$cycloalkyl, $C_{5-8}$cycloalkyl, $C_{3-10}$cycloalkyl and the like. A $C_{3-14}$cycloalkyl radical may be optionally substituted where allowed by available valences.

As used herein, the term "aryl" generally refers to a monocyclic, bicyclic or polycyclic aromatic carbon atom ring structure radical, including phenyl, naphthyl, anthracenyl, fluorenyl, azulenyl, phenanthrenyl and the like. An aryl radical may be optionally substituted where allowed by available valences.

As used herein, the term "heteroaryl" generally refers to a monocyclic, bicyclic or polycyclic aromatic carbon atom ring structure radical in which one or more carbon atom ring members have been replaced, where allowed by structural stability, with one or more heteroatoms, such as an O, S or N atom, including furanyl, thienyl (or thiophenyl), 2H-pyrrolyl, 3H-pyrrolyl, pyrazolyl, imidazolyl, isoxazolyl, isothiazolyl, oxazolyl, thiazolyl, triazolyl, oxadiazolyl, thiadiazolyl, tetrazolyl, pyranyl, thiopyranyl, pyridinyl, pyrimidinyl, pyrazinyl, pyridazinyl, triazinyl, indole, azaindolyl, indazolyl, azaindazolyl, isoindolyl, benzofuranyl, benzothienyl, benzimidazolyl, benzoxazolyl, imidazo[1,2-a]pyridinyl, imidazo[1,2-a]pyrimidinyl, purinyl, quinolinyl, isoquinolinyl, quinazolinyl, quinoxalinyl, 1,3-diazinyl, 1,2-diazinyl, 1,2-diazolyl, 1,4-diazanaphthalenyl, acridinyl and the like and associated homologs thereof. A heteroaryl radical may be optionally substituted on a carbon or nitrogen atom ring member where allowed by available valences.

As used herein, the term "heterocyclyl" generally refers to a saturated or partially unsaturated monocyclic, bicyclic or polycyclic carbon atom ring structure radical in which one or more carbon atom ring members have been replaced, where allowed by structural stability, with a heteroatom, such as an O, S or N atom, including oxiranyl, oxetanyl, azetidinyl, dihydrofuranyl, tetrahydrofuranyl, dihydrothienyl, tetrahydrothienyl, pyrrolinyl, pyrrolidinyl, dihydropyrazolyl, pyrazolinyl, pyrazolidinyl, dihydroimidazolyl, imidazolinyl, imidazolidinyl, isoxazolinyl, isoxazolidinyl, isothiazolinyl, isothiazolidinyl, oxazolinyl, oxazolidinyl, thiazolinyl, thiazolidinyl, triazolinyl, triazolidinyl, oxadiazolinyl, oxadiazolidinyl, thiadiazolinyl, thiadiazolidinyl, tetrazolinyl, tetrazolidinyl, dihydro-2H-pyranyl, tetrahydro-2H-pyranyl, tetrahydro-thiopyranyl, dihydro-pyridinyl, tetrahydro-pyridinyl, hexahydro-pyridinyl, dihydro-pyrimidinyl, tetrahydro-pyrimidinyl, dihydro-pyrazinyl, tetrahydro-pyrazinyl, dihydro-pyridazinyl, tetrahydro-pyridazinyl, piperazinyl, piperidinyl, morpholinyl, thiomorpholinyl, dihydro-triazinyl, tetrahydro-triazinyl, hexahydro-triazinyl, dihydro-indole, tetrahydro-indole, dihydro-indazolyl, tetrahydro-indazolyl, dihydro-isoindolyl, tetrahydro-isoindolyl, dihydro-benzofuranyl, tetrahydro-benzofuranyl, dihydro-benzothienyl, tetrahydro-benzothienyl, dihydro-benzimidazolyl, tetrahydro-benzimidazolyl, dihydro-benzoxazolyl, tetrahydro-benzoxazolyl, benzo[1,3]dioxolyl, benzo[1,4]dioxanyl, dihydro-purinyl, tetrahydro-purinyl, dihydro-quinolinyl, tetrahydro-quinolinyl, dihydro-isoquinolinyl, tetrahydro-isoquinolinyl, dihydro-quinazolinyl, tetrahydro-quinazolinyl, dihydro-quinoxalinyl, tetrahydro-quinoxalinyl and the like and associated homologs thereof. A heterocyclyl radical may be optionally substituted on a carbon or nitrogen atom ring member where allowed by available valences.

As used herein, the term "$C_{1-8}$alkoxy-$C_{1-8}$alkoxy" refers to a radical of the formula: —O—$C_{1-8}$alkyl-O—$C_{1-8}$alkyl. For example, the term "methoxy-ethoxy" refers to a radical of the formula: —O-Et-O-Me.

As used herein, the term "$C_{1-8}$alkoxy-$C_{1-8}$alkoxy-$C_{1-8}$alkoxy" refers to a radical of the formula: —O—$C_{1-8}$alkyl-O—$C_{1-8}$alkyl-O—$C_{1-8}$alkyl.

As used herein, the term "$C_{1-8}$alkoxy-$C_{1-8}$alkyl" refers to a radical of the formula: —$C_{1-8}$alkyl-O—$C_{1-8}$alkyl.

As used herein, the term "$C_{1-8}$alkoxy-carbonyl-amino" refers to a radical of the formula: —NH—C(O)—$C_{1-8}$alkoxy.

As used herein, the term "$C_{1-8}$alkoxy-carbonyl" refers to a radical of the formula: —C(O)—O—$C_{1-8}$alkyl.

As used herein, the term "$C_{1-8}$alkyl-amino" refers to a radical of the formula: —NH—$C_{1-8}$alkyl or —N($C_{1-8}$alkyl)$_2$.

As used herein, the term "$C_{1-8}$alkyl-amino-$C_{1-8}$alkyl" refers to a radical of the formula: —$C_{1-8}$alkyl-NH—$C_{1-8}$alkyl or —$C_{1-8}$alkyl-N($C_{1-8}$alkyl)$_2$.

As used herein, the term "$C_{1-8}$alkyl-aminosulfonyl" refers to a radical of the formula: —$SO_2$—NH—$C_{1-8}$alkyl or —$SO_2$—N($C_{1-8}$alkyl)$_2$.

As used herein, the term "$C_{1-8}$alkyl-carbonyl" refers to a radical of the formula: —C(O)—$C_{1-8}$alkyl.

As used herein, the term "$C_{1-8}$alkyl-carbonyl-amino" refers to a radical of the formula: —NH—C(O)—$C_{1-8}$alkyl.

For example, the term "methyl-carbonyl-amino" refers to a radical of the formula: —NH—C(O)-Me.

As used herein, the term "amino" refers to a radical of the formula: —$NH_2$.

As used herein, the term "amino-$C_{1-8}$alkyl" refers to a radical of the formula: —$C_{1-8}$alkyl-$NH_2$.

As used herein, the term "aminosulfonyl" refers to a radical of the formula: —$SO_2$—$NH_2$.

As used herein, the term "carbonyl" refers to a radical of the formula: —C(O)—.

As used herein, the term "carboxy" refers to a radical of the formula: —COOH or —$CO_2$H.

As used herein, the term "halo" or "halogen" generally refers to a halogen atom radical, including fluoro, chloro, bromo and iodo.

As used herein, the term "halo-$C_{1-8}$alkoxy" refers to a radical of the formula: —O—$C_{1-8}$alkyl-halo, wherein $C_{1-8}$alkyl may be partially or completely substituted where allowed by available valences with one or more halogen atoms, including difluoromethoxy, trifluoromethoxy, difluoroethoxy or trifluoroethoxy and the like. In some embodiments, halo-$C_{1-8}$alkoxy includes halo-$C_{1-6}$alkoxy, halo-$C_{1-4}$alkoxy and the like.

As used herein, the term "halo-$C_{1-8}$alkyl" refers to a radical of the formula: —$C_{1-8}$alkyl-halo, wherein $C_{1-8}$alkyl may be partially or completely substituted where allowed by available valences with one or more halogen atoms, including difluoromethyl, trifluoromethyl, difluoroethyl or trifluoroethyl and the like. In some embodiments, halo-$C_{1-8}$alkyl includes halo-$C_{1-6}$alkyl, halo-$C_{1-4}$alkyl and the like.

As used herein, the term "hydroxy-$C_{1-8}$alkyl" refers to a radical of the formula: —$C_{1-8}$alkyl-hydroxy, wherein $C_{1-8}$alkyl may be partially or completely substituted where allowed by available valences with one or more hydroxy radicals.

For the purposes of the compounds described herein, where one or more functionalities encompassing substituent variables for a compound of Formula (I) are incorporated into a compound of Formula (I), each functionality appearing at any location within the disclosed compound may be independently selected, and as appropriate, independently and/or optionally substituted.

As used herein, the term "substituent" means positional variables on the atoms of a core molecule that are known to those skilled in the art to be chemical moieties that are appropriate for substitution at a designated atom position, replacing one or more hydrogens on the designated atom with a selection from the indicated group, provided that the designated atom's normal valency under the existing circumstances is not exceeded, and that the substitution results in a stable compound. Combinations of substituents and/or variables are permissible only if such combinations result in stable compounds. It should also be noted that any carbon as well as heteroatom with unsatisfied valences as described or shown herein is assumed to have a sufficient number of hydrogen atom(s) to satisfy the valences described or shown.

As used herein, the term "dependently selected from" refers to substituent variables for Formula (I) or another structural formulae as described herein, which are intended to have a dependent pattern of substitution at each occurrence.

As used herein, the terms "independently selected," or "each selected from", and variations thereof, mean that, when any substituent occurs more than once in a substituent list or as a portion of a substituent in the list for Formula (I) or another structural formulae as described herein, the pattern of substitution on any particular substituent at each occurrence is independent of the pattern at any other occurrence. Further, the use of a generic substituent variable on any formula or structure position for a compound as described herein is understood to include the replacement of the generic substituent with species substituents that are included within the particular genus, e.g., aryl may be replaced with phenyl or naphthalenyl and the like, and that the resulting compound is to be included within the scope of the compounds as described herein.

As used herein, the term "optionally substituted" means optional substitution with the specified groups, radicals or moieties.

As used herein, the terms "stable compound" or "stable structure" mean a compound that is sufficiently robust to survive isolation to a useful degree of purity from a reaction mixture and formulations thereof into an efficacious therapeutic agent.

Compound names used herein were obtained using the Autonom batch naming feature of ChemDraw Ultra Version 10.0.4, provided by CambridgeSoft. When the compound name disclosed herein conflicts with the structure as described, the structure description will supercede the use of the name to define the compound intended.

Pharmaceutical Forms

As used herein, the term "form" means a compound of Formula (I), Formula (Ia) or Formula (Ib) isolated for use as selected from a free acid, free base, salt, ester, hydrate, solvate, chelate, clathrate, isotopologue, geometric isomer, stereoisomer, racemate, enantiomer, diastereomer, tautomer or polymorph thereof. In certain embodiments, the form of the compound of Formula (I) is pharmaceutically acceptable. Prodrugs of the compounds as described herein are also contemplated.

As used herein, the term "isolated" means the physical state of a compound of Formula (I), Formula (Ia) or Formula (Ib) after being isolated and/or purified from a synthetic process (e.g., from a reaction mixture) or natural source or combination thereof according to an isolation or purification process or processes described herein or which are well known to the skilled artisan (e.g., chromatography, recrystallization and the like) in sufficient purity to be characterizable by standard analytical techniques described herein or well known to the skilled artisan.

As used herein, the term "protected" means that a functional group in a compound of Formula (I) is in a form modified to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

As used herein, the term "prodrug" means a compound (e.g., a drug precursor) that is transformed in vivo to yield an active compound of Formula (I) or a pharmaceutically acceptable salt, hydrate or solvate of the compound. The transformation may occur by various mechanisms (e.g., by metabolic or chemical processes), such as, for example, through hydrolysis in the blood. In one example, when a compound of Formula (I) or a form thereof contains a carboxylic acid functional group, a prodrug can comprise an ester formed by the replacement of the hydrogen atom of the acid group with a group such as a functional carbonyl group and the like. In another example, when a compound of Formula (I) or a form thereof contains an alcohol functional group, a prodrug can be formed by the replacement of the hydrogen atom of the alcohol group with a functional carbonyl or carbonyloxy group and the like. In another example, when a compound of Formula (I) or a form thereof contains an amine functional group, a prodrug can be formed by the replacement of a hydrogen atom in the amine group with a functional carbonyl group.

As used herein, the term "solvate" means a physical association of a compound as described herein with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. As used herein, "solvate" encompasses both solution-phase and isolatable solvates. One or more compounds as described herein may exist in unsolvated as well as solvated forms with pharmaceutically acceptable solvents such as water, ethanol, and the like, and it is intended that the scope of the compounds described herein embrace both solvated and unsolvated forms. Non-limiting examples of suitable solvates include ethanolates, methanolates, and the like. One or more compounds as described herein may optionally be converted to a solvate. Preparation of solvates is generally known.

As used herein, the term "hydrate" means a solvate wherein the solvent molecule is water.

The compounds of Formula (I) can form salts which are also described and presented herein. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein.

As used herein, the term "pharmaceutically acceptable salt" refers to any non-toxic salt that, upon administration to a recipient, individual, subject or patient, is capable of providing, either directly or indirectly, a compound as described herein. Salts of the compounds of the Formula (I) may be formed, for example, by reacting a compound of Formula (I) with an amount of acid or base, such as an equivalent amount, in a medium such as one in which the salt precipitates or in an aqueous medium followed by lyophilization.

As used herein, the term "pharmaceutically acceptable" refers to a component that is, within the scope of sound medical judgment, suitable for use in contact with the tissues of humans and other mammals without undue toxicity, irritation, allergic response and the like, and are commensurate with a reasonable benefit/risk ratio.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates), trifluoroacetates and the like.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and the like.

All such acid salts and base salts are intended to be pharmaceutically acceptable salts as described herein and all acid and base salts are considered equivalent to the free forms of the corresponding compounds.

Pharmaceutically acceptable esters of the present compounds include the following groups: carboxylic acid esters, sulfonate esters, amino acid esters, phosphonate esters such as mono-, di- or triphosphate esters and the like.

Compounds of Formula (I) or a salt, solvate, ester or prodrug thereof, may further exist in a tautomeric form. All such tautomeric forms are intended to be included as described herein.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, be included as described herein.

The compounds described herein may include one or more chiral centers, and as such may exist as racemic mixtures (R/S) or as substantially pure enantiomers and diastereomers. The compounds may also exist as substantially pure (R) or (S) enantiomers (when one chiral center is present). In one embodiment, the compounds described herein are (S) isomers and may exist as enantiomerically pure compositions substantially comprising only the (S) isomer. In another embodiment, the compounds described herein are (R) isomers and may exist as enantiomerically pure compositions substantially comprising only the (R) isomer. As one of skill in the art will recognize, when more than one chiral center is present, the compounds described herein may also exist as a (R,R), (R,S), (S,R) or (S,S) isomer, as defined by IUPAC Nomenclature Recommendations.

As used herein, the term "substantially pure" refers to compounds consisting substantially of a single isomer in an amount greater than or equal to 90%, in an amount greater than or equal to 92%, in an amount greater than or equal to 95%, in an amount greater than or equal to 98%, in an amount greater than or equal to 99%, or in an amount equal to 100% of the single isomer.

As used herein, a "racemate" is any mixture of isometric forms that are not "enantiomerically pure", including mixtures such as, without limitation, in a ratio of about 50/50, about 60/40, about 70/30, or about 80/20.

In addition, the compounds described herein embrace all geometric and positional isomers. For example, if a compound of Formula (I) incorporates a double bond or a fused ring, both the cis- and trans-forms, as well as mixtures, are embraced within the scope of the compounds described herein. Diastereomeric mixtures can be separated into their individual diastereomers on the basis of their physical chemical differences by methods well known to those skilled in the art, such as, for example, by chromatography and/or fractional crystallization. Enantiomers can also be separated by use of chiral HPLC column or other chromatographic methods known to those skilled in the art.

Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers.

Also, some of the compounds of Formula (I) may be atropisomers (e.g., substituted biaryls or biheteroaryls) and are considered to be included in the scope of the compounds described herein.

It is also possible that the compounds of Formula (I) may exist in different tautomeric forms, and all such forms are embraced within the scope of the compounds described herein, such as, for example, an amide or imino ether. Accordingly, all keto-enol and imine-enamine forms of the compounds are included in the compounds described herein.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of the compounds described herein, as are positional isomers (such as, for example, 4-pyridyl and 3-pyridyl). For example, if a compound of Formula (I) incorporates a double bond or a fused ring, both the cis- and trans-forms, as well as mixtures, are embraced within the scope of the compounds described herein. Also, for example, all keto-enol and imine-enamine forms of the compounds are included in the compounds described herein. Individual stereoisomers of the compounds described herein may, for example, be substantially free of other isomers, or may be admixed, for example, as racemates or with all other, or other selected, stereoisomers.

As used herein, the terms "salt", "solvate", "ester", "prodrug" and the like, are intended to equally apply to the salt, solvate, ester and prodrug of enantiomers, stereoisomers, rotamers, tautomers, positional isomers, racemates or prodrugs of the inventive compounds.

As used herein, the term "isotopologue" refers to isotopically-labelled compounds described herein which are identical to those recited herein, but for the fact that one or more atoms are replaced by an atom having an atomic mass or mass number different from the atomic mass or mass number usually found in nature. Examples of isotopes that can be incorporated into compounds described herein include isotopes of hydrogen, carbon, nitrogen, oxygen, phosphorus, fluorine and chlorine, $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. As the result of isotope substitution, certain isotopologues of instant compounds may contain an asymmetric carbon atom and can thereby exist as either individual enantiomers, diastereomers or mixtures thereof. Accordingly, an isotopologue may include racemic mixtures or mixtures of individual respective stereoisomers that are substantially free from another possible stereoisomer.

Certain isotopically-labelled compounds of Formula (I) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with an isotope such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

Polymorphic crystalline and amorphous forms of the compounds of Formula (I), and of the salts, solvates, esters and prodrugs of the compounds of Formula (I), are further intended to be included in the scope of the compounds described herein.

Methods of Treatment

The Bmi-1 oncogene was first identified as part of a key insertion/activation region of the Moloney murine leukemia virus in the early 1990's (1-6). The Bmi-1 gene is a member of the Polycomb group (PcG) of transcriptional repressors and was identified as a necessary regulator of hematopoietic stem cell (HSC) self-renewal (76, 77). Park found that Bmi-1 is highly expressed in purified mouse and human HSCs and that the absence of Bmi-1, as demonstrated by Bmi-1 knockout mice, results in the progressive loss of all hematopoietic lineages (76). Furthermore, the transplantation of Bmi-1$^{-/-}$ day 14.5 fetal liver cells into lethally irradiated normal mice, demonstrated that the cells were unable to reconstitute myeloid cells, B cells, and T cells because Bmi-1$^{-/-}$ HSCs were unable to renew (76).

In addition to the role of Bmi-1 in HSC self renewal, it was found that Bmi-1 transgene expression induced lymphoma in mice (2). Bmi-1 overexpression was also found in many tumor types, including acute myeloid leukemia, medulloblastoma, neuroblastoma, colorectal cancer, lung cancer, and prostate cancer, and was found to increase with malignancy (34, 78, 61, 79, 80, 65, 43). Loss of Bmi-1 in various cancerous human cell lines via Bmi-1 specific RNA interference (RNAi) was shown to lead to acute cell death and growth inhibition, whereas loss of Bmi-1 in various normal cell lines was shown to lead to only moderate growth inhibition and not significant cell death (69). Thus, Bmi-1 is necessary for the survival of cancer cells but has minimal effect on the survival of normal cells.

Bmi-1 has been subsequently shown to act as an oncogene experimentally and has proven particularly potent in conjunction with c-myc to initiate lymphoma in murine models (7, 8). The role of Bmi-1 in lymphomagenesis has been attributed partially to transcriptional repression of the INK4A locus (containing both the p16$^{INK4A}$ and p14$^{ARF}$ genes) leading to maintenance of proliferation and prevention of differentiation (7, 9). Loss of expression of the INK4A locus due to promoter silencing has been heavily studied and is both important for progression and prognostic for many types of hematologic cancers (10, 11). The INK4A locus is occasionally lost by deletion in leukemia and lymphoma (12, 13).

However, Bmi-1 has been shown to play a role in tumorigenesis in models lacking the INK4A locus, indicating that other loci important in cancer are regulated by this protein (14). Experimental results have further demonstrated that loss of Bmi-1 protein induces growth arrest and senescence in fibrosarcoma cells known to lack INK4A (15). There is also evidence that Bmi-1 is important for the hedgehog (Hh) pathway in breast cancer. Activation of Hh signaling increases Bmi-1 expression, while down-regulation of Bmi-1 (via siRNA) abrogates the effects of Hh signaling on mammosphere formation in vitro and inhibits ductal/alveolar development mice (16). Recent work has also linked Bmi-1 to regulation of Hox gene expression. Knockdown of Bmi-1 caused a global and loci-specific loss of H2A ubiquitination, up-regulation of the HoxC5 gene, and slower cell growth in HeLa cells (17). Another study demonstrated that E2f6 and Bmi-1 cooperate in the regulation of Hox gene expression (particularly Hox C10 and B9), and consequently affect axial skeleton development, but not in the repression of the Ink4a-Arf locus. These findings underscore the significance of the E2F6-Bmi-1 interaction and suggest that the Hox and Ink4a-Arf loci are regulated by somewhat different Bmi-1-dependent mechanisms (18). Other genes regulated by Bmi-1 remain to be identified. Current research, though, suggests that Bmi-1 has different roles in different cell types and/or developmental stages.

Bmi-1 is highly expressed in malignancies such as diffuse large B cell lymphomas (DLBCL), B cell non-Hodgkin lymphoma, Hodgkins lymphoma, acute myeloid leukemia, colorectal carcinoma, liver carcinoma, non-small cell lung cancer, breast carcinoma and medulloblastoma. The study of Bmi-1 knockout mice has revealed that Bmi-1 is required for the self-renewal of both leukemic and normal hematopoietic stem cells.

Additionally, evidence exists linking Bmi-1 expression levels to blood tumor types, particularly Burkett's lymphoma, Burkitt's lymphoma, Mantle Cell Lymphoma, Hodgkins lymphoma (21-23) and non-Hodgkins lymphoma and some T cell lymphomas (2, 24-31) and acute myeloid leukemia and T-ALL (32-35). In Hodgkins lymphoma, Raaphorst et al observed that Reed-Sternberg cells (HRS) co-express Bmi-1, EZH2, and Mib-1/Ki-67. Because IRS cells are thought to originate from Bmi-1 expressing germinal center lymphocytes, which should lose Bmi-1 expression (and gain EZH2) as they differentiate, these observations suggest that Hodgkins disease is associated with aberrant co-expression of Bmi-1 and EZH2 in these cells (22). An assessment of acute myeloid leukemia stem cell populations by van Gosliga et al showed that CD34$^+$/CD38$^-$ cells capable of forming leukemic-cobblestone colonies on a bone marrow substrate through at least two rounds of expansion represented an extreme minority of the cell population. Further analysis showed that this cell population expressed high levels of Bmi-1 mRNA and can establish an aggressive leukemia in mice, while those cells that had lower levels of Bmi-1 could not (36). Such studies implicate Bmi-1 in tumor growth and cell survival and suggest a central function in tumor initiation or maintenance of tumor stem cells.

The expression levels of Bmi-1 have been shown to have prognostic relevance in a number of tumor types. An example of this is found in acute myeloid leukemia in which a study assessing the prognostic value of high Bmi-1 protein expression in 64 patients was conducted (32). On the basis of the median value of Bmi-1 protein expression (54.58%), they divided the patients into two groups and analyzed survival. Patients with lower Bmi-1 positivity (<55%, n=33) had significantly longer overall survival (P=0.0001), relapse-free survival (P=0.0072) and remission duration (P=0.0065) when compared to the patients with higher Bmi-1 (>55%, n=31, respectively), regardless of age group (32). Similarly, Van Galen et al (37) have shown that Bmi-1 expression is highly prognostic in diffuse large B cell lymphomas (DLBCL) (37). Neoplastic cells in DLBCL cases originate from germinal centre B (GCB) cells or their descendents(38). Recent studies based on microarray analysis showed that some DLBCL phenotypically resemble non-neoplastic GCB cells, while some show an expression profile similar to that of activated B cells (ABC) (39).

Furthermore, patients with a GCB-like phenotype have a considerably better prognosis than those with an ABC-like phenotype (40). Bmi-1 was identified as one of the genes that distinguish the ABC-like DLBCL (39),(41). Other groups have linked elevated Bmi-1 expression with poor prognosis in Mantle Cell Lymphoma (MCL), non-Hodgkins lymphoma and other leukemias (22, 26, 27, 29, 42-44) as well as many other tumour types including neuroblastoma, glioblastoma, hepatocellular carcinoma, and breast, colorectal, prostate, lung, gastric and salivary gland cancers (45-57). The loss of expression from the 1NK4A locus has also been shown to have prognostic value (12, 13). Taken together, these data strongly implicate Bmi-1 in cancer and suggest that inhibiting cancer stem cell production and a corresponding reduction in Bmi-1 protein levels, may have a beneficial therapeutic effect in patients with multiple cancer types, particularly in those afflicted with hematological cancers.

For example, MCL is a rare, aggressive and incurable B cell non-Hodgkin's lymphoma that is refractory to conventional chemotherapy and is associated with a poor prognosis. MCL is characterized by the t(11;14) (q13;q32) translocation, resulting in amplification and overexpression of the polycomb group gene BMI-1, which is critical for self-renewal of hematopoietic stem cells and has the capacity to induce tumors when over expressed.

Multiple myeloma is another fatal B-cell malignancy characterized by the accumulation of abnormal plasma cells in the bone marrow. Similar to MCL, standard therapy for multiple myeloma normally consists of combination chemotherapy that often results in a 60-70% response rate. However, most patients will eventually relapse, leaving patients with limited therapeutic options. Recent gene expression profiling of multiple myeloma cells revealed elevated expression of Bmi-1 compared to normal plasma cells, as confirmed by immunoblotting.

Bmi-1 has been shown to be transcriptionally regulated by a number of factors including SALL4, FoxM1, c-Myc, E2F-1 and Mel18. Bmi-1 and SALL4 are putative oncogenes that modulate stem cell pluripotency and play a role in leukemigenesis (also referred to as leukemogenesis). Murine Sall4 also has been shown to play an essential role in maintaining the properties of ES (embryonic stem) cells and governing the fate of the primitive inner cell mass. Yang et al demonstrated that transcription from the Bmi-1 promoter is markedly activated by SALL4 in a dose-dependent manner (35). The Forkhead box transcription factor FoxM1 is expressed in proliferating cells and has been shown to up-regulate Bmi-1 expression in transformed NIH 3T3 cells in response to oxidative stress through c-myc activation (58). The Bmi-1 homologue, Mel18, acts as a potent repressor of Bmi-1 expression. The Bmi-1 promoter region contains a functional E-box through which c-Myc and Mel-18 can regulate Bmi-1 expression. Because Mel-18 down-regulates c-Myc expression and Bmi-1 is a c-Myc target, these data suggest that Mel-18 regulates expression of Bmi-1 via repression of c-Myc during cellular senescence and link c-Myc and polycomb function (59). Similarly, a recent report in neuroblastoma suggests that E2F-1 may also regulate Bmi-1 expression (60). The Bmi-1 promoter contains a putative E2F binding site required for the activation of a Bmi-1 promoter-dependent reporter construct by E2F-1. Post-transcriptional control of Bmi-1 production has not been reported.

However, Applicants have discovered, via analysis of the Bmi-1 untranslated regions (UTRs), that putative regulatory motifs may impart control over protein expression. Applicants have also discovered compounds described herein that may interact with these regions and, thus directly regulate BMI-1 protein production in cancer stem cells and differentiated cancer cells. Additionally certain compounds described herein have demonstrated activation of the apoptotic pathway as determined by annexin-V expression, as well as cleavage of poly(ADP-ribose) polymerase (PARP) and caspase-9 and caspase-7. Cell cycle analyses of cells treated with these compounds have further demonstrated a block at the $G_2$/M phase followed by the development of polyploidy. These findings suggest that Bmi-1 may also play a role in DNA repair and/or regulation of mitosis. Applicants have demonstrated that the compounds described herein may be useful inhibitors of Bmi-1 protein production and potential therapeutics for generally any cancer that expresses BMI-1. Additionally, the inhibitors of BMI-1 expression described herein may be useful in targeting cancer cell populations that have been shown to be resistant to current therapies (i.e. DNA damaging large and small molecule chemotherapeutic agents and radiation therapies, as well as molecular targeted therapies).

As used herein, the italicized form of "Bmi-1," unless otherwise specified or clear from the context of the specification, refers to a Bmi-1 nucleic acid sequence. The nucleic acid sequence may be DNA or RNA. The nonitalicized form of "Bmi-1," unless otherwise specified or clear from the context of the specification, refers to the Bmi-1 protein.

In accordance with the present description, compounds that down-regulate Bmi-1 expression inhibit proliferation of tumor cells in vitro and in vivo. Elevated expression of human Bmi-1 has been reported in multiple cancer samples and cancer cell lines (2, 42, 51, 56, 61-68). Applicants have identified compounds that down-regulate Bmi-1 expression and reduce Bmi-1 protein levels via loss of Bmi-1 analyses in vitro with concurrent inhibition of tumor cell growth and xenograft growth in vivo.

One embodiment described herein is directed to a method for treating cancer in a subject in need thereof comprising contacting a cancer cell in the subject with an effective amount of a compound of Formula (I) as described herein or a form thereof.

Another embodiment described herein is directed to a method for treating cancer in a subject in need thereof comprising administering an effective amount of a compound or a form or composition thereof to the subject, wherein the compound is selected from:

| Cpd | Name |
|---|---|
| 1 | N-(2,6-dibromo-4-methoxyphenyl)-4-(2-methylimidazo[1,2-a]pyrimidin-3-yl)thiazol-2-amine, |
| 2 | N-(3-chloro-2-methylphenyl)-4-(2-methylimidazo[1,2-a]pyrimidin-3-yl)thiazol-2-amine, |
| 3 | N-(2,5-dimethoxyphenyl)-4-(2-methylimidazo[1,2-a]pyrimidin-3-yl)thiazol-2-amine, |
| 4 | N-(2-ethoxyphenyl)-4-(2-methylimidazo[1,2-a]pyrimidin-3-yl)thiazol-2-amine, |
| 5 | N-(2-chlorophenyl)-4-(2-methylimidazo[1,2-a]pyrimidin-3-yl)thiazol-2-amine, |
| 6 | 4-(2-methylimidazo[1,2-a]pyrimidin-3-yl)-N-m-tolylthiazol-2-amine, |
| 7 | N,N-diethyl-N'-(4-(2-methylimidazo[1,2-a]pyrimidin-3-yl)thiazol-2-yl)benzene-1,4-diamine, |
| 8 | N-(2-methoxyphenyl)-4-(2-methylimidazo[1,2-a]pyrimidin-3-yl)thiazol-2-amine, |
| 9 | 1-(3-(4-(2-methylimidazo[1,2-a]pyrimidin-3-yl)thiazol-2-ylamino)phenyl)ethanone, |
| 10 | 4-(4-(2-methylimidazo[1,2-a]pyrimidin-3-yl)thiazol-2-ylamino)benzenesulfonamide, |
| 11 | N-(4-(4-(2-methylimidazo[1,2-a]pyrimidin-3-yl)thiazol-2-ylamino)phenyl)acetamide, |

-continued

| Cpd | Name |
|---|---|
| 12 | N,N-dimethyl-N'-(4-(2-methylimidazo[1,2-a]pyrimidin-3-yl)thiazol-2-yl)benzene-1,4-diamine, |
| 13 | N-(4-ethoxyphenyl)-4-(2-methylimidazo[1,2-a]pyrimidin-3-yl)thiazol-2-amine, |
| 14 | N-(4-methoxyphenyl)-4-(2-methylimidazo[1,2-a]pyrimidin-3-yl)thiazol-2-amine, |
| 15 | 4-(4-(2-methylimidazo[1,2-a]pyrimidin-3-yl)thiazol-2-ylamino)benzoic acid, |
| 16 | 4-(4-(2,7-dimethylimidazo[1,2-a]pyridin-3-yl)thiazol-2-ylamino)phenol, |
| 17 | 4-(2,7-dimethylimidazo[1,2-a]pyridin-3-yl)-N-(4-methoxyphenyl)thiazol-2-amine, |
| 18 | 4-(2,7-dimethylimidazo[1,2-a]pyridin-3-yl)-N-(2-methoxyphenyl)thiazol-2-amine, |
| 19 | N-(2,6-dichloro-4-methoxyphenyl)-4-(2-methylimidazo[1,2-a]pyrimidin-3-yl)thiazol-2-amine, |
| 20 | N-(2,6-difluoro-4-methoxyphenyl)-4-(2-methylimidazo[1,2-a]pyrimidin-3-yl)thiazol-2-amine, |
| 21 | N-(2,6-dibromo-4-methylphenyl)-4-(2-methylimidazo[1,2-a]pyrimidin-3-yl)thiazol-2-amine, |
| 22 | 4-(2-methylimidazo[1,2-a]pyrimidin-3-yl)-N-(2,4,6-tribromophenyl)thiazol-2-amine, |
| 23 | N-(2,6-dibromo-4-(2-methoxyethoxy)phenyl)-4-(2-methylimidazo[1,2-a]pyrimidin-3-yl)thiazol-2-amine, |
| 24 | 4-(6-chloroimidazo[1,2-a]pyridine-3-yl)-N-(2,6-dibromo-4-methoxyphenyl)thiazol-2-amine, |
| 25 | 4-(6-chloroimidazo[1,2-a]pyridine-3-yl)-N-(2,6-dibromo-4-methylphenyl)thiazol-2-amine, |
| 26 | 4-(6-chloroimidazo[1,2-a]pyridine-3-yl)-N-(2,6-dichloro-4-methoxyphenyl)thiazol-2-amine, |
| 27 | 4-(6-chloroimidazo[1,2-a]pyridine-3-yl)-N-(4-methoxy-2,6-dimethylphenyl)thiazol-2-amine, |
| 28 | 4-(imidazo[1,2-a]pyridine-3-yl)-N-(3-methoxyphenyl)pyrimidin-2-amine, |
| 29 | 4-(6-chloro-2-methylimidazo[1,2-a]pyridin-3-yl)-N-(4-iodophenyl)thiazol-2-amine, |
| 30 | N-(benzo[d][1,3]dioxol-5-yl)-4-(6-chloro-2-methylimidazo[1,2-a]pyridin-3-yl)thiazol-2-amine, |
| 31 | 3-{[4-(2,7-dimethylimidazo[1,2-a]pyridin-3-yl)-1,3-thiazol-2-yl]amino}phenol, |
| 32 | 4-(2,7-dimethylimidazo[1,2-a]pyridin-3-yl)-N-(4-methylphenyl)-1,3-thiazol-2-amine, |
| 33 | 1-(4-{[4-(2,7-dimethylimidazo[1,2-a]pyridin-3-yl)-1,3-thiazol-2-yl]amino}phenyl)ethanone, |
| 34 | 1-(4-{[4-(2-methylimidazo[1,2-a]pyrimidin-3-yl)-1,3-thiazol-2-yl]amino}phenyl)ethanone, |
| 35 | 3-{[4-(2-methylimidazo[1,2-a]pyridin-3-yl)-1,3-thiazol-2-yl]amino}phenol, |
| 36 | 4-{[4-(2-methylimidazo[1,2-a]pyridin-3-yl)-1,3-thiazol-2-yl]amino}phenol, |
| 37 | N-(1,3-benzodioxol-5-yl)-4-(2-methylimidazo[1,2-a]pyrimidin-3-yl)-1,3-thiazol-2-amine, |
| 38 | N-(2,6-dichlorophenyl)-4-(2-methylimidazo[1,2-a]pyrimidin-3-yl)-1,3-thiazol-2-amine, |
| 39 | N-(4-iodophenyl)-4-(2-methylimidazo[1,2-a]pyrimidin-3-yl)-1,3-thiazol-2-amine, |
| 40 | N-(1,3-benzodioxol-5-yl)-N-methyl-4-(2-methylimidazo[1,2-a]pyrimidin-3-yl)-1,3-thiazol-2-amine, |
| 41 | N,N-dimethyl-N'-[4-(2-methylimidazo[1,2-a]pyridin-3-yl)-1,3-thiazol-2-yl]benzene-1,4-diamine, |
| 42 | N-(4-methoxyphenyl)-4-(2-methylimidazo[1,2-a]pyrimidin-3-yl)pyrimidin-2-amine, |
| 43 | N,N-dimethyl-N'-[4-(2-methylimidazo[1,2-a]pyrimidin-3-yl)pyrimidin-2-yl]benzene-1,4-diamine, |
| 44 | N-(4-methoxyphenyl)-4-(2-methylimidazo[1,2-a]pyridin-3-yl)-1,3-thiazol-2-amine, |
| 45 | N-(3-fluoro-4-methoxyphenyl)-4-(2-methylimidazo[1,2-a]pyrimidin-3-yl)-1,3-thiazol-2-amine, |
| 46 | N-(3-chloro-4-methoxyphenyl)-4-(2-methylimidazo[1,2-a]pyrimidin-3-yl)-1,3-thiazol-2-amine, |
| 47 | N-(4-methoxyphenyl)-N-methyl-4-(2-methylimidazo[1,2-a]pyrimidin-3-yl)pyrimidin-2-amine, |
| 48 | N-(4-bromophenyl)-4-(2-methylimidazo[1,2-a]pyrimidin-3-yl)-1,3-thiazol-2-amine, |
| 49 | N-(4-chlorophenyl)-4-(2-methylimidazo[1,2-a]pyrimidin-3-yl)-1,3-thiazol-2-amine, |
| 50 | N-(3-chloro-4-methoxyphenyl)-4-(2-Methylimidazo[1,2-a]pyridin-3-yl)-1,3-thiazol-2-amine, |
| 51 | N-(3-fluoro-4-methoxyphenyl)-4-(2-methylimidazo[1,2-a]pyridin-3-yl)-1,3-thiazol-2-amine, |
| 52 | N-[4-(2-methoxyethoxy)phenyl]-4-(2-methylimidazo[1,2-a]pyridin-3-yl)-1,3-thiazol-2-amine, |
| 53 | N-(4-iodophenyl)-4-(2-methylimidazo[1,2-a]pyridin-3-yl)-1,3-thiazol-2-amine, |
| 54 | N-[2,6-dibromo-4-(2-methoxyethoxy)phenyl]-4-(2-methylimidazo[1,2-a]pyridin-3-yl)-1,3-thiazol-2-amine, |
| 55 | 1-(4-{[4-(2-methylimidazo[1,2-a]pyridin-3-yl)-1,3-thiazol-2-yl]amino}phenyl)ethanone, |
| 56 | N-(1,3-benzodioxol-5-yl)-4-(2-methylimidazo[1,2-a]pyridin-3-yl)-1,3-thiazol-2-amine, |
| 57 | N-(2,6-difluoro-4-methoxyphenyl)-4-(2-methylimidazo[1,2-a]pyridin-3-yl)-1,3-thiazol-2-amine, |
| 58 | N'-[4-(6-chloro-2-methylimidazo[1,2-a]pyridin-3-yl)-1,3-thiazol-2-yl]-N,N-dimethylbenzene-1,4-diamine, |
| 59 | 4-(6-chloro-2-methylimidazo[1,2-a]pyridin-3-yl)-N-(4-methoxyphenyl)-1,3-thiazol-2-amine, |
| 60 | 4-(6-chloro-2-methylimidazo[1,2-a]pyridin-3-yl)-N-(4-chlorophenyl)-1,3-thiazol-2-amine, |
| 61 | N-(4-bromophenyl)-4-(6-chloro-2-methylimidazo[1,2-a]pyridin-3-yl)-1,3-thiazol-2-amine, |
| 62 | 1-(4-{[4-(6-chloro-2-methylimidazo[1,2-a]pyridin-3-yl)-1,3-thiazol-2-yl]amino}phenyl)ethanone, |

-continued

| Cpd | Name |
|---|---|
| 63 | N-(1,3-benzodioxol-5-yl)-4-(2,7-dimethylimidazo[1,2-a]pyridin-3-yl)-1,3-thiazol-2-amine, |
| 64 | N'-[4-(2,7-dimethylimidazo[1,2-a]pyridin-3-yl)-1,3-thiazol-2-yl]-N,N-dimethylbenzene-1,4-diamine, |
| 65 | N-(4-chlorophenyl)-4-(2,7-dimethylimidazo[1,2-a]pyridin-3-yl)-1,3-thiazol-2-amine, |
| 66 | 4-(2,7-dimethylimidazo[1,2-a]pyridin-3-yl)-N-(3-fluoro-4-methoxyphenyl)-1,3-thiazol-2-amine, |
| 67 | N-(3-chloro-4-methoxyphenyl)-4-(2,7-dimethylimidazo[1,2-a]pyridin-3-yl)-1,3-thiazol-2-amine, |
| 68 | N-(4-bromophenyl)-4-(2,7-dimethylimidazo[1,2-a]pyridin-3-yl)-1,3-thiazol-2-amine, |
| 69 | 4-(2,7-dimethylimidazo[1,2-a]pyridin-3-yl)-N-(4-iodophenyl)-1,3-thiazol-2-amine, |
| 70 | N'-[4-(2,6-dimethylimidazo[1,2-a]pyridin-3-yl)-1,3-thiazol-2-yl]-N,N-dimethylbenzene-1,4-diamine, |
| 71 | 4-(2,6-dimethylimidazo[1,2-a]pyridin-3-yl)-N-(4-methoxyphenyl)-1,3-thiazol-2-amine, |
| 72 | N-(1,3-benzodioxol-5-yl)-4-(2,6-dimethylimidazo[1,2-a]pyridin-3-yl)-1,3-thiazol-2-amine, |
| 73 | N-(3-chloro-4-methoxyphenyl)-4-(2,6-dimethylimidazo[1,2-a]pyridin-3-yl)-1,3-thiazol-2-amine, |
| 74 | 4-(2,6-dimethylimidazo[1,2-a]pyridin-3-yl)-N-[4-(2-methoxyethoxy)phenyl]-1,3-thiazol-2-amine, |
| 75 | N'-[4-(2,6-dimethylimidazo[1,2-a]pyridin-3-yl)-1,3-thiazol-2-yl]-N,N-diethylbenzene-1,4-diamine, |
| 76 | 4-(2,6-dimethylimidazo[1,2-a]pyridin-3-yl)-N-(4-iodophenyl)-1,3-thiazol-2-amine, |
| 77 | N-(4-bromophenyl)-4-(2,6-dimethylimidazo[1,2-a]pyridin-3-yl)-1,3-thiazol-2-amine, |
| 78 | N-(4-chlorophenyl)-4-(2,6-dimethylimidazo[1,2-a]pyridin-3-yl)-1,3-thiazol-2-amine, |
| 79 | 4-(imidazo[1,2-a]pyridin-3-yl)-N-(4-iodophenyl)-1,3-thiazol-2-amine, |
| 80 | N-(4-bromophenyl)-N-methyl-4-(2-methylimidazo[1,2-a]pyrimidin-3-yl)-1,3-thiazol-2-amine, |
| 81 | N'-[4-(6-bromo-2-methylimidazo[1,2-a]pyridin-3-yl)-1,3-thiazol-2-yl]-N,N-dimethylbenzene-1,4-diamine, |
| 82 | N-(1,3-benzodioxol-5-yl)-4-(6-bromo-2-methylimidazo[1,2-a]pyridin-3-yl)-1,3-thiazol-2-amine, |
| 83 | 4-(imidazo[1,2-a]pyrimidin-3-yl)-N-(4-iodophenyl)-1,3-thiazol-2-amine, |
| 84 | N-(3,4-dimethoxyphenyl)-4-(2-methylimidazo[1,2-a]pyrimidin-3-yl)-1,3-thiazol-2-amine, |
| 85 | 4-(2-methylimidazo[1,2-a]pyrimidin-3-yl)-N-(4-methylphenyl)-1,3-thiazol-2-amine, |
| 86 | N-(4-ethylphenyl)-4-(2-methylimidazo[1,2-a]pyrimidin-3-yl)-1,3-thiazol-2-amine, |
| 87 | 4-(2-methylimidazo[1,2-a]pyrimidin-3-yl)-N-[4-(propan-2-yl)phenyl]-1,3-thiazol-2-amine, |
| 88 | 4-(6-chloro-2-methylimidazo[1,2-a]pyridin-3-yl)-N-(4-ethoxyphenyl)-1,3-thiazol-2-amine, |
| 89 | 4-(6-chloro-2-methylimidazo[1,2-a]pyridin-3-yl)-N-(4-methylphenyl)-1,3-thiazol-2-amine, |
| 90 | 4-(6-chloro-2-methylimidazo[1,2-a]pyridin-3-yl)-N-(4-ethylphenyl)-1,3-thiazol-2-amine, |
| 91 | 4-(6-chloro-2-methylimidazo[1,2-a]pyridin-3-yl)-N-[4-(propan-2-yl)phenyl]-1,3-thiazol-2-amine, |
| 92 | 4-{[4-(6-chloro-2-methylimidazo[1,2-a]pyridin-3-yl)-1,3-thiazol-2-yl]amino}phenol, |
| 93 | 4-(6-chloro-2-methylimidazo[1,2-a]pyridin-3-yl)-N-[4-(2-methoxyethoxy)phenyl]-1,3-thiazol-2-amine, |
| 94 | 3-[2-(1,3-benzodioxol-5-ylamino)-1,3-thiazol-4-yl]-2-methylimidazo[1,2-a]pyridin-8-ol, |
| 95 | N-(3-chloro-4-methoxyphenyl)-4-(6-chloro-2-methylimidazo[1,2-a]pyridin-3-yl)-1,3-thiazol-2-amine, |
| 96 | 4-(6-chloro-2-methylimidazo[1,2-a]pyridin-3-yl)-N-(3-fluoro-4-methoxyphenyl)-1,3-thiazol-2-amine, |
| 97 | N-(4-{[4-(6-chloro-2-methylimidazo[1,2-a]pyridin-3-yl)-1,3-thiazol-2-yl]amino}phenyl)acetamide, |
| 98 | 4-(6-chloro-2-methylimidazo[1,2-a]pyridin-3-yl)-N-(2,6-dichlorophenyl)-1,3-thiazol-2-amine, |
| 99 | 1-(4-{[4-(6-bromo-2-methylimidazo[1,2-a]pyridin-3-yl)-1,3-thiazol-2-yl]amino}phenyl)ethanone, |
| 100 | 4-(6-bromo-2-methylimidazo[1,2-a]pyridin-3-yl)-N-(4-chlorophenyl)-1,3-thiazol-2-amine, |
| 101 | 4-(6-bromo-2-methylimidazo[1,2-a]pyridin-3-yl)-N-(4-iodophenyl)-1,3-thiazol-2-amine, |
| 102 | 4-(6-bromo-2-methylimidazo[1,2-a]pyridin-3-yl)-N-(4-bromophenyl)-1,3-thiazol-2-amine, |
| 103 | 4-(6-bromo-2-methylimidazo[1,2-a]pyridin-3-yl)-N-(3-chloro-4-methoxyphenyl)-1,3-thiazol-2-amine, |
| 104 | 4-(6-bromo-2-methylimidazo[1,2-a]pyridin-3-yl)-N-(3-fluoro-4-methoxyphenyl)-1,3-thiazol-2-amine, |
| 105 | 4-(6-chloroimidazo[1,2-a]pyridin-3-yl)-N-(4-methoxyphenyl)-1,3-thiazol-2-amine, |
| 106 | N'-[4-(6-chloroimidazo[1,2-a]pyridin-3-yl)-1,3-thiazol-2-yl]-N,N-dimethylbenzene-1,4-diamine, |
| 107 | 1-(4-{[4-(6-chloroimidazo[1,2-a]pyridin-3-yl)-1,3-thiazol-2-yl]amino}phenyl)ethanone, |
| 108 | 4-(6-chloroimidazo[1,2-a]pyridin-3-yl)-N-(4-iodophenyl)-1,3-thiazol-2-amine, |
| 109 | 4-(6-chloroimidazo[1,2-a]pyridin-3-yl)-N-(3-chloro-4-methoxyphenyl)-1,3-thiazol-2-amine, |
| 110 | 4-(6-chloroimidazo[1,2-a]pyridin-3-yl)-N-(3-fluoro-4-methoxyphenyl)-1,3-thiazol-2-amine, |
| 111 | 4-(6-chloro-2-methylimidazo[1,2-a]pyridin-3-yl)-N-(3,4-dichlorophenyl)-1,3-thiazol-2-amine, |

-continued

| Cpd | Name |
|---|---|
| 112 | N-(4-tert-butylphenyl)-4-(6-chloro-2-methylimidazo[1,2-a]pyridin-3-yl)-1,3-thiazol-2-amine, |
| 113 | N-(4-chlorophenyl)-4-(2-methylimidazo[1,2-a]pyridin-3-yl)pyrimidin-2-amine, |
| 114 | N-(4-bromophenyl)-4-(2-methylimidazo[1,2-a]pyridin-3-yl)pyrimidin-2-amine, |
| 115 | N-(4-methoxyphenyl)-4-(2-methylimidazo[1,2-a]pyridin-3-yl)pyrimidin-2-amine, |
| 116 | N-(4-ethoxyphenyl)-4-(2-methylimidazo[1,2-a]pyridin-3-yl)pyrimidin-2-amine, |
| 117 | 1-(4-{[4-(2-methylimidazo[1,2-a]pyridin-3-yl)pyrimidin-2-yl]amino}phenyl)ethanone, |
| 118 | N,N-dimethyl-N'-[4-(2-methylimidazo[1,2-a]pyridin-3-yl)pyrimidin-2-yl]benzene-1,3-diamine, |
| 119 | N-(4-iodophenyl)-4-(2-methylimidazo[1,2-a]pyridin-3-yl)pyrimidin-2-amine, |
| 120 | N-(4-iodophenyl)-4-(2-methylimidazo[1,2-a]pyrimidin-3-yl)pyrimidin-2-amine, |
| 121 | N-(4-bromophenyl)-5-methyl-4-(2-methylimidazo[1,2-a]pyrimidin-3-yl)-1,3-thiazol-2-amine, |
| 122 | N-(4-iodophenyl)-5-methyl-4-(2-methylimidazo[1,2-a]pyrimidin-3-yl)-1,3-thiazol-2-amine, |
| 123 | N-(1,3-benzodioxol-5-yl)-4-(2-methylimidazo[1,2-a]pyridin-3-yl)pyrimidin-2-amine, |
| 124 | N-(1,3-benzodioxol-5-yl)-4-(2-methylimidazo[1,2-a]pyrimidin-3-yl)pyrimidin-2-amine, |
| 125 | N-(4-iodophenyl)-N-methyl-4-(2-methylimidazo[1,2-a]pyrimidin-3-yl)pyrimidin-2-amine, |
| 126 | N-(4-bromophenyl)-4-(2-methylimidazo[1,2-a]pyrimidin-3-yl)pyrimidin-2-amine, |
| 127 | N-(3-bromophenyl)-4-(2-methylimidazo[1,2-a]pyrimidin-3-yl)pyrimidin-2-amine, |
| 128 | N-(4-ethoxyphenyl)-4-(2-methylimidazo[1,2-a]pyrimidin-3-yl)pyrimidin-2-amine, |
| 129 | N,N-dimethyl-N'-[4-(2-methylimidazo[1,2-a]pyrimidin-3-yl)pyrimidin-2-yl]benzene-1,4-diamine, |
| 130 | N,N-diethyl-N'-[4-(2-methylimidazo[1,2-a]pyrimidin-3-yl)pyrimidin-2-yl]benzene-1,4-diamine, |
| 131 | 1-(4-{[4-(2-methylimidazo[1,2-a]pyrimidin-3-yl)pyrimidin-2-yl]amino}phenyl)ethanone, |
| 132 | N-(4-bromo-2-chlorophenyl)-4-(6-chloro-2-methylimidazo[1,2-a]pyridin-3-yl)-1,3-thiazol-2-amine, |
| 133 | 4-(6-chloro-2-methylimidazo[1,2-a]pyridin-3-yl)-N-phenyl-1,3-thiazol-2-amine, |
| 134 | 4-(6-chloroimidazo[1,2-a]pyridin-3-yl)-N-[2,6-dibromo-4-(2-methoxyethoxy)phenyl]-1,3-thiazol-2-amine, |
| 135 | 4-(6-chloroimidazo[1,2-a]pyridin-3-yl)-N-(2,4,6-tribromophenyl)-1,3-thiazol-2-amine, |
| 136 | 4-(6-chloroimidazo[1,2-a]pyridin-3-yl)-N-(2,4,6-trichlorophenyl)-1,3-thiazol-2-amine, |
| 137 | N,N,N'-trimethyl-N'-[4-(2-methylimidazo[1,2-a]pyrimidin-3-yl)pyrimidin-2-yl]benzene-1,4-diamine, |
| 138 | N,N-diethyl-N'-methyl-N'-[4-(2-methylimidazo[1,2-a]pyrimidin-3-yl)pyrimidin-2-yl]benzene-1,4-diamine, |
| 139 | N-(1,3-benzodioxol-5-yl)-N-methyl-4-(2-methylimidazo[1,2-a]pyrimidin-3-yl)pyrimidin-2-amine, |
| 140 | N-(2-chlorophenyl)-N-methyl-4-(2-methylimidazo[1,2-a]pyrimidin-3-yl)pyrimidin-2-amine, |
| 141 | N-(4-methoxy-2,6-dimethylphenyl)-4-(2-methylimidazo[1,2-a]pyrimidin-3-yl)pyrimidin-2-amine, |
| 142 | N-(4-ethoxyphenyl)-N-methyl-4-(2-methylimidazo[1,2-a]pyrimidin-3-yl)pyrimidin-2-amine, |
| 143 | N-(4-iodophenyl)-N-methyl-4-(2-methylimidazo[1,2-a]pyrimidin-3-yl)pyrimidin-2-amine, |
| 144 | 4-(2-ethylimidazo[1,2-a]pyrimidin-3-yl)-N-(4-methoxyphenyl)-1,3-thiazol-2-amine, |
| 145 | N'-[4-(2-ethylimidazo[1,2-a]pyrimidin-3-yl)-1,3-thiazol-2-yl]-N,N-dimethylbenzene-1,4-diamine, |
| 146 | N-(2,6-dibromo-4-methoxyphenyl)-4-(2-ethylimidazo[1,2-a]pyrimidin-3-yl)-1,3-thiazol-2-amine, |
| 147 | N-(4-chlorophenyl)-4-(2-ethylimidazo[1,2-a]pyrimidin-3-yl)-1,3-thiazol-2-amine, |
| 148 | N-(4-bromophenyl)-4-(2-ethylimidazo[1,2-a]pyrimidin-3-yl)-1,3-thiazol-2-amine, |
| 149 | 4-(2-ethylimidazo[1,2-a]pyrimidin-3-yl)-N-(4-iodophenyl)-1,3-thiazol-2-amine, |
| 150 | 1-(4-{[4-(2-ethylimidazo[1,2-a]pyrimidin-3-yl)-1,3-thiazol-2-yl]amino}phenyl)ethanone, |
| 151 | N-(1,3-benzodioxol-5-yl)-4-(2-ethylimidazo[1,2-a]pyrimidin-3-yl)-1,3-thiazol-2-amine, |
| 152 | 4-(2-ethylimidazo[1,2-a]pyrimidin-3-yl)-N-(3-fluoro-4-methoxyphenyl)-1,3-thiazol-2-amine, |
| 153 | N-(3-chloro-4-methoxyphenyl)-4-(2-ethylimidazo[1,2-a]pyrimidin-3-yl)-1,3-thiazol-2-amine, |
| 154 | N-(1,3-benzodioxol-5-yl)-4-[2-(trifluoromethyl)imidazo[1,2-a]pyrimidin-3-yl]-1,3-thiazol-2-amine, |
| 155 | N-(3-fluoro-4-methoxyphenyl)-4-(6-fluoro-2-methylimidazo[1,2-a]pyridin-3-yl)-1,3-thiazol-2-amine, |
| 156 | 4-(6-fluoro-2-methylimidazo[1,2-a]pyridine-3-yl)-N-(4-iodophenyl)-1,3-thiazol-2-amine, |
| 157 | N'-[4-(6-fluoro-2-methylimidazo[1,2-a]pyridin-3-yl)-1,3-thiazol-2-yl]-N,N-dimethylbenzene-1,4-diamine, |
| 158 | N-(1,3-benzodioxol-5-yl)-4-(6-fluoro-2-methylimidazo[1,2-a]pyridin-3-yl)-1,3-thiazol-2-amine, |
| 159 | 1-(4-{[4-(6-fluoro-2-methylimidazo[1,2-a]pyridin-3-yl)-1,3-thiazol-2-yl]amino}phenyl)ethanone, |
| 160 | 4-(6-fluoro-2-methylimidazo[1,2-a]pyridin-3-yl)-N-(4-methoxyphenyl)-1,3-thiazol-2-amine, |
| 161 | N-(4-chlorophenyl)-4-(6-fluoro-2-methylimidazo[1,2-a]pyridin-3-yl)-1,3-thiazol-2-amine, |
| 162 | N-(4-bromophenyl)-4-(6-fluoro-2-methylimidazo[1,2-a]pyridin-3-yl)-1,3-thiazol-2-amine, |
| 163 | N-(4-ethoxyphenyl)-4-(6-fluoro-2-methylimidazo[1,2-a]pyridin-3-yl)-1,3-thiazol-2-amine, |
| 164 | N-(4-tert-butylphenyl)-4-(6-fluoro-2-methylimidazo[1,2-a]pyridin-3-yl)-1,3-thiazol-2-amine, |

| Cpd | Name |
|---|---|
| 165 | N-(4-bromo-2-chlorophenyl)-4-(6-fluoro-2-methylimidazo[1,2-a]pyridin-3-yl)-1,3-thiazol-2-amine, |
| 166 | N-(2-fluorophenyl)-4-(imidazo[1,2-a]pyridin-3-yl)pyrimidin-2-amine, |
| 167 | 1-(4-{methyl[4-(2-methylimidazo[1,2-a]pyridin-3-yl)pyrimidin-2-yl]amino}phenyl)ethanone, |
| 168 | 4-(2-methylimidazo[1,2-a]pyridin-3-yl)-N-(4-methylphenyl)pyrimidin-2-amine, |
| 169 | 4-(2-methylimidazo[1,2-a]pyridin-3-yl)-N-(4-methylphenyl)pyrimidin-2-amine, |
| 170 | N-methyl-4-(2-methylimidazo[1,2-a]pyridin-3-yl)-N-(4-methylphenyl)pyrimidin-2-amine, |
| 171 | N-(3-fluoro-4-methoxyphenyl)-4-(2-propylimidazo[1,2-a]pyridin-3-yl)-1,3-thiazol-2-amine, |
| 172 | N-(3-chloro-4-methoxyphenyl)-4-(2-propylimidazo[1,2-a]pyridin-3-yl)-1,3-thiazol-2-amine, |
| 173 | N-(4-ethoxyphenyl)-4-(2-propylimidazo[1,2-a]pyridin-3-yl)-1,3-thiazol-2-amine, |
| 174 | N-(4-iodophenyl)-4-(2-propylimidazo[1,2-a]pyridin-3-yl)-1,3-thiazol-2-amine, |
| 175 | N-(1,3-benzodioxol-5-yl)-4-(2-propylimidazo[1,2-a]pyridin-3-yl)-1,3-thiazol-2-amine, |
| 176 | N,N-dimethyl-N'-[4-(2-propylimidazo[1,2-a]pyridin-3-yl)-1,3-thiazol-2-yl]benzene-1,4-diamine, |
| 177 | 1-(4-{[4-(2-propylimidazo[1,2-a]pyridin-3-yl)-1,3-thiazol-2-yl]amino}phenyl)ethanone, |
| 178 | N-(4-chlorophenyl)-4-(2-propylimidazo[1,2-a]pyridin-3-yl)-1,3-thiazol-2-amine, |
| 179 | N-(4-bromophenyl)-4-(2-propylimidazo[1,2-a]pyridin-3-yl)-1,3-thiazol-2-amine, |
| 180 | N-(4-methoxyphenyl)-4-(2-propylimidazo[1,2-a]pyridin-3-yl)-1,3-thiazol-2-amine, |
| 181 | N-(3-fluoro-4-methoxyphenyl)-4-(2-propylimidazo[1,2-a]pyrimidin-3-yl)-1,3-thiazol-2-amine, |
| 182 | N-(1,3-benzodioxol-5-yl)-4-(2-propylimidazo[1,2-a]pyrimidin-3-yl)-1,3-thiazol-2-amine, |
| 183 | N,N-dimethyl-N'-[4-(2-propylimidazo[1,2-a]pyrimidin-3-yl)-1,3-thiazol-2-yl]benzene-1,4-diamine, |
| 184 | N-(4-bromophenyl)-4-(2-propylimidazo[1,2-a]pyrimidin-3-yl)-1,3-thiazol-2-amine, |
| 185 | N-(4-iodophenyl)-4-(2-propylimidazo[1,2-a]pyrimidin-3-yl)-1,3-thiazol-2-amine, |
| 186 | N-(4-methoxyphenyl)-4-(2-propylimidazo[1,2-a]pyrimidin-3-yl)-1,3-thiazol-2-amine, |
| 187 | N-phenyl-4-(2-propylimidazo[1,2-a]pyrimidin-3-yl)-1,3-thiazol-2-amine, |
| 188 | N-(3-methoxyphenyl)-4-(2-methylimidazo[1,2-a]pyridin-3-yl)-1,3-thiazol-2-amine, |
| 189 | N-methyl-4-(2-methylimidazo[1,2-a]pyridin-3-yl)-N-(4-methylphenyl)pyrimidin-2-amine, |
| 190 | 3-{[4-(2-methylimidazo[1,2-a]pyridin-3-yl)pyrimidin-2-yl]amino}phenol, |
| 191 | 4-(2-methylimidazo[1,2-a]pyridin-3-yl)-N-(4-methylphenyl)-1,3-thiazol-2-amine, |
| 192 | N-(4-ethylphenyl)-4-(2-methylimidazo[1,2-a]pyridin-3-yl)-1,3-thiazol-2-amine, |
| 193 | N,N-diethyl-N'-[4-(2-methylimidazo[1,2-a]pyridin-3-yl)-1,3-thiazol-2-yl]benzene-1,4-diamine, |
| 194 | N-(4-{[4-(2-methylimidazo[1,2-a]pyridin-3-yl)-1,3-thiazol-2-yl]amino}phenyl)acetamide, |
| 195 | N-(1,3-benzodioxol-5-yl)-4-[2-(trifluoromethyl)imidazo[1,2-a]pyridin-3-yl]-1,3-thiazol-2-amine, |
| 196 | 4-{[4-(2-methylimidazo[1,2-a]pyridin-3-yl)pyrimidin-2-yl]amino}benzoic acid, |
| 197 | N-(4-bromophenyl)-4-(2-methylimidazo[1,2-a]pyridin-3-yl)-1,3-thiazol-2-amine, |
| 198 | N-(3,4-dichlorophenyl)-4-(2-methylimidazo[1,2-a]pyridin-3-yl)-1,3-thiazol-2-amine, |
| 199 | N-(4-chlorophenyl)-4-(2-methylimidazo[1,2-a]pyridin-3-yl)-1,3-thiazol-2-amine, |
| 200 | N-(4-bromo-2-chlorophenyl)-4-(2-methylimidazo[1,2-a]pyridin-3-yl)-1,3-thiazol-2-amine, |
| 201 | 4-{[4-(2-methylimidazo[1,2-a]pyridin-3-yl)-1,3-thiazol-2-yl]amino}benzene-1,2-diol, |
| 202 | N-(3,4-dimethoxyphenyl)-4-(2-methylimidazo[1,2-a]pyridin-3-yl)-1,3-thiazol-2-amine, |
| 203 | N-(2,4-difluorophenyl)-4-(2-methylimidazo[1,2-a]pyridin-3-yl)-1,3-thiazol-2-amine, |
| 204 | N-(4-ethoxyphenyl)-4-(2-methylimidazo[1,2-a]pyridin-3-yl)-1,3-thiazol-2-amine, |
| 205 | N-(2-bromo-4-methylphenyl)-4-(6-chloro-2-methylimidazo[1,2-a]pyridin-3-yl)-1,3-thiazol-2-amine, |
| 206 | N'-[4-(6-chloro-2-methylimidazo[1,2-a]pyridin-3-yl)-1,3-thiazol-2-yl]-N,N-diethylbenzene-1,4-diamine, |
| 207 | 4-(6-chloro-2-methylimidazo[1,2-a]pyridin-3-yl)-N-(3,4-dimethoxyphenyl)-1,3-thiazol-2-amine, |
| 208 | N-(2-bromo-4-methoxyphenyl)-4-(6-chloro-2-methylimidazo[1,2-a]pyridin-3-yl)-1,3-thiazol-2-amine, |
| 209 | 4-(6-chloro-2-methylimidazo[1,2-a]pyridin-3-yl)-N-(3-methylphenyl)-1,3-thiazol-2-amine, |
| 210 | 3-{[4-(6-chloro-2-methylimidazo[1,2-a]pyridin-3-yl)-1,3-thiazol-2-yl]amino}phenol, |
| 211 | 1-(3-{[4-(6-chloro-2-methylimidazo[1,2-a]pyridin-3-yl)-1,3-thiazol-2-yl]amino}phenyl)ethanone, |
| 212 | N-(3-bromophenyl)-4-(6-chloro-2-methylimidazo[1,2-a]pyridin-3-yl)-1,3-thiazol-2-amine, |
| 213 | 4-(6-chloro-2-methylimidazo[1,2-a]pyridin-3-yl)-N-(3-chlorophenyl)-1,3-thiazol-2-amine, |
| 214 | 4-(6-chloro-2-methylimidazo[1,2-a]pyridin-3-yl)-N-(2,4-dimethylphenyl)-1,3-thiazol-2-amine, |
| 215 | 4-(6-chloro-2-methylimidazo[1,2-a]pyridin-3-yl)-N-(3-fluorophenyl)-1,3-thiazol-2-amine, |
| 216 | N-(4-bromo-2-methylphenyl)-4-(6-chloro-2-methylimidazo[1,2-a]pyridin-3-yl)-1,3-thiazol-2-amine, |
| 217 | 4-(6-chloro-2-methylimidazo[1,2-a]pyridin-3-yl)-N-(3-methoxyphenyl)-1,3-thiazol-2-amine, |
| 218 | 4-(6-chloro-2-methylimidazo[1,2-a]pyridin-3-yl)-N-(2,4-dichlorophenyl)-1,3-thiazol-2-amine, |
| 219 | 4-(6-chloro-2-methylimidazo[1,2-a]pyridin-3-yl)-N-(2,2-dimethyl-1,3-benzodioxol-5-yl)-1,3-thiazol-2-amine, |
| 220 | N-(1,3-benzodioxol-5-yl)-4-(6,8-dichloro-2-methylimidazo[1,2-a]pyridin-3-yl)-1,3-thiazol-2-amine, |

-continued

| Cpd | Name |
|---|---|
| 221 | N'-[4-(2,8-dimethylimidazo[1,2-a]pyridin-3-yl)-1,3-thiazol-2-yl]-N,N-dimethylbenzene-1,4-diamine, |
| 222 | 4-(2,8-dimethylimidazo[1,2-a]pyridin-3-yl)-N-(4-methoxyphenyl)-1,3-thiazol-2-amine, |
| 223 | 4-(2,8-dimethylimidazo[1,2-a]pyridin-3-yl)-N-(4-methylphenyl)-1,3-thiazol-2-amine, |
| 224 | N-(4-chlorophenyl)-4-(2,8-dimethylimidazo[1,2-a]pyridin-3-yl)-1,3-thiazol-2-amine, |
| 225 | 4-(2,8-dimethylimidazo[1,2-a]pyridin-3-yl)-N-(3-methoxyphenyl)-1,3-thiazol-2-amine, |
| 226 | N-(1,3-benzodioxol-5-yl)-4-(2,8-dimethylimidazo[1,2-a]pyridin-3-yl)-1,3-thiazol-2-amine, |
| 227 | N'-[4-(8-bromo-2-methylimidazo[1,2-a]pyridin-3-yl)-1,3-thiazol-2-yl]-N,N-dimethylbenzene-1,4-diamine, |
| 228 | 4-(8-bromo-2-methylimidazo[1,2-a]pyridin-3-yl)-N-(4-methoxyphenyl)-1,3-thiazol-2-amine, |
| 229 | 4-(8-bromo-2-methylimidazo[1,2-a]pyridin-3-yl)-N-(4-methylphenyl)-1,3-thiazol-2-amine, |
| 230 | 4-(8-bromo-2-methylimidazo[1,2-a]pyridin-3-yl)-N-(4-chlorophenyl)-1,3-thiazol-2-amine, |
| 231 | 4-(8-bromo-2-methylimidazo[1,2-a]pyridin-3-yl)-N-phenyl-1,3-thiazol-2-amine, |
| 232 | 4-(8-bromo-2-methylimidazo[1,2-a]pyridin-3-yl)-N-(3-methoxyphenyl)-1,3-thiazol-2-amine, |
| 233 | 4-(8-bromo-2-methylimidazo[1,2-a]pyridin-3-yl)-N-(2-chlorophenyl)-1,3-thiazol-2-amine, |
| 234 | 4-(8-bromo-2-methylimidazo[1,2-a]pyridin-3-yl)-N-(2-methoxyphenyl)-1,3-thiazol-2-amine, |
| 235 | N-(1,3-benzodioxol-5-yl)-4-(8-bromo-2-methylimidazo[1,2-a]pyridin-3-yl)-1,3-thiazol-2-amine, |
| 236 | 4-(6-fluoro-2-methylimidazo[1,2-a]pyridin-3-yl)-N-(3-methoxyphenyl)-1,3-thiazol-2-amine, |
| 237 | 4-(6-fluoro-2-methylimidazo[1,2-a]pyridin-3-yl)-N-(4-methylphenyl)-1,3-thiazol-2-amine, |
| 238 | 1-(3-{[4-(6-fluoro-2-methylimidazo[1,2-a]pyridin-3-yl)-1,3-thiazol-2-yl]amino}phenyl)ethanone, |
| 239 | N-(2,6-dibromophenyl)-4-(6-fluoro-2-methylimidazo[1,2-a]pyridin-3-yl)-1,3-thiazol-2-amine, |
| 240 | 4-(7-chloro-2-methylimidazo[1,2-a]pyridin-3-yl)-N-(4-chlorophenyl)-1,3-thiazol-2-amine, |
| 241 | 4-(7-chloro-2-methylimidazo[1,2-a]pyridin-3-yl)-N-(4-methoxyphenyl)-1,3-thiazol-2-amine, |
| 242 | N'-[4-(7-chloro-2-methylimidazo[1,2-a]pyridin-3-yl)-1,3-thiazol-2-yl]-N,N-dimethylbenzene-1,4-diamine, |
| 243 | 4-(7-chloro-2-methylimidazo[1,2-a]pyridin-3-yl)-N-(4-methylphenyl)-1,3-thiazol-2-amine, |
| 244 | 1-(4-{[4-(7-chloro-2-methylimidazo[1,2-a]pyridin-3-yl)-1,3-thiazol-2-yl]amino}phenyl)ethanone, |
| 245 | 4-(imidazo[1,2-a]pyridin-3-yl)-N-(4-methoxyphenyl)pyrimidin-2-amine, |
| 246 | N-(3-chlorophenyl)-4-(imidazo[1,2-a]pyridin-3-yl)pyrimidin-2-amine, |
| 247 | N-(2-chlorophenyl)-4-(imidazo[1,2-a]pyridin-3-yl)pyrimidin-2-amine, |
| 248 | N-(4-fluorophenyl)-4-(imidazo[1,2-a]pyridin-3-yl)pyrimidin-2-amine, |
| 249 | N-(2,6-dibromo-4-methoxyphenyl)-4-(imidazo[1,2-a]pyridin-3-yl)pyrimidin-2-amine, |
| 250 | 1-(4-{[4-(imidazo[1,2-a]pyridin-3-yl)pyrimidin-2-yl]amino}phenyl)ethanone, |
| 251 | N-(1,3-benzodioxol-5-yl)-4-(imidazo[1,2-a]pyridin-3-yl)pyrimidin-2-amine, |
| 252 | N-(4-ethoxyphenyl)-4-(imidazo[1,2-a]pyridin-3-yl)pyrimidin-2-amine, |
| 253 | N,N-diethyl-N'-[4-(imidazo[1,2-a]pyridin-3-yl)pyrimidin-2-yl]benzene-1,4-diamine, |
| 254 | N'-[4-(imidazo[1,2-a]pyridin-3-yl)pyrimidin-2-yl]-N,N-dimethylbenzene-1,4-diamine, |
| 255 | N-(3-fluorophenyl)-4-(imidazo[1,2-a]pyridin-3-yl)pyrimidin-2-amine, |
| 256 | N-(3-bromophenyl)-4-(imidazo[1,2-a]pyridin-3-yl)pyrimidin-2-amine, |
| 257 | N-(2,6-dibromo-4-methoxyphenyl)-4-(imidazo[1,2-a]pyrimidin-3-yl)pyrimidin-2-amine, |
| 258 | 1-(4-{[4-(imidazo[1,2-a]pyrimidin-3-yl)pyrimidin-2-yl]amino}phenyl)ethanone, |
| 259 | N-(1,3-benzodioxol-5-yl)-4-(imidazo[1,2-a]pyrimidin-3-yl)pyrimidin-2-amine, |
| 260 | 4-(imidazo[1,2-a]pyrimidin-3-yl)-N-(3-methoxyphenyl)pyrimidin-2-amine, |
| 261 | 4-(imidazo[1,2-a]pyrimidin-3-yl)-N-(4-methoxyphenyl)pyrimidin-2-amine, |
| 262 | N-(4-ethoxyphenyl)-4-(imidazo[1,2-a]pyrimidin-3-yl)pyrimidin-2-amine, |
| 263 | N,N-diethyl-N'-[4-(imidazo[1,2-a]pyrimidin-3-yl)pyrimidin-2-yl]benzene-1,4-diamine, |
| 264 | N'-[4-(imidazo[1,2-a]pyrimidin-3-yl)pyrimidin-2-yl]-N,N-dimethylbenzene-1,3-diamine, |
| 265 | N'-[4-(imidazo[1,2-a]pyrimidin-3-yl)pyrimidin-2-yl]-N,N-dimethylbenzene-1,4-diamine, |
| 266 | N-(2-fluorophenyl)-4-(imidazo[1,2-a]pyrimidin-3-yl)pyrimidin-2-amine, |
| 267 | N-(3-fluorophenyl)-4-(imidazo[1,2-a]pyrimidin-3-yl)pyrimidin-2-amine, |
| 268 | N-(4-fluorophenyl)-4-(imidazo[1,2-a]pyrimidin-3-yl)pyrimidin-2-amine, |
| 269 | N-(3-chlorophenyl)-4-(imidazo[1,2-a]pyrimidin-3-yl)pyrimidin-2-amine, |
| 270 | N-(4-bromophenyl)-4-(imidazo[1,2-a]pyrimidin-3-yl)pyrimidin-2-amine, |
| 271 | N-(4-bromophenyl)-4-(2-ethylimidazo[1,2-a]pyrimidin-3-yl)pyrimidin-2-amine. |

An embodiment of the method described herein comprises administering an effective amount of a compound to inhibit cancer stem cell production.

An embodiment of the method described herein further comprises administering an effective amount of a compound for blocking the $G_2$/M phase of the cell cycle to inhibit cancer stem cell production.

An embodiment described herein includes the use of a compound of Formula (I) or a form thereof in the manufacture of a medicament for treating cancer in a subject in need thereof comprising administering an effective amount of the medicament to the subject.

Another embodiment described herein is directed to the use of a compound of Formula (I) or a form or composition thereof for treating cancer by down-regulating translational expression of Bmi-1 mRNA.

Any type of cancer can be treated in accordance with the intended use of the compounds described herein. As used herein, the term "cancer" refers cells that aberrantly express Bmi-1. In another embodiment, a cancer is characterized by cells or a fraction of cells that overexpress Bmi-1 relative to cells from a cancer-free patient (i.e., a patient with no detectable cancer as determined by conventional techniques, such as MRI, CAT scan etc.) or cells from surrounding normal tissues by at least 10%, 25%, 35%, 45%, 55%, 65%, 75%, 85%. 90%, or 95% more, as detected by any method routinely used in the art, or described herein, e.g., in an ELISA.

Non-limiting examples of cancers that can be treated with the intended use described herein: leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkins disease, non-Hodgkins disease; multiple myelomas such as but not limited to smoldering multiple myeloma, nonsecretory myeloma, osteosclerotic myeloma, placancer cell leukemia, solitary placancercytoma and extramedullary placancercytoma; Waldenström's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (cancer cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, placancercytoma, verrucous carcinoma, and oat cell (cancer cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular, carcinoma and hepatoblastoma; gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, *Medicine*, 2d Ed., J.B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America).

The compounds are also useful in the treatment, prevention and/or management of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T cell lymphoma, Burkett's lymphoma, Burkitt's lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xeroderma pigmentosum, keratoactantoma, seminoma, thyroid follicular cancer and teratocarcinoma. In some embodiments, cancers associated with aberrations in apoptosis are treated in accordance with the methods described herein. Such cancers may include, but are not limited to, follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders of the skin, lung, liver, bone, brain, stomach, colon, breast, prostate, bladder, kidney, pancreas, ovary, and/or uterus are treated in accordance with the methods described herein. In other specific embodiments, a sarcoma, or melanoma is treated as described herein.

In a specific embodiment, the cancer being treated as described herein is leukemia, lymphoma or myeloma (e.g., multiple myeloma). Non-limiting examples of leukemias and other blood-borne cancers that can be treated with the methods described herein include acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia "CML", chronic lymphocytic leukemia "CLL", and hairy cell leukemia.

Non-limiting examples of lymphomas that can be treated in accordance with the methods described herein include Hodgkins disease, non-Hodgkins Lymphoma, Multiple myeloma, Waldenström's macroglobulinemia, heavy chain disease, and Polycythemia vera.

In another embodiment, the cancer being treated as described herein is a solid tumor. Examples of solid tumors that can be treated in accordance with the methods described herein include, but are not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

In certain embodiments, cancer includes, but is not limited to, brain cancer, gastric cancer, hematologic cancer, lung cancer, non-small cell lung cancer, pancreatic cancer, prostate cancer, salivary gland cancer, colorectal carcinoma, hepatocellular carcinoma, liver carcinoma, breast carcinomas or sarcomas, esophageal carcinomas or sarcomas, stomach carcinomas or sarcomas, fibrosarcoma, glioblastoma, medulloblastoma, neuroblastoma, diffuse large B cell lymphomas, B cell non-Hodgkin lymphoma, Hodgkins lymphoma or chronic or acute myeloid leukemia.

In certain embodiments, cancer includes, but is not limited to, tumors that relapse after therapy despite improved surgical and irradiation techniques. Tumor relapse may occur for a number of reasons, with one plausible explanation being the existence of cancer stem cells (CSC) or tumor initiating cells in the tumor population. CSCs are defined as a population of cells found within a tumor that have characteristics similar to normal stem cells. Like normal stem cells they have the potential to self renew and differentiate and are resistant to the cytotoxic drugs aimed to kill the cancer cells. Therefore targeting CSCs could be an approach for effective cancer treatment. One further approach is to target various transcription factors responsible for the maintenance of self renewal ability in the stem cells.

As used herein, the term "treating" refers to: (i) preventing a disease, disorder or condition from occurring in a subject that may be predisposed to the disease, disorder and/or condition but has not yet been diagnosed as having it; (ii) inhibiting a disease, disorder or condition, i.e., arresting its development; and/or (iii) relieving a disease, disorder or condition, i.e., causing regression of the disease, disorder and/or condition.

As used herein, the term "subject" refers to members of the human, equine, porcine, bovine, murine, canine and feline species. In some embodiments, the subject is a mammal or a warm-blooded vertebrate animal. In other embodiments, the subject is a human. As used herein, the term "patient" may be used interchangeably with "subject" and "human".

In certain embodiments, the subject is a human that is 0 to 6 months old, 6 to 12 months old, 6 to 18 months old, 18 to 36 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In some embodiments, the subject is a human infant. In other embodiments, the subject is a human toddler. In other embodiments, the subject is a human child. In other embodiments, the subject is human adult. In yet other embodiments, the subject is an elderly human.

As used herein, the term "elderly human" refers to a human 65 years or older; the term "human adult" refers to a human that is 18 years or older; the term "human child" refers to a human that is 1 year to 18 years old; the term "human infant" refers to a newborn to 1 year old year human; and, the term "human toddler" refers to a human that is 1 year to 3 years old.

In certain embodiments, the subject is in an immunocompromised state or immunosuppressed state or at risk for becoming immunocompromised or immunosuppressed. In certain embodiments, the subject is receiving or recovering from an immunosuppressive therapy. In certain embodiments, the subject has or is at risk of getting cancer, AIDS, or a bacterial infection. In certain embodiments, the subject is, will or has undergone surgery, chemotherapy and/or radiation therapy. In certain embodiments, the subject has cystic fibrosis, pulmonary fibrosis or another condition affecting the lungs. In certain embodiments, the subject has, will have or had a tissue transplant.

In some embodiments, the subject has proven refractory to therapies other than treatment with compounds, but are no longer on these therapies. In one embodiment, that a cancer is refractory to a therapy means that at least some significant portion of the cancer cells are not killed or their cell division arrested. The determination of whether the cancer cells are refractory can be made either in vivo or in vitro by any method known in the art for assaying the effect of a therapy on cancer cells, using the art-accepted meanings of "refractory" in such a context. In a certain embodiment, a refractory patient is a patient refractory to a standard therapy. In certain embodiments, a patient with cancer is refractory to a therapy when the tumor or neoplasm has not significantly been eradicated and/or the symptoms have not been significantly alleviated. The determination of whether a patient is refractory can be made either in vivo or in vitro by any method known in the art for assaying the effectiveness of a treatment of cancer, using art-accepted meanings of "refractory" in such a context.

In certain embodiments, the patient to be treated in accordance with the methods described herein are patients already being treated with antibiotics, anti-virals, anti-fungals, or other biological therapy or immunotherapy or anti-cancer therapy. Among these patients are refractory patients, and patients who are too young for conventional therapies. In some embodiments, the subject being administered one or more compounds has not received therapy prior to the administration of the compounds.

In some embodiments, compounds are administered to a patient to prevent the onset of cancer in a patient at risk of developing cancer. In some embodiments, compounds are administered to a patient that is susceptible to adverse reactions to conventional therapies. In some embodiments, the subject being administered one or more compounds has not received prior therapy. In other embodiments, one or more compounds are administered to a subject who has received a therapy prior to administration of one or more compounds. In some embodiments, the subject administered a compound has experienced adverse side effects to the prior therapy or the prior therapy was discontinued due to unacceptable levels of toxicity to the subject.

In some embodiments, the subject being administered one or more compounds, will or has undergone surgery, chemotherapy, antibody therapy, hormonal therapy and/or radiation therapy. In certain embodiments, the patient has undergone surgery to remove the tumor or neoplasm. In certain embodiments, the subject will have, or has had, or is undergoing a tissue or organ transplant.

As used herein, the terms "effective amount" or "therapeutically effective amount" mean an amount of compound of Formula (I) or a form, composition or medicament thereof effective in inhibiting the above-noted diseases and thus producing the desired therapeutic, ameliorative, inhibitory or preventative effect in a subject in need thereof.

As used herein, the term "effective amount," in the context of administering a compound to a subject, refers to the amount of a compound which is sufficient to achieve at least one or more of the following effects: (i) reduce or ameliorate the severity of cancer or a symptom associated therewith; (ii) prevent the progression of cancer or a symptom associated therewith; (iii) cause regression of cancer or a symptom associated therewith; (iv) prevent the development or onset of cancer or a symptom associated therewith; (v) prevent the recurrence of cancer or a symptom associated with cancer; (vi) reduce the duration of a symptom associated with cancer; (vii) reduce or eliminate the cancer cell population; (viii) reduce or eliminate the growth of a tumor or neoplasm; (ix) reduce or eliminate the proliferation of cancer cells; (x) reduce the formation of a tumor or neoplasm; (xi) eradicate or control of primary, regional and/or metastatic cancer; (xii) reduce the mortality; (xiii) increase the number of patients in remission; (xiv) increase the length of remission in patients; (xv) maintain or control the size of a tumor or neoplasm so that the size does not increase or increases less than the size of the tumor after administration of a standard therapy as measured by conventional methods available to one of skill in the art, such as MRI, X-ray and CAT scan; (xvi) increase the survival of a subject; (xvii) reduce hospitalization of a subject; (xviii) reduce hospitalization length; (xix) enhance or improve the prophylactic or therapeutic effect(s) of another therapy; (xx) reduce the number of symptoms associated with cancer; (xxi) increase cancer-free survival of patients; and/or (xxii) increase symptom-free survival of cancer patients.

In general, the effective amount will be in a range of from about 0.001 mg/Kg/day to about 500 mg/Kg/day, or about 0.01 mg/Kg/day to about 500 mg/Kg/day, or about 0.1 mg to about 500 mg/Kg/day, or about 1.0 mg/day to about 500 mg/Kg/day, in single, divided, or a continuous dose for a patient or subject having a weight in a range of between about 40 to about 200 Kg (which dose may be adjusted for patients or subjects above or below this range, particularly children under 40 Kg). The typical adult subject is expected to have a median weight in a range of between about 70 to about 100 Kg. The effective amount for the subject will also depend upon various factors, including the subject's body weight, size and health. Effective amounts for a given patient can be determined by routine experimentation that is within the skill and judgment of the clinician.

In another embodiment, where daily doses are adjusted based upon the weight of the subject or patient, compounds described herein may be formulated for delivery at about 0.02, 0.025, 0.03, 0.05, 0.06, 0.075, 0.08, 0.09, 0.10, 0.20, 0.25, 0.30, 0.50, 0.60, 0.75, 0.80, 0.90, 1.0, 1.10, 1.20, 1.25, 1.50, 1.75, 2.0, 5.0, 10, 20 or 50 mg/Kg/day. Daily doses adjusted based upon the weight of the subject or patient may be administered as a single, divided, or continuous dose. In embodiments where a dose of compound is given more than once per day, it may be administered twice, thrice, or more per day. In another embodiment, a subject is administered one or more doses of an effective amount of a compound or a composition, wherein the effective amount may not be the same for each dose.

Within the scope described herein, the "effective amount" of a compound of Formula (I) or a form thereof for use in the manufacture of a medicament or in a method for treating cancer in a subject in need thereof, is intended to include an amount in a range of from about 0.1 mg to about 3500 mg administered daily; from about 1 mg to about 3000 mg administered daily; from about 5 mg to about 1500 mg administered daily; from about 10 mg to about 600 mg administered daily; from about 0.5 mg to about 2000 mg administered daily; or, an amount in a range of from about 5.0 mg to about 300 mg administered daily.

For any compound, the effective amount can be estimated initially either in cell culture assays or in relevant animal models, such as a mouse, chimpanzee, marmoset or tamarin animal model. Relevant animal models may also be used to determine the appropriate concentration range and route of administration. Such information can then be used to determine useful doses and routes for administration in humans. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$. In some embodiments, the effective amount is such that a large therapeutic index is achieved. In further embodiments, the dosage is within a range of circulating concentrations that include an $ED_{50}$ with little or no toxicity. The dosage may vary within this range depending upon the dosage form employed, sensitivity of the patient, and the route of administration.

The exact dosage will be determined by the practitioner, in light of factors related to the subject. Dosage and administration may be adjusted to provide sufficient levels of the active agent(s) or to maintain the desired effect. Again factors which may be taken into account include the severity of the disease state, general health of the subject, ethinicity, age, weight, and gender of the subject, diet, time and frequency of administration, drug combination(s), reaction sensitivities, experience with other cancer therapies and regimens, and tolerance/response to such therapies and regimens. Long-acting pharmaceutical compositions may be administered every 2, 3 or 4 days, once every week, or once every two weeks depending on half-life and clearance rate of the particular formulation.

The compounds and compositions described herein may be administered to the subject via any drug delivery route known in the art. Although oral or intravenous administration is preferred, nonlimiting examples for routes of administration include ocular, rectal, buccal, topical, nasal, ophthalmic, subcutaneous, intramuscular, intravenous (bolus and infusion), intracerebral, transdermal and pulmonary.

Also falling within the scope described herein are the in vivo metabolic products of the compounds. Such products may result, for example, from the oxidation, reduction, hydrolysis, amidation, esterification and the like of the administered compound, primarily due to enzymatic processes. Accordingly, the compounds described herein include those produced by a process comprising contacting a compound described herein with a mammalian tissue or a mammal for a period of time sufficient to yield a metabolic product thereof.

Such products typically are identified by preparing a radiolabeled (e.g. $C^{14}$ or $H^3$) compound described herein, administering it in a detectable dose (e.g., greater than about 0.5 mg/kg) to a mammal such as rat, mouse, guinea pig, monkey, or to man, allowing sufficient time for metabolism to occur (typically about 30 seconds to 30 hours), and isolating its conversion products from urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites may be done in the same way as conventional drug metabolism studies well-known to those skilled in the art. The conversion products, so long as they are not otherwise found in vivo, are useful in diagnostic assays for therapeutic dosing of the compounds described herein even if they possess no biological activity of their own.

The methods of treating cancer in a subject in need thereof described herein, said methods comprising administering to the subject an effective amount of one or more of the compounds or a form or pharmaceutical composition thereof alone or in combination with one or more additional agents. In another embodiment, one or more compounds or a form or pharmaceutical composition thereof alone or in combination with one or more additional agents may be administered to the subject in combination with a supportive therapy, a pain relief therapy, or other therapy that does not have an effect on cancer.

In some embodiments, one or more compounds or a form thereof and one or more additional agents are administered as the same pharmaceutical composition. In certain embodiments, one or more compounds or a form thereof and one or more additional agents are administered in different pharmaceutical compositions. In certain embodiments, one or more compounds or a form or pharmaceutical composition thereof and one or more additional agents are administered by the same route of administration. In certain embodiments, one or more compounds or a form or pharmaceutical composition thereof and one or more additional agents are administered by different routes of administration.

Additional agents that can be used in a combination product with compounds that down-regulate Bmi-1 protein expression for the treatment of cancer include, but are not limited to, small molecules, synthetic drugs, peptides (including cyclic peptides), polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides), antibodies, synthetic or natural inorganic molecules, mimetic agents, and synthetic or natural organic molecules.

Specific examples of such agents include, but are not limited to, immunomodulatory agents (e.g., interferon), anti-inflammatory agents (e.g., adrenocorticoids, corticosteroids (e.g., beclomethasone, budesonide, flunisolide, fluticasone, triamcinolone, methylprednisolone, prednisolone, prednisone, hydrocortisone), glucocorticoids, steriods, and non-steriodal anti-inflammatory drugs (e.g., aspirin, ibuprofen, diclofenac, and COX-2 inhibitors), pain relievers, leukotreine antagonists (e.g., montelukast, methyl xanthines; zafirlukast, and zileuton), β2-agonists (e.g., albuterol, biterol, fenoterol, isoetharie, metaproterenol, pirbuterol, salbutamol, terbutalin formoterol, salmeterol, and salbutamol terbutaline), anticholinergic agents (e.g., ipratropium bromide and oxitropium bromide), sulphasalazine, penicillamine, dapsone, antihistamines, anti-malarial agents (e.g., hydroxychloroquine), antiviral agents (e.g., nucleoside analogs (e.g., zidovudine, acyclovir, gangcyclovir, vidarabine, idoxuridine, trifluridine, and ribavirin), foscarnet, amantadine, rimantadine, saquinavir, indinavir, ritonavir, and AZT) and antibiotics (e.g., dactinomycin (formerly actinomycin), bleomycin, erythomycin, penicillin, mithramycin, and anthramycin (AMC)).

Specific examples of additional agents include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bisphosphonates (e.g., pamidronate (Aredria), sodium clondronate (Bonefos), zoledronic acid (Zometa), alendronate (Fosamax), etidronate, ibandornate, cimadronate, risedromate, and tiludromate); bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; EphA2 inhibitors; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alpha-2a; interferon alpha-2b; interferon alpha-n1; interferon alpha-n3;

interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; anti-CD2 antibodies; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other examples of treating cancer include treatment with an anti-cancer or anti-proliferative agent wherein the anti-cancer or anti-proliferative agent is selected from, but not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; HMG CoA reductase inhibitors (e.g., atorvastatin, cerivastatin, fluvastatin, lescol, lupitor, lovastatin, rosuvastatin, and simvastatin); hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; LFA-3TIP (Biogen, Cambridge, Mass.; International Publication No. WO 93/0686 and U.S. Pat. No. 6,162,432); liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; micancertched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate;

rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; 5-fluorouracil; leucovorin; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; thalidomide; velaresol; veramine; verdins; verteporfin; vinorelbine; vinxaltine; vorozole; zanoterone; zeniplatin; zilascorb; and zinostatin stimalamer.

In some embodiments, the additional agent used in combination with a compound is an immunomodulatory agent. Non-limiting examples of immunomodulatory agents include proteinaceous agents such as cytokines, peptide mimetics, and antibodies (e.g., human, humanized, chimeric, monoclonal, polyclonal, Fvs, ScFvs, Fab or F(ab)$_2$ fragments or epitope binding fragments), nucleic acid molecules (e.g., antisense nucleic acid molecules and triple helices), cancer molecules, organic compounds, and inorganic compounds. In particular, immunomodulatory agents include, but are not limited to, methotrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunomide), T cell receptor modulators, cytokine receptor modulators, and modulators mast cell modulators.

In one embodiment, the immunomodulatory agent is a chemotherapeutic agent. In an alternative embodiment, the immunomodulatory agent is an immunomodulatory agent other than a chemotherapeutic agent. In some embodiments, the additional agent used described herein is not an immunomodulatory agent.

In some embodiments, the additional agent used in combination with a compound is an anti-angiogenic agent. Non-limiting examples of anti-angiogenic agents include proteins, polypeptides, peptides, fusion proteins, antibodies (e.g., human, humanized, chimeric, monoclonal, polyclonal, Fvs, ScFvs, Fab fragments, F(ab)$_2$ fragments, and antigen-binding fragments thereof) such as antibodies that immunospecifically bind to TNF-α, nucleic acid molecules (e.g., antisense molecules or triple helices), organic molecules, inorganic molecules, and cancer molecules that reduce or inhibit angiogenesis. In other embodiments, the additional agent described herein is not an anti-angiogenic agent.

In some embodiments, the additional agent used in combination with a compound is an anti-inflammatory agent. Non-limiting examples of anti-inflammatory agents include any anti-inflammatory agent, including agents useful in treating inflammatory disorders, well-known to one of skill in the art. Non-limiting examples of anti-inflammatory agents include non-steroidal anti-inflammatory drugs (NSAIDs), steroidal anti-inflammatory drugs, anticholinergics (e.g., atropine sulfate, atropine methylnitrate, and ipratropium bromide (ATROVENT™)), β2-agonists (e.g., abuterol (VENTOLINT™ and PROVENTIL™), bitolterol (TORNALATE™), levalbuterol (XOPONEX™), metaproterenol (ALUPENT™), pirbuterol (MAXAIRT™), terbutlaine (BRETHAIRE™ and BRETHINE™), albuterol (PROVENTILT™, REPETABS™, and VOLMAX™), formoterol (FORADIL AEROLIZER™), and salmeterol (SEREVENTT™ and SEREVENT DISKUS™)), and methylxanthines (e.g., theophylline (UNIPHYL™, THEO-DURT™, SLO-BID™, AND TEHO-42™)). Examples of NSAIDs include, but are not limited to, aspirin, ibuprofen, celecoxib (CELEBREX™), diclofenac (VOLTAREN™), etodolac (LODINE™), fenoprofen (NALFON™), indomethacin (INDOCINT™), ketoralac (TORADOL™), oxaprozin (DAYPRO™), nabumentone (RELAFEN™), sulindac (CLINORIL™), tolmentin (TOLECTIN™), rofecoxib (VIOXX™), naproxen (ALEVE™, NAPROSYN™), ketoprofen (ACTRON™) and nabumetone (RELAFEN™). Such NSAIDs function by inhibiting a cyclooxygenase enzyme (e.g., COX-1 and/or COX-2). Examples of steroidal anti-inflammatory drugs include, but are not limited to, glucocorticoids, dexamethasone (DECADRON™), corticosteroids (e.g., methylprednisolone (MEDROL™)), cortisone, hydrocortisone, prednisone (PREDNISONE™ and DELTA-SONE™), prednisolone (PRELONE™ and PEDI-APRED™), triamcinolone, azulfidine, and inhibitors of eicosanoids (e.g., prostaglandins, thromboxanes, and leukotrienes).

In certain embodiments, the additional agent used is an alkylating agent, a nitrosourea, an antimetabolite, and anthracyclin, a topoisomerase II inhibitor, or a mitotic inhibitor. Alkylating agents include, but are not limited to, busulfan, cisplatin, carboplatin, cholormbucil, cyclophosphamide, ifosfamide, decarbazine, mechlorethamine; mephalen, and themozolomide. Nitrosoureas include, but are not limited to carmustine (BCNU) and lomustine (CCNU). Antimetabolites include but are not limited to 5-fluorouracil, capecitabine, methotrexate, gemcitabine, cytarabine, and fludarabine. Anthracyclins include but are not limited to daunorubicin, doxorubicin, epirubicin, idarubicin, and mitoxantrone. Topoisomerase II inhibitors include, but are not limited to, topotecan, irinotecan, etopiside (VP-16), and teniposide. Mitotic inhibitors include, but are not limited to taxanes (paclitaxel, docetaxel), and the vinca alkaloids (vinblastine, vincristine, and vinorelbine).

In more specific embodiments, the additional agent used includes, and is not limited to aflibercept, amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin (IV and liposomal), docetaxel, doxorubicin (IV and liposomal), enzastaurin, epirubicin, etoposide, fludarabine, fluorouracil (5FU), gemcitabine, gliadel implants, hydroxycarbamide, idarubicin, ifosfamide, imatinib mesylate, irinotecan, lanreotide, lenalidomide, leucovorin, lomustine, melphalan, mercaptopurine, mesna, methotrexate, mitomycin, mitoxantrone, octreotide, oxaliplatin, paclitaxel, pemetrexed, pentostatin, procarbazine, raltitrexed, satraplatin, sorafenib, streptozocin, sunitinib, tegafururacil, temozolomide, teniposide, thalidomide, thiotepa, tioguanine, topotecan, treosulfan, vatalanib, vinblastine, vincristine, vindesine, vinorelbine, ZD6474, monoclonal antibodies (such as bevacizumab, cetuximab, IMC-A12, IMC-1121B, medi-522, rituximab and the like), hormonal agents (such as anastrozole, bicalutamide, buserelin, cyproterone, diethylstilbestrol, exemestane, flutamide, goserelin (breast and prostrate), letrozole, leuprorelin, medroxyprogesterone, megestrol acetate, tamoxifen, toremifene, triptorelin and the like), biological agents (such as interferon, interleukin-12 and the like), angiogenesis inhibitors (such as AE-941, angiostatin, carboxyamidotriazole, cilengitide, endostatin, halofuginone hydrobromide, 2-methoxyestradiol, squalamine lactate, SU6668 and the like), tubulin binding agents (such as combretastatin A4 phosphate and the like), matrix metalloproteinase inhibitors (such as BMS-275291 and the like) and/or serine/threonine/tyrosine kinase inhibitors and an optional nonsteroidal or COX-2 anti-inflammatory agent (such as celecoxib and the like) or corticosteroid (such as prednisone and the like).

In some embodiments, a compound is used in combination with radiation therapy comprising the use of x-rays, gamma rays and other sources of radiation to destroy cancer stem cells and/or cancer cells. In specific embodiments, the radiation therapy is administered as external beam radiation or teletherapy, wherein the radiation is directed from a remote source. In other embodiments, the radiation therapy is administered as internal therapy or brachytherapy wherein a radioactive source is placed inside the body close to cancer stem cells, cancer cells and/or a tumor mass.

Currently available anti-cancer or anti-proliferative agents, their dosage regimens, routes of administration and recommended usage alone or in combination are known in the art and have been described in such literature as the *Physician's Desk Reference* (60$^{th}$ ed., 2006).

Any anti-cancer or anti-proliferative agent or anti-cancer therapy which is known to be useful, or which has been used or is currently being used for the treatment of cancer, can be used in combination with compounds described herein. See, e.g., Gilman et at, Goodman and Gilman's: The Pharmacological Basis of Therapeutics, 10th ed., McGraw-Hill, New York, 2001; The Merck Manual of Diagnosis and Therapy, Berkow, M. D. et al. (eds.), 17th Ed., Merck Sharp & Dohme Research Laboratories, Rahway, N.J., 1999; Cecil Textbook of Medicine, 20th Ed., Bennett and Plum (eds.), W.B. Saunders, Philadelphia, 1996, and Physicians' Desk Reference (61st ed. 1007) for information regarding therapies (e.g., prophylactic or therapeutic agents) which have been or are currently being used for preventing, treating and/or managing cancer.

Pharmaceutical Compositions

The present description is also directed to a pharmaceutical composition comprising a compound of Formula (I) or a pharmaceutically acceptable form thereof in admixture with a pharmaceutically acceptable excipient.

An embodiment described herein includes a pharmaceutical composition made by the process of admixing a compound of Formula (I) or a pharmaceutically acceptable form thereof with a pharmaceutically acceptable excipient. The pharmaceutical composition may also be formulated to achieve a physiologically compatible pH, ranging from about pH 3 to about pH 11.

Another embodiment of the present include the use of a compound of Formula (I) or a pharmaceutically acceptable form thereof in a pharmaceutical composition for treating cancer comprising an effective amount of a compound of Formula (I) or a pharmaceutically acceptable form thereof in admixture with a pharmaceutically acceptable excipient.

As used herein, the term "composition" means a product comprising the specified ingredients in the specified amounts, as well as any product which results, directly or indirectly, from combination of the specified ingredients in the specified amounts.

In another embodiment, the pharmaceutical composition may comprise a combination product of one or more compounds described herein and one or more additional agents useful in the treatment of cancer, such as a chemotherapeutic or biochemotherapeutic agent.

The term "pharmaceutically acceptable excipient" refers to an excipient for administration of a pharmaceutical agent, such as the compounds described herein. The term refers to any pharmaceutical excipient that may be administered without undue toxicity. Pharmaceutically acceptable excipients may be determined in part by the particular composition being administered, as well as by the particular mode of administration and/or dosage form. Nonlimiting examples of pharmaceutically acceptable excipients include carriers, solvents, stabilizers, adjuvants, diluents, etc. Accordingly, there exists a wide variety of suitable formulations of pharmaceutical compositions as described herein (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions described herein may be formulated in any form suitable for the intended method of administration. Suitable formulations for oral administration include solids, liquid solutions, emulsions and suspensions, while suitable inhaleable formulations for pulmonary administration include liquids and powders. Alternative formulations include syrups, creams, ointments, tablets, and lyophilized solids which can be reconstituted with a physiologically compatible solvent prior to administration.

When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In other embodiments, pharmaceutical compositions described herein may be formulated as suspensions comprising a compound of Formula (I) or a form thereof in admixture with at least one pharmaceutically acceptable excipient suitable for the manufacture of a suspension. In yet other embodiments, pharmaceutical compositions described herein may be formulated as dispersible powders and granules suitable for preparation of a suspension by the addition of one or more excipient(s).

Excipients suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions described herein may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions described herein may be in the form of a sterile injectable preparation, such as a sterile injectable aqueous emulsion or oleaginous suspension. Such emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propane-diol. The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or di-glycerides. In addition, fatty acids such as oleic acid may likewise be used in the preparation of injectables.

The compounds described herein may be substantially insoluble in water and sparingly soluble in most pharmaceutically acceptable protic solvents and vegetable oils, but generally soluble in medium-chain fatty acids (e.g., caprylic and capric acids) or triglycerides and in propylene glycol esters of medium-chain fatty acids. Thus contemplated are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In some embodiments, the compound described herein is formulated for oral administration in a lipid-based composition suitable for low solubility compounds. Lipid-based formulations can generally enhance the oral bioavailability of such compounds. As such, pharmaceutical compositions described herein may comprise a effective amount of a compound of Formula (I) or a form thereof, together with at least one pharmaceutically acceptable excipient selected from medium chain fatty acids or propylene glycol esters thereof (e.g., propylene glycol esters of edible fatty acids such as caprylic and capric fatty acids) and pharmaceutically acceptable surfactants, such as polyoxyl 40 hydrogenated castor oil.

In other embodiments, the bioavailability of low solubility compounds may be enhanced using particle size optimization techniques including the preparation of nanoparticles or nanosuspensions using techniques known to those skilled in art. The compound forms present in such preparations include amorphous, partially amorphous, partially crystalline or crystalline forms.

In alternative embodiments, the pharmaceutical composition may further comprise one or more aqueous solubility enhancer(s), such as a cyclodextrin. Nonlimiting examples of cyclodextrin include hydroxypropyl, hydroxyethyl, glucosyl, maltosyl and maltotriosyl derivatives of α-, β-, and γ-cyclodextrin, and hydroxypropyl-β-cyclodextrin (HPBC). In some embodiments, the pharmaceutical composition further comprises HPBC in a range of from about 0.1% to about 20%, from about 1% to about 15%, or from about 2.5% to about 10%. The amount of solubility enhancer employed may depend on the amount of the compound described herein in the composition.

In other embodiments are pharmaceutical compositions wherein one or more compounds of Formula (I) or a form thereof is administered in a combination product with one or more additional agents useful in the treatment of cancer. The skilled artisan will recognize that a variety of active ingredients may be administered in a combination with the compounds described herein whereby the product may act to augment or synergistically enhance the anticancer activity of either or both the additional agent(s) and the compound(s) described herein.

As used herein, the term "synergistic," refers to the effect of the administration of a combination product as described herein which is more effective than the additive effects of any two or more single agents. In a specific embodiment, a synergistic effect of a combination product permits the use of lower dosages of one or more agents and/or less frequent administration of said agents to a subject with cancer. In certain embodiments, the ability to utilize lower dosages of an agent and/or to administer said agents less frequently reduces the toxicity associated with the administration of said agents to a subject without reducing the efficacy of said agents in the prevention or treatment of cancer. In some embodiments, a synergistic effect results in improved efficacy of each of the agents in treating cancer. In some embodiments, a synergistic effect of a combination of agents avoids or reduces adverse or unwanted side effects associated with the use of any single agent. The combination of agents in such a product can be administered to a subject in the same pharmaceutical composition. Alternatively, the agents can be administered concurrently to a subject in separate pharmaceutical compositions. The agents may also be administered to a subject by the same or different routes of administration. In a specific embodiment, at least one of the agents is a compound.

It is also possible to combine any compound described herein with such additional agents useful in the treatment of cancer, including compounds, in a unitary dosage form, or in separate dosage forms intended for simultaneous or sequential administration to a patient in need of treatment. When administered sequentially, the combination may be administered in two or more administrations. In an alternative embodiment, it is possible to administer one or more compounds described herein and one or more additional agents by different routes.

According to the methods described herein, a combination product may include a combination of active ingredients that may be: (1) co-formulated and administered or delivered simultaneously in a combined formulation; (2) delivered by alternation or in parallel as separate formulations; or (3) by any other combination regimen known in the art. When delivered as separate formulations in alternation therapy, the methods described herein may comprise administering or delivering the active ingredients sequentially, e.g., in separate solution, emulsion, suspension, tablets, pills or capsules, or by different injections in separate syringes. In general, when administered in alternation, an effective dosage of each active ingredient is administered sequentially, i.e., serially, whereas in simultaneous administration, effective dosages of two or more active ingredients are administered together. Various sequences of intermittent combination administration may also be used.

General Synthetic Examples

As disclosed herein, methods for preparing the compounds described herein are available via standard, well-known synthetic methodology. Many of the starting materials are commercially available or can be prepared using the routes described below using techniques known to those skilled in the art.

Scheme A

Compounds of Formula (Ib), as described herein, may be prepared as shown in Scheme A below.

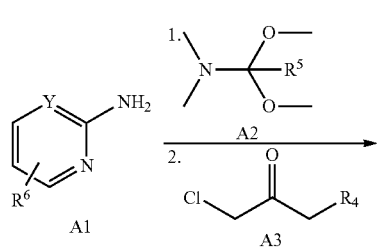

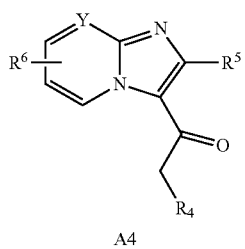

Using ring closure conditions known to those skilled in the art, a Compound A1 is reacted with a Compound A2, followed by reaction with a $R_4$ substituted Compound A3 to provide a keto intermediate Compound A4.

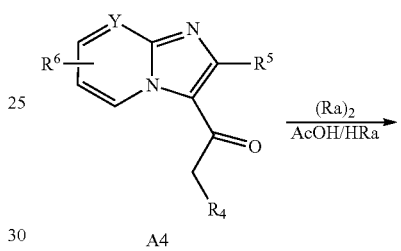

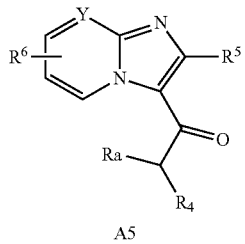

The Compound A4 intermediate is reacted with a halogen (represented by Ra) in the presence of acetic acid and a HRa acid to provide a Compound A5 (wherein Ra represents a halogen atom).

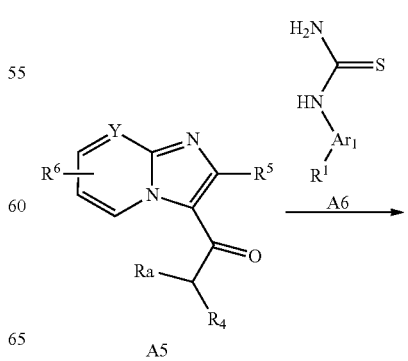

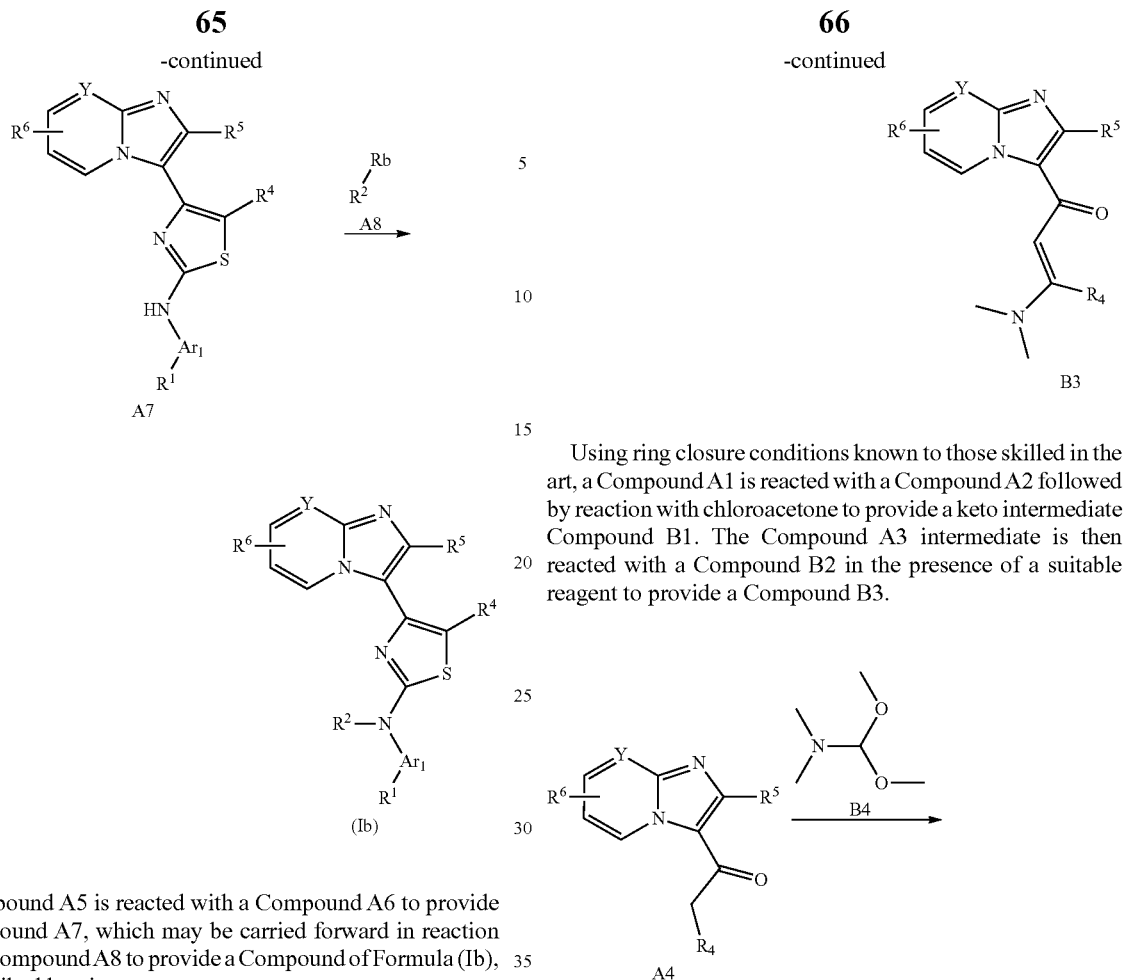

Compound A5 is reacted with a Compound A6 to provide a Compound A7, which may be carried forward in reaction with a Compound A8 to provide a Compound of Formula (Ib), as described herein.

Scheme B

Compounds of Formula (Ic), as described herein, may be prepared as shown in Scheme B below.

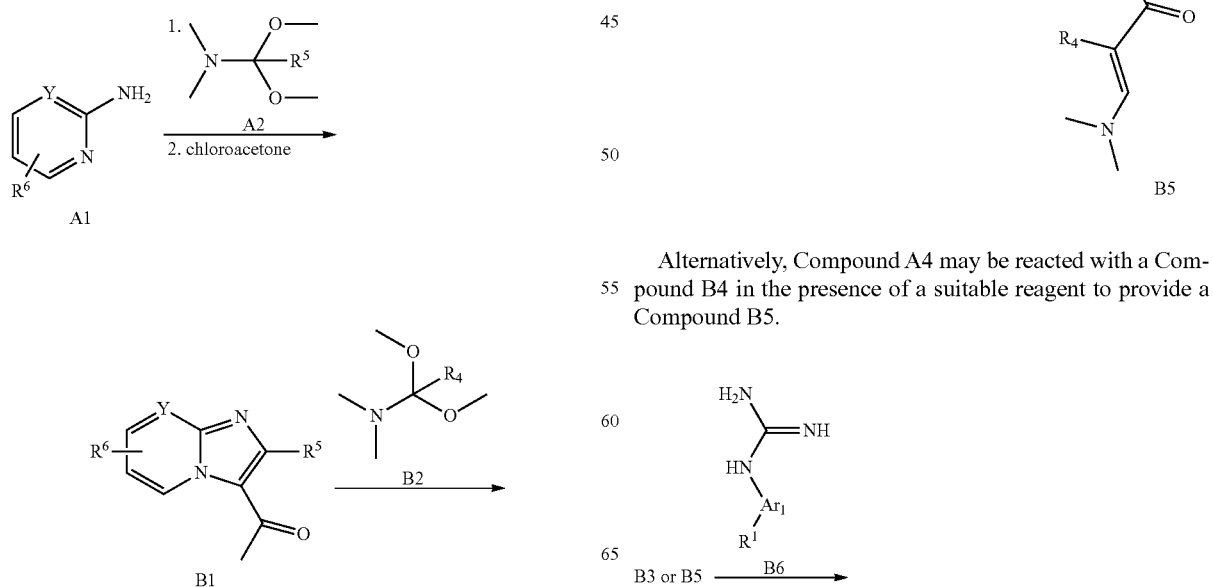

Using ring closure conditions known to those skilled in the art, a Compound A1 is reacted with a Compound A2 followed by reaction with chloroacetone to provide a keto intermediate Compound B1. The Compound A3 intermediate is then reacted with a Compound B2 in the presence of a suitable reagent to provide a Compound B3.

Alternatively, Compound A4 may be reacted with a Compound B4 in the presence of a suitable reagent to provide a Compound B5.

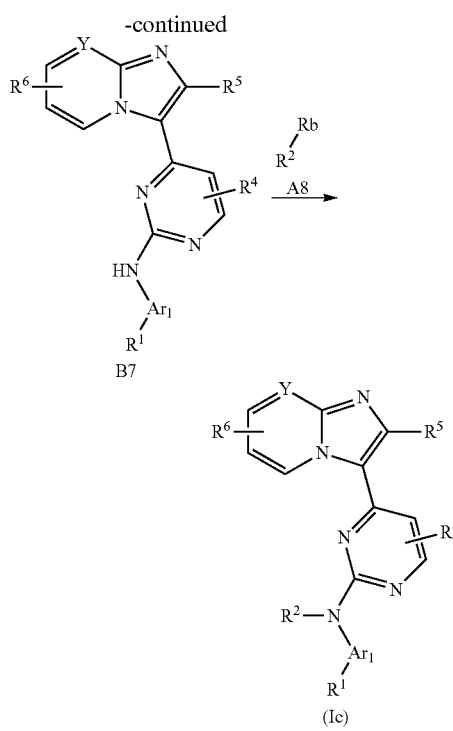

Compound B3 or Compound B5 is reacted with a Compound B6 to provide a Compound B7, which may be carried forward in reaction with a Compound A8 to provide a Compound of Formula (Ic), as described herein.

Specific Synthetic Examples

To assist in understanding the scope of the compounds described herein, the following Specific Examples are included. The experiments relating to the compounds described herein should not, of course, be construed as specifically limiting the scope of the compounds described herein and such variations of the compounds as described herein, now known or later developed, which would be within the purview of one skilled in the art are considered to fall within the scope as described herein and hereinafter claimed.

Other than in the working examples, unless indicated to the contrary, all numbers expressing quantities of ingredients, reaction conditions, experimental data, and so forth used in the specification and claims are to be understood as being modified by the term "about". Accordingly, all such numbers represent approximations that may vary depending upon the desired properties sought to be obtained by a reaction or as a result of variable experimental conditions. Therefore, within an expected range of experimental reproducibility, the term "about" in the context of the resulting data, refers to a range for data provided that may vary according to a standard deviation from the mean. As well, for experimental results provided, the resulting data may be rounded up or down to present data consistently, without loss of significant figures. At the very least, and not as an attempt to limit the application of the doctrine of equivalents to the scope of the claims, each numerical parameter should be construed in light of the number of significant digits and ordinary rounding techniques.

While the numerical ranges and parameters setting forth the broad scope of the compounds described are approximations, the numerical values set forth in the working examples are reported as precisely as possible. Any numerical value, however, inherently contains certain errors necessarily resulting from the standard deviation found in their respective testing measurements.

The compounds provided herein are described in more detail with reference to the following non-limiting examples, which are offered to more fully illustrate the scope of the compounds described herein, but are not to be construed as limiting the scope thereof. The examples illustrate the preparation of certain compounds described herein, and the testing of these compounds in vitro and/or in vivo. Those of skill in the art will understand that the techniques described in these examples represent techniques described by the inventors to function within the practice of those skilled in the chemical arts, and as such constitute preferred modes for the practice thereof. However, it should be appreciated that those of skill in the art should in light of the present disclosure, appreciate that many changes can be made in the specific methods that are disclosed and still obtain a like or similar result without departing from the spirit and scope described herein.

All reactions in the following examples were performed in oven-dried glassware under a nitrogen atmosphere. The reagents and solvents were used as purchased (Sigma-Aldrich, Acros, AlfaAesar, TCI America), except where noted. Chromatographic separations were performed using ISCO CombiFlash® Rf system. NMR spectra were obtained on a Bruker Avance III$^{500}$ spectrometer using DMSO-d$_6$ with TMS or residual solvent as standard. Melting points were determined using a SRS OptiMelt® MPA100 and are uncorrected/uncalibrated. TLC analysis was performed using Aldrich 254 nm glass-backed plates (60 Å, 250 μm) and visualized using UV and I$_2$ stains. Mass spectra were obtained using an ACQUITY UPLC.® System and are shown as ESI.

The following abbreviations are provided to ensure the terms used herein are unambiguous to one skilled in the art:

| Abbreviation | Meaning |
| --- | --- |
| AcOH | acetic acid |
| ESI | electrospray ionization |
| Bu | butyl |
| Cpd | compound |
| DMA | dimethyl acetamide |
| DMF | dimethyl formamide |
| Et | ethyl |
| Et$_2$O | ethoxy ethane/ethyl ether |
| EtOAc | ethyl acetate |
| EtOH | ethanol |
| h | hour(s) |
| Me | methyl |
| MS | mass spec M + H$^+$ (m/e) (unless otherwise indicated) |
| r.t. | room temperature |
| RT | retention time (min) |
| t-Bu | tert-butyl |
| UPLC | Ultra Performance Liquid Chromatography |

Example 1

N-(2,6-dichloro-4-methoxyphenyl)-4-(2-methylimi-dazo[1,2-a]pyrimidin-3-yl)thiazol-2-amine (Cpd 19)

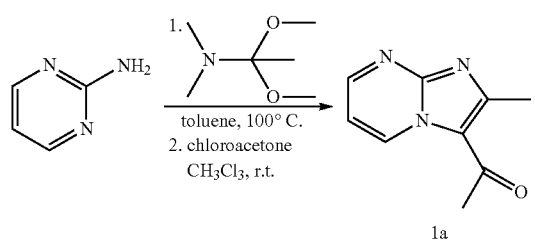

1a

Step A. Preparation of 1-(2-methylimidazo[1,2-a]pyrimidin-3-yl)ethanone

To 3.05 g (32.09 mmol) of 2-aminopyrimidine in 5 mL of dry toluene were added 9.5 mL (64.19 mmol) of N,N-dimethyl acetamide dimethyl ketal. The reaction mixture was heated at 100° C. for 48 h, then cooled down to r.t. and 3.07 mL (38.51 mmol) of chloroacetone were added. After stirring for 12 h at r.t., UPLC showed almost complete consumption of starting material. The solvent was evaporated and the resulting residue was dissolved in 60 mL of $CH_2Cl_2$, washed twice with water, and sequentially with aq. $NaHCO_3$ and brine, then dried over sodium sulfate. The solvent was evaporated and the crude product was purified by recrystallization from EtOAc to yield the title Compound 1a (2.78 g, 49%) as a pale yellow solid.

Step B. Preparation of 2-bromo-1-(2-methylimidazo[1,2-a]pyrimidin-3-yl)ethanone To a solution of Compound 1a (2.0 g, 11.43 mmol) in 20 mL of glacial AcOH and 4 mL of 33% HBr/AcOH was added $Br_2$ (0.59 mL, 11.43 mmol) dropwise. The reaction mixture was stirred for 8 h at r.t. during which a yellow precipitate was formed. After UPLC analysis showed 95% conversion of starting material, the precipitate was filtered and dissolved in ~300 mL of $CH_2Cl_2$, then washed sequentially with aq. $NaHCO_3$ two times, and brine, then dried over $Na_2SO_4$ and concentrated to give the title Compound 1b (1.89 g, 91%) as a pale-yellow solid, which was used in the next step without further purification.

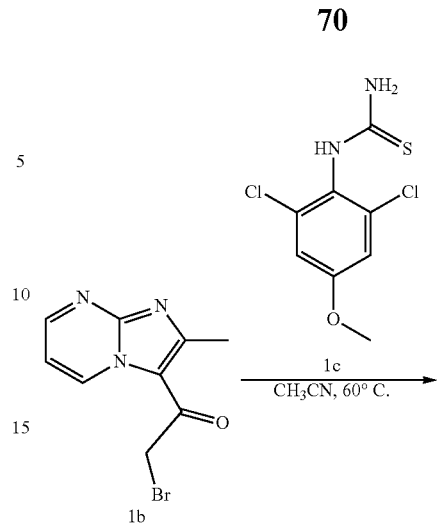

Step C. N-(2,6-dichloro-4-methoxyphenyl)-4-(2-methylimidazo[1,2-a]pyrimidin-3-yl)thiazol-2-amine hydrobromide Compound 1b (74 mg, 0.29 mmol) and Compound 1c (73 mg, 0.29 mmol) in 2 mL of dry $CH_3CN$ were heated at 60° C. for 2 h, after which UPLC showed complete consumption of the starting material. Tan precipitate formed during the reaction was filtered, washed with $CH_3CN$ and dried under reduced pressure to give the HBr salt of title Compound 19 (99 mg, 70%, 100% pure by UPLC); m.p.: 232-240° C.; $^1$H NMR (500 MHz, DMSO-$d_6$) δ 2.64 (s, 3H), 3.85 (s, 3H), 7.27 (s, 2H), 7.34 (brs, 1H), 7.62 (dd, 1H, J=6.8, 4.4 Hz), 8.94 (dd, 1H, J=4.4, 1.7 Hz), 9.47 (dd, 1H, J=6.8, 1.6 Hz), 9.95 (s, 1H); mass spectrum (ESI): m/e (% relative intensity) 405 (100, retention time 0.61, ACQUITY 1 min), 407 (40).

Additional compounds may be prepared according to the procedure of Example 1 by substituting the appropriate starting materials, reagents and reaction conditions and include compounds selected from (wherein the UPLC purity is shown as % value of sample and the retention time (RT) correlates to: [a]UPLC method: ACQUITY 2 min, or [b]UPLC method: ACQUITY 1 min):

| Cpd | Name | MS | RT | UPLC |
|---|---|---|---|---|
| 1 | N-(2,6-dibromo-4-methoxyphenyl)-4-(2-methylimidazo[1,2-a]pyrimidin-3-yl)thiazol-2-amine | 496 | 1.03[a] | 100 |
| 2 | N-(3-chloro-2-methylphenyl)-4-(2-methylimidazo[1,2-a]pyrimidin-3-yl)thiazol-2-amine | 356 | 0.81[b] | 17 |
| 3 | N-(2,5-dimethoxyphenyl)-4-(2-methylimidazo[1,2-a]pyrimidin-3-yl)thiazol-2-amine | 368 | 0.78[b] | 92 |
| 4 | N-(2-ethoxyphenyl)-4-(2-methylimidazo[1,2-a]pyrimidin-3-yl)thiazol-2-amine | 352 | 0.80[b] | 56 |
| 5 | N-(2-chlorophenyl)-4-(2-methylimidazo[1,2-a]pyrimidin-3-yl)thiazol-2-amine | 342 | 1.01[a] | 94 |
| 6 | 4-(2-methylimidazo[1,2-a]pyrimidin-3-yl)-N-m-tolylthiazol-2-amine | 322 | 0.64[b] | 98 |
| 7 | N,N-diethyl-N'-(4-(2-methylimidazo[1,2-a]pyrimidin-3-yl)thiazol-2-yl)benzene-1,4-diamine | 379 | 0.66[a] | 100 |
| 8 | N-(2-methoxyphenyl)-4-(2-methylimidazo[1,2-a]pyrimidin-3-yl)thiazol-2-amine | 338 | 0.61[b] | 100 |
| 9 | 1-(3-(4-(2-methylimidazo[1,2-a]pyrimidin-3-yl)thiazol-2-ylamino)phenyl)ethanone | 350 | 0.76[b] | 97 |
| 10 | 4-(4-(2-methylimidazo[1,2-a]pyrimidin-3-yl)thiazol-2-ylamino)benzenesulfonamide | 387 | 0.74[a] | 92 |
| 11 | N-(4-(4-(2-methylimidazo[1,2-a]pyrimidin-3-yl)thiazol-2-ylamino)phenyl)acetamide | 365 | 0.74[a] | 91 |
| 12 | N,N-dimethyl-N'-(4-(2-methylimidazo[1,2-a]pyrimidin-3-yl)thiazol-2-yl)benzene-1,4-diamine | 351 | 0.58[a] | 100 |
| 13 | N-(4-ethoxyphenyl)-4-(2-methylimidazo[1,2-a]pyrimidin-3-yl)thiazol-2-amine | 352 | 0.79[b] | 100 |
| 14 | N-(4-methoxyphenyl)-4-(2-methylimidazo[1,2-a]pyrimidin-3-yl)thiazol-2-amine | 338 | 1.26[a] | 100 |
| 15 | 4-(4-(2-methylimidazo[1,2-a]pyrimidin-3-yl)thiazol-2-ylamino)benzoic acid | 352 | 0.82[a] | 95 |
| 16 | 4-(4-(2,7-dimethylimidazo[1,2-a]pyridin-3-yl)thiazol-2-ylamino)phenol | 337 | 0.75[b] | 84 |
| 17 | 4-(2,7-dimethylimidazo[1,2-a]pyridin-3-yl)-N-(4-methoxyphenyl)thiazol-2-amine | 351 | 0.77[b] | 85 |
| 18 | 4-(2,7-dimethylimidazo[1,2-a]pyridin-3-yl)-N-(2-methoxyphenyl)thiazol-2-amine | 351 | 0.77[b] | 68 |
| 20 | N-(2,6-difluoro-4-methoxyphenyl)-4-(2-methylimidazo[1,2-a]pyrimidin-3-yl)thiazol-2-amine | 374 | 0.95[a] | 93 |
| 21 | N-(2,6-dibromo-4-methylphenyl)-4-(2-methylimidazo[1,2-a]pyrimidin-3-yl)thiazol-2-amine | 480 | 0.76[b] | 100 |
| 22 | 4-(2-methylimidazo[1,2-a]pyrimidin-3-yl)-N-(2,4,6-tribromophenyl)thiazol-2-amine | 545 | 0.69[a] | 100 |
| 23 | N-(2,6-dibromo-4-(2-methoxyethoxy)phenyl)-4-(2-methylimidazo[1,2-a]pyrimidin-3-yl)thiazol-2-amine | 540 | 1.03[a] | 94 |
| 24 | 4-(6-chloroimidazo[1,2-a]pyridin-3-yl)-N-(2,6-dibromo-4-methoxyphenyl)thiazol-2-amine | 515 | 1.10[a] | 100 |
| 25 | 4-(6-chloroimidazo[1,2-a]pyridin-3-yl)-N-(2,6-dibromo-4-methylphenyl)thiazol-2-amine | 499 | 0.81[b] | 100 |
| 26 | 4-(6-chloroimidazo[1,2-a]pyridin-3-yl)-N-(2,6-dichloro-4-methoxyphenyl)thiazol-2-amine | 427 | 0.76[a] | 96 |
| 27 | 4-(6-chloroimidazo[1,2-a]pyridine-3-yl)-N-(4-methoxy-2,6-dimethylphenyl)thiazol-2-amine | 385 | 0.82[b] | 100 |
| 29 | 4-(6-chloro-2-methylimidazo[1,2-a]pyridin-3-yl)-N-(4-iodophenyl)thiazol-2-amine | 466 | 1.18[a] | 97 |
| 30 | N-(benzo[d][1,3]dioxol-5-yl)-4-(6-chloro-2-methylimidazo[1,2-a]pyridin-3-yl)thiazol-2-amine | 384 | 0.99[a] | 96 |
| 31 | 3-{[4-(2,7-dimethylimidazo[1,2-a]pyridin-3-yl)-1,3-thiazol-2-yl]amino}phenol hydrobromide | 337 | 0.97[a] | 92 |
| 32 | 4-(2,7-dimethylimidazo[1,2-a]pyridin-3-yl)-N-(4-methylphenyl)-1,3-thiazol-2-amine | 335 | 1.13[a] | 96 |
| 33 | 1-(4-{[4-(2,7-dimethylimidazo[1,2-a]pyridin-3-yl)-1,3-thiazol-2-yl]amino}phenyl)ethanone | 363 | 1.07[a] | 95 |
| 34 | 1-(4-{[4-(2-methylimidazo[1,2-a]pyrimidin-3-yl)-1,3-thiazol-2-yl]amino}phenyl)ethanone | 350 | 1.6[a] | 95 |
| 35 | 3-{[4-(2-methylimidazo[1,2-a]pyridin-3-yl)-1,3-thiazol-2-yl]amino}phenol hydrobromide | 323 | 0.79[a] | 94 |
| 36 | 4-{[4-(2-methylimidazo[1,2-a]pyridine-3-yl)-1,3-thiazol-2-yl]amino}phenol hydrobromide | 323 | 0.76[a] | 90 |
| 37 | N-(1,3-benzodioxol-5-yl)-4-(2-methylimidazo[1,2-a]pyrimidin-3-yl)-1,3-thiazol-2-amine hydrobromide | 352 | 0.91[a] | 94 |
| 38 | N-(2,6-dichlorophenyl)-4-(2-methylimidazo[1,2-a]pyrimidin-3-yl)-1,3-thiazol-2-amine hydrobromide | 376, 378 | 0.98[a] | 97 |
| 39 | N-(4-iodophenyl)-4-(2-methylimidazo[1,2-a]pyrimidin-3-yl)-1,3-thiazol-2-amine hydrobromide | 434 | 1.10[a] | 90 |
| 40 | N-(1,3-benzodioxol-5-yl)-N-methyl-4-(2-methylimidazo[1,2-a]pyrimidin-3-yl)-1,3-thiazol-2-amine | 366 | 1.02[a] | 87 |
| 41 | N,N-dimethyl-N'-[4-(2-methylimidazo[1,2-a]pyridin-3-yl)-1,3-thiazol-2-yl]benzene-1,4-diamine hydrobromide | 350 | 0.67[a] | 100 |

-continued

| Cpd | Name | MS | RT | UPLC |
|---|---|---|---|---|
| 44 | N-(4-methoxyphenyl)-4-(2-methylimidazo[1,2-a]pyridin-3-yl)-1,3-thiazol-2-amine hydrobromide | 338 | 0.83[a] | 96 |
| 45 | N-(3-fluoro-4-methoxyphenyl)-4-(2-methylimidazo[1,2-a]pyrimidin-3-yl)-1,3-thiazol-2-amine hydrobromide | 356 | 0.96[a] | 100 |
| 46 | N-(3-chloro-4-methoxyphenyl)-4-(2-methylimidazo[1,2-a]pyrimidin-3-yl)-1,3-thiazol-2-amine hydrobromide | 372 | 1.02[a] | 94 |
| 48 | N-(4-bromophenyl)-4-(2-methylimidazo[1,2-a]pyrimidin-3-yl)-1,3-thiazol-2-amine hydrobromide | 386, 388 | 1.05[a] | 100 |
| 49 | N-(4-chlorophenyl)-4-(2-methylimidazo[1,2-a]pyrimidin-3-yl)-1,3-thiazol-2-amine hydrobromide | 342, 344 | 1.03[a] | 100 |
| 50 | N-(3-chloro-4-methoxyphenyl)-4-(2-methylimidazo[1,2-a]pyridin-3-yl)-1,3-thiazol-2-amine hydrobromide | 371 | 1.00[a] | 97 |
| 51 | N-(3-fluoro-4-methoxyphenyl)-4-(2-methylimidazo[1,2-a]pyridin-3-yl)-1,3-thiazol-2-amine hydrobromide | 355 | 0.95[a] | 100 |
| 52 | N-[4-(2-methoxyethoxy)phenyl]-4-(2-methylimidazo[1,2-a]pyridin-3-yl)-1,3-thiazol-2-amine hydrobromide | 381 | 0.92[a] | 95 |
| 53 | N-(4-iodophenyl)-4-(2-methylimidazo[1,2-a]pyridin-3-yl)-1,3-thiazol-2-amine hydrobromide | 433 | 1.08[a] | 90 |
| 54 | N-[2,6-dibromo-4-(2-methoxyethoxy)phenyl]-4-(2-methylimidazo[1,2-a]pyridin-3-yl)-1,3-thiazol-2-amine hydrobromide | 538 | 1.01[a] | 98 |
| 55 | 1-(4-{[4-(2-methylimidazo[1,2-a]pyridin-3-yl)-1,3-thiazol-2-yl]amino}phenyl)ethanone hydrobromide | 349 | 0.85[a] | 97 |
| 56 | N-(1,3-benzodioxol-5-yl)-4-(2-methylimidazo[1,2-a]pyridin-3-yl)-1,3-thiazol-2-amine hydrobromide | 351 | 0.92[a] | 100 |
| 57 | N-(2,6-difluoro-4-methoxyphenyl)-4-(2-methylimidazo[1,2-a]pyridin-3-yl)-1,3-thiazol-2-amine hydrobromide | 373 | 0.94[a] | 93 |
| 58 | N'-[4-(6-chloro-2-methylimidazo[1,2-a]pyridin-3-yl)-1,3-thiazol-2-yl]-N,N-dimethylbenzene-1,4-diamine hydrobromide | 384 | 0.80[a] | 100 |
| 59 | 4-(6-chloro-2-methylimidazo[1,2-a]pyridin-3-yl)-N-(4-methoxyphenyl)-1,3-thiazol-2-amine hydrobromide | 371 | 1.02[a] | 100 |
| 60 | 4-(6-chloro-2-methylimidazo[1,2-a]pyridin-3-yl)-N-(4-chlorophenyl)-1,3-thiazol-2-amine hydrobromide | 375, 377 | 1.13[a] | 97 |
| 61 | N-(4-bromophenyl)-4-(6-chloro-2-methylimidazo[1,2-a]pyridin-3-yl)-1,3-thiazol-2-amine hydrobromide | 419, 421 | 1.15[a] | 98 |
| 62 | 1-(4-{[4-(6-chloro-2-methylimidazo[1,2-a]pyridin-3-yl)-1,3-thiazol-2-yl]amino}phenyl)ethanone hydrobromide | 383 | 0.96[a] | 96 |
| 63 | N-(1,3-benzodioxol-5-yl)-4-(2,7-dimethylimidazo[1,2-a]pyridin-3-yl)-1,3-thiazol-2-amine hydrobromide | 365 | 0.91[a] | 99 |
| 64 | N'-[4-(2,7-dimethylimidazo[1,2-a]pyridin-3-yl)-1,3-thiazol-2-yl]-N,N-dimethylbenzene-1,4-diamine hydrobromide | 364 | 0.75[a] | 100 |
| 65 | N-(4-chlorophenyl)-4-(2,7-dimethylimidazo[1,2-a]pyridin-3-yl)-1,3-thiazol-2-amine hydrobromide | 355 | 1.03[a] | 95 |
| 66 | 4-(2,7-dimethylimidazo[1,2-a]pyridin-3-yl)-N-(3-fluoro-4-methoxyphenyl)-1,3-thiazol-2-amine hydrobromide | 369 | 0.95[a] | 100 |
| 67 | N-(3-chloro-4-methoxyphenyl)-4-(2,7-dimethylimidazo[1,2-a]pyridin-3-yl)-1,3-thiazol-2-amine hydrobromide | 385 | 1.02[a] | 100 |
| 68 | N-(4-bromophenyl)-4-(2,7-dimethylimidazo[1,2-a]pyridin-3-yl)-1,3-thiazol-2-amine hydrobromide | 399, 401 | 1.05[a] | 94 |
| 69 | 4-(2,7-dimethylimidazo[1,2-a]pyridin-3-yl)-N-(4-iodophenyl)-1,3-thiazol-2-amine hydrobromide | 447 | 1.07[a] | 100 |
| 70 | N'-[4-(2,6-dimethylimidazo[1,2-a]pyridin-3-yl)-1,3-thiazol-2-yl]-N,N-dimethylbenzene-1,4-diamine hydrobromide | 364 | 0.76[a] | 93 |
| 71 | 4-(2,6-dimethylimidazo[1,2-a]pyridin-3-yl)-N-(4-methoxyphenyl)-1,3-thiazol-2-amine hydrobromide | 351 | 0.98[a] | 100 |
| 72 | N-(1,3-benzodioxol-5-yl)-4-(2,6-dimethylimidazo[1,2-a]pyridin-3-yl)-1,3-thiazol-2-amine hydrobromide | 365 | 0.97[a] | 97 |
| 73 | N-(3-chloro-4-methoxyphenyl)-4-(2,6-dimethylimidazo[1,2-a]pyridin-3-yl)-1,3-thiazol-2-amine hydrobromide | 385 | 1.00[a] | 100 |
| 74 | 4-(2,6-dimethylimidazo[1,2-a]pyridin-3-yl)-N-[4-(2-methoxyethoxy)phenyl]-1,3-thiazol-2-amine hydrobromide | 395 | 0.96[a] | 98 |
| 75 | N'-[4-(2,6-dimethylimidazo[1,2-a]pyridin-3-yl)-1,3-thiazol-2-yl]-N,N-diethylbenzene-1,4-diamine hydrobromide | 392 | 0.73[a] | 98 |
| 76 | 4-(2,6-dimethylimidazo[1,2-a]pyridin-3-yl)-N-(4-iodophenyl)-1,3-thiazol-2-amine hydrobromide | 447 | 1.07[a] | 91 |
| 77 | N-(4-bromophenyl)-4-(2,6-dimethylimidazo[1,2-a]pyridin-3-yl)-1,3-thiazol-2-amine hydrobromide | 399, 401 | 1.06[a] | 91 |
| 78 | N-(4-chlorophenyl)-4-(2,6-dimethylimidazo[1,2-a]pyridin-3-yl)-1,3-thiazol-2-amine hydrobromide | 355 | 1.03[a] | 90 |
| 79 | 4-(imidazo[1,2-a]pyridin-3-yl)-N-(4-iodophenyl)-1,3-thiazol-2-amine hydrobromide | 419 | 0.98[a] | 100 |
| 80 | N-(4-bromophenyl)-N-methyl-4-(2-methylimidazo[1,2-a]pyrimidin-3-yl)-1,3-thiazol-2-amine | 400, 402 | 1.08[a] | 90 |
| 81 | N'-[4-(6-bromo-2-methylimidazo[1,2-a]pyridin-3-yl)-1,3-thiazol-2-yl]-N,N-dimethylbenzene-1,4-diamine hydrobromide | 428, 430 | 0.71[a] | 100 |
| 82 | N-(1,3-benzodioxol-5-yl)-4-(6-bromo-2-methylimidazo[1,2-a]pyridin-3-yl)-1,3-thiazol-2-amine hydrobromide | 431 | 0.94[a] | 100 |

-continued

| Cpd | Name | MS | RT | UPLC |
|---|---|---|---|---|
| 83 | 4-(imidazo[1,2-a]pyrimidin-3-yl)-N-(4-iodophenyl)-1,3-thiazol-2-amine hydrobromide | 420 | 1.06[a] | 97 |
| 84 | N-(3,4-dimethoxyphenyl)-4-(2-methylimidazo[1,2-a]pyrimidin-3-yl)-1,3-thiazol-2-amine hydrobromide | 369 | 0.78[a] | 100 |
| 85 | 4-(2-methylimidazo[1,2-a]pyrimidin-3-yl)-N-(4-methylphenyl)-1,3-thiazol-2-amine hydrobromide | 321, 323 | 0.94 | 100 |
| 86 | N-(4-ethylphenyl)-4-(2-methylimidazo[1,2-a]pyrimidin-3-yl)-1,3-thiazol-2-amine hydrobromide | 337 | 1.02[a] | 100 |
| 87 | 4-(2-methylimidazo[1,2-a]pyrimidin-3-yl)-N-[4-(propan-2-yl)phenyl]-1,3-thiazol-2-amine hydrobromide | 351 | 1.07[a] | 100 |
| 88 | 4-(6-chloro-2-methylimidazo[1,2-a]pyridin-3-yl)-N-(4-ethoxyphenyl)-1,3-thiazol-2-amine hydrobromide | 386 | 1.04[a] | 100 |
| 89 | 4-(6-chloro-2-methylimidazo[1,2-a]pyridin-3-yl)-N-(4-methylphenyl)-1,3-thiazol-2-amine hydrobromide | 356 | 1.07[a] | 100 |
| 90 | 4-(6-chloro-2-methylimidazo[1,2-a]pyridin-3-yl)-N-(4-ethylphenyl)-1,3-thiazol-2-amine hydrobromide | 369 | 1.15[a] | 100 |
| 91 | 4-(6-chloro-2-methylimidazo[1,2-a]pyridin-3-yl)-N-[4-(propan-2-yl)phenyl]-1,3-thiazol-2-amine hydrobromide | 384 | 1.20[a] | 100 |
| 92 | 4-{[4-(6-chloro-2-methylimidazo[1,2-a]pyridin-3-yl)-1,3-thiazol-2-yl]amino}phenol hydrobromide | 357 | 0.79[a] | 100 |
| 93 | 4-(6-chloro-2-methylimidazo[1,2-a]pyridin-3-yl)-N-[4-(2-methoxyethoxy)phenyl]-1,3-thiazol-2-amine hydrobromide | 416 | 1.15[a] | 100 |
| 94 | 3-[2-(1,3-benzodioxol-5-ylamino)-1,3-thiazol-4-yl]-2-methylimidazo[1,2-a]pyridin-8-ol hydrobromide | 367 | 0.84[a] | 96 |
| 95 | N-(3-chloro-4-methoxyphenyl)-4-(6-chloro-2-methylimidazo[1,2-a]pyridin-3-yl)-1,3-thiazol-2-amine hydrobromide | 406 | 1.01[a] | 100 |
| 96 | 4-(6-chloro-2-methylimidazo[1,2-a]pyridin-3-yl)-N-(3-fluoro-4-methoxyphenyl)-1,3-thiazol-2-amine hydrobromide | 389 | 0.96[a] | 100 |
| 97 | N-(4-{[4-(6-chloro-2-methylimidazo[1,2-a]pyridin-3-yl)-1,3-thiazol-2-yl]amino}phenyl)acetamide hydrobromide | 398 | 0.76[a] | 100 |
| 98 | 4-(6-chloro-2-methylimidazo[1,2-a]pyridin-3-yl)-N-(2,6-dichlorophenyl)-1,3-thiazol-2-amine hydrobromide | 410 | 1.17[a] | 100 |
| 99 | 1-(4-{[4-(6-bromo-2-methylimidazo[1,2-a]pyridin-3-yl)-1,3-thiazol-2-yl]amino}phenyl)ethanone hydrobromide | 427, 429 | 0.87[a] | 91 |
| 100 | 4-(6-bromo-2-methylimidazo[1,2-a]pyridin-3-yl)-N-(4-chlorophenyl)-1,3-thiazol-2-amine hydrobromide | 419, 421 | 1.07[a] | 98 |
| 101 | 4-(6-bromo-2-methylimidazo[1,2-a]pyridin-3-yl)-N-(4-iodophenyl)-1,3-thiazol-2-amine hydrobromide | 511, 513 | 1.13[a] | 100 |
| 102 | 4-(6-bromo-2-methylimidazo[1,2-a]pyridin-3-yl)-N-(4-bromophenyl)-1,3-thiazol-2-amine hydrobromide | 465 | 1.09[a] | 100 |
| 103 | 4-(6-bromo-2-methylimidazo[1,2-a]pyridin-3-yl)-N-(3-chloro-4-methoxyphenyl)-1,3-thiazol-2-amine hydrobromide | 451 | 1.00[a] | 100 |
| 104 | 4-(6-bromo-2-methylimidazo[1,2-a]pyridin-3-yl)-N-(3-fluoro-4-methoxyphenyl)-1,3-thiazol-2-amine hydrobromide | 433, 435 | 0.97[a] | 100 |
| 105 | 4-(6-chloroimidazo[1,2-a]pyridin-3-yl)-N-(4-methoxyphenyl)-1,3-thiazol-2-amine hydrobromide | 357 | 1.02[a] | 100 |
| 106 | N'-[4-(6-chloroimidazo[1,2-a]pyridin-3-yl)-1,3-thiazol-2-yl]-N,N-dimethylbenzene-1,4-diamine hydrobromide | 370 | 0.71[a] | 100 |
| 107 | 1-(4-{[4-(6-chloroimidazo[1,2-a]pyridin-3-yl)-1,3-thiazol-2-yl]amino}phenyl)ethanone hydrobromide | 369 | 0.91[a] | 96 |
| 108 | 4-(6-chloroimidazo[1,2-a]pyridin-3-yl)-N-(4-iodophenyl)-1,3-thiazol-2-amine hydrobromide | 453 | 1.24[a] | 95 |
| 109 | 4-(6-chloroimidazo[1,2-a]pyridin-3-yl)-N-(3-chloro-4-methoxyphenyl)-1,3-thiazol-2-amine hydrobromide | 391, 393 | 0.70[a] | 100 |
| 110 | 4-(6-chloroimidazo[1,2-a]pyridin-3-yl)-N-(3-fluoro-4-methoxyphenyl)-1,3-thiazol-2-amine hydrobromide | 375 | 1.03[a] | 100 |
| 111 | 4-(6-chloro-2-methylimidazo[1,2-a]pyridin-3-yl)-N-(3,4-dichlorophenyl)-1,3-thiazol-2-amine hydrobromide | 409, 411 | 0.75[b] | 100 |
| 112 | N-(4-tert-butylphenyl)-4-(6-chloro-2-methylimidazo[1,2-a]pyridin-3-yl)-1,3-thiazol-2-amine hydrobromide | 397 | 0.66[b] | 100 |
| 121 | N-(4-bromophenyl)-5-methyl-4-(2-methylimidazo[1,2-a]pyrimidin-3-yl)-1,3-thiazol-2-amine hydrobromide | 400, 402 | 0.65[b] | 95 |
| 122 | N-(4-iodophenyl)-5-methyl-4-(2-methylimidazo[1,2-a]pyrimidin-3-yl)-1,3-thiazol-2-amine hydrobromide | 448 | 0.69[b] | 100 |
| 132 | N-(4-bromo-2-chlorophenyl)-4-(6-chloro-2-methylimidazo[1,2-a]pyridin-3-yl)-1,3-thiazol-2-amine hydrobromide | 454, 456 | 0.84[b] | 96 |
| 133 | 4-(6-chloro-2-methylimidazo[1,2-a]pyridin-3-yl)-N-phenyl-1,3-thiazol-2-amine hydrobromide | 341 | 0.69[b] | 100 |
| 134 | 4-(6-chloroimidazo[1,2-a]pyridin-3-yl)-N-[2,6-dibromo-4-(2-methoxyethoxy)phenyl]-1,3-thiazol-2-amine hydrobromide | 559 | 0.75[b] | 100 |
| 135 | 4-(6-chloroimidazo[1,2-a]pyridin-3-yl)-N-(2,4,6-tribromophenyl)-1,3-thiazol-2-amine hydrobromide | 563, 565 | 0.87[b] | 100 |
| 136 | 4-(6-chloroimidazo[1,2-a]pyridin-3-yl)-N-(2,4,6-trichlorophenyl)-1,3-thiazol-2-amine hydrobromide | 431 | 0.83[b] | 100 |
| 144 | 4-(2-ethylimidazo[1,2-a]pyrimidin-3-yl)-N-(4-methoxyphenyl)-1,3-thiazol-2-amine hydrobromide | 352 | 0.67[b] | 100 |

-continued

| Cpd | Name | MS | RT | UPLC |
|---|---|---|---|---|
| 145 | N'-[4-(2-ethylimidazo[1,2-a]pyrimidin-3-yl)-1,3-thiazol-2-yl]-N,N-dimethylbenzene-1,4-diamine hydrobromide | 365 | 0.51[b] | 97 |
| 146 | N-(2,6-dibromo-4-methoxyphenyl)-4-(2-ethylimidazo[1,2-a]pyrimidin-3-yl)-1,3-thiazol-2-amine hydrobromide | 510 | 0.75[a] | 100 |
| 147 | N-(4-chlorophenyl)-4-(2-ethylimidazo[1,2-a]pyrimidin-3-yl)-1,3-thiazol-2-amine hydrobromide | 356 | 0.75[a] | 100 |
| 148 | N-(4-bromophenyl)-4-(2-ethylimidazo[1,2-a]pyrimidin-3-yl)-1,3-thiazol-2-amine hydrobromide | 400, 402 | 0.76[a] | 100 |
| 149 | 4-(2-ethylimidazo[1,2-a]pyrimidin-3-yl)-N-(4-iodophenyl)-1,3-thiazol-2-amine hydrobromide | 448 | 0.78[b] | 100 |
| 150 | 1-(4-{[4-(2-ethylimidazo[1,2-a]pyrimidin-3-yl)-1,3-thiazol-2-yl]amino}phenyl)ethanone hydrobromide | 364 | 0.62[b] | 100 |
| 151 | N-(1,3-benzodioxol-5-yl)-4-(2-ethylimidazo[1,2-a]pyrimidin-3-yl)-1,3-thiazol-2-amine hydrobromide | 366 | 0.66[b] | 100 |
| 152 | 4-(2-ethylimidazo[1,2-a]pyrimidin-3-yl)-N-(3-fluoro-4-methoxyphenyl)-1,3-thiazol-2-amine hydrobromide | 370 | 0.69[b] | 100 |
| 153 | N-(3-chloro-4-methoxyphenyl)-4-(2-ethylimidazo[1,2-a]pyrimidin-3-yl)-1,3-thiazol-2-amine hydrobromide | 386 | 0.72[b] | 100 |
| 154 | N-(1,3-benzodioxol-5-yl)-4-[2-(trifluoromethyl)imidazo[1,2-a]pyrimidin-3-yl]-1,3-thiazol-2-amine | 406 | 0.92[b] | 100 |
| 155 | N-(3-fluoro-4-methoxyphenyl)-4-(6-fluoro-2-methylimidazo[1,2-a]pyridin-3-yl)-1,3-thiazol-2-amine hydrobromide | 373 | 0.59[b] | 100 |
| 156 | 4-(6-fluoro-2-methylimidazo[1,2-a]pyridine-3-yl)-N-(4-iodophenyl)-1,3-thiazol-2-amine hydrobromide | 451 | 0.68[b] | 100 |
| 157 | N'-[4-(6-fluoro-2-methylimidazo[1,2-a]pyridin-3-yl)-1,3-thiazol-2-yl]-N,N-dimethylbenzene-1,4-diamine hydrobromide | 368 | 0.44[b] | 100 |
| 158 | N-(1,3-benzodioxol-5-yl)-4-(6-fluoro-2-methylimidazo[1,2-a]pyridin-3-yl)-1,3-thiazol-2-amine hydrobromide | 369 | 0.57[b] | 100 |
| 159 | 1-(4-{[4-(6-fluoro-2-methylimidazo[1,2-a]pyridin-3-yl)-1,3-thiazol-2-yl]amino}phenyl)ethanone hydrobromide | 367 | 0.53[b] | 100 |
| 160 | 4-(6-fluoro-2-methylimidazo[1,2-a]pyridin-3-yl)-N-(4-methoxyphenyl)-1,3-thiazol-2-amine hydrobromide | 355 | 0.58[b] | 100 |
| 161 | N-(4-chlorophenyl)-4-(6-fluoro-2-methylimidazo[1,2-a]pyridin-3-yl)-1,3-thiazol-2-amine hydrobromide | 359 | 0.65[b] | 100 |
| 162 | N-(4-bromophenyl)-4-(6-fluoro-2-methylimidazo[1,2-a]pyridin-3-yl)-1,3-thiazol-2-amine hydrobromide | 404 | 0.67[b] | 100 |
| 163 | N-(4-ethoxyphenyl)-4-(6-fluoro-2-methylimidazo[1,2-a]pyridin-3-yl)-1,3-thiazol-2-amine hydrobromide | 369 | 0.63[b] | 100 |
| 164 | N-(4-tert-butylphenyl)-4-(6-fluoro-2-methylimidazo[1,2-a]pyridin-3-yl)-1,3-thiazol-2-amine hydrobromide | 381 | 0.74[b] | 100 |
| 165 | N-(4-bromo-2-chlorophenyl)-4-(6-fluoro-2-methylimidazo[1,2-a]pyridin-3-yl)-1,3-thiazol-2-amine hydrobromide | 438 | 0.74[b] | 100 |
| 171 | N-(3-fluoro-4-methoxyphenyl)-4-(2-propylimidazo[1,2-a]pyridin-3-yl)-1,3-thiazol-2-amine trifluoroacetate | 383 | 0.62[b] | 100 |
| 172 | N-(3-chloro-4-methoxyphenyl)-4-(2-propylimidazo[1,2-a]pyridin-3-yl)-1,3-thiazol-2-amine trifluoroacetate | 399 | 0.64[b] | 100 |
| 173 | N-(4-ethoxyphenyl)-4-(2-propylimidazo[1,2-a]pyridin-3-yl)-1,3-thiazol-2-amine trifluoroacetate | 379 | 0.63[b] | 100 |
| 174 | N-(4-iodophenyl)-4-(2-propylimidazo[1,2-a]pyridin-3-yl)-1,3-thiazol-2-amine trifluoroacetate | 461 | 0.68[b] | 100 |
| 175 | N-(1,3-benzodioxol-5-yl)-4-(2-propylimidazo[1,2-a]pyridin-3-yl)-1,3-thiazol-2-amine trifluoroacetate | 379 | 0.60[b] | 100 |
| 176 | N,N-dimethyl-N'-[4-(2-propylimidazo[1,2-a]pyridin-3-yl)-1,3-thiazol-2-yl]benzene-1,4-diamine trifluoroacetate | 378 | 0.47[b] | 100 |
| 177 | 1-(4-{[4-(2-propylimidazo[1,2-a]pyridin-3-yl)-1,3-thiazol-2-yl]amino}phenyl)ethanone trifluoroacetate | 377 | 0.60[b] | 100 |
| 178 | N-(4-chlorophenyl)-4-(2-propylimidazo[1,2-a]pyridin-3-yl)-1,3-thiazol-2-amine trifluoroacetate | 369 | 0.65[b] | 100 |
| 179 | N-(4-bromophenyl)-4-(2-propylimidazo[1,2-a]pyridin-3-yl)-1,3-thiazol-2-amine trifluoroacetate | 414 | 0.68[b] | 100 |
| 180 | N-(4-methoxyphenyl)-4-(2-propylimidazo[1,2-a]pyridin-3-yl)-1,3-thiazol-2-amine trifluoroacetate | 365 | 0.60[b] | 100 |
| 181 | N-(3-fluoro-4-methoxyphenyl)-4-(2-propylimidazo[1,2-a]pyrimidin-3-yl)-1,3-thiazol-2-amine hydrobromide | 384 | 0.67[b] | 100 |
| 182 | N-(1,3-benzodioxol-5-yl)-4-(2-propylimidazo[1,2-a]pyrimidin-3-yl)-1,3-thiazol-2-amine hydrobromide | 380 | 0.62[b] | 100 |
| 183 | N,N-dimethyl-N'-[4-(2-propylimidazo[1,2-a]pyrimidin-3-yl)-1,3-thiazol-2-yl]benzene-1,4-diamine hydrobromide | 379 | 0.49[b] | 100 |
| 184 | N-(4-bromophenyl)-4-(2-propylimidazo[1,2-a]pyrimidin-3-yl)-1,3-thiazol-2-amine hydrobromide | 416 | 0.75[b] | 100 |
| 185 | N-(4-iodophenyl)-4-(2-propylimidazo[1,2-a]pyrimidin-3-yl)-1,3-thiazol-2-amine hydrobromide | 462 | 0.77[b] | 100 |
| 186 | N-(4-methoxyphenyl)-4-(2-propylimidazo[1,2-a]pyrimidin-3-yl)-1,3-thiazol-2-amine hydrobromide | 366 | 0.63[b] | 100 |
| 187 | N-phenyl-4-(2-propylimidazo[1,2-a]pyrimidin-3-yl)-1,3-thiazol-2-amine hydrobromide | 336 | 0.64[b] | 100 |

-continued

| Cpd | Name | MS | RT | UPLC |
|---|---|---|---|---|
| 188 | N-(3-methoxyphenyl)-4-(2-methylimidazo[1,2-a]pyridin-3-yl)-1,3-thiazol-2-amine hydrobromide | 337 | 0.62[b] | 100 |
| 191 | 4-(2-methylimidazo[1,2-a]pyridin-3-yl)-N-(4-methylphenyl)-1,3-thiazol-2-amine hydrobromide | 321 | 0.64[b] | 100 |
| 192 | N-(4-ethylphenyl)-4-(2-methylimidazo[1,2-a]pyridin-3-yl)-1,3-thiazol-2-amine hydrobromide | 335 | 0.70[b] | 98 |
| 193 | N,N-diethyl-N'-[4-(2-methylimidazo[1,2-a]pyridin-3-yl)-1,3-thiazol-2-yl]benzene-1,4-diamine hydrobromide | 378 | 0.43[b] | 96 |
| 194 | N-(4-{[4-(2-methylimidazo[1,2-a]pyridin-3-yl)-1,3-thiazol-2-yl]amino}phenyl)acetamide hydrobromide | 364 | 0.47[b] | 100 |
| 195 | N-(1,3-benzodioxol-5-yl)-4-[2-(trifluoromethyl)imidazo[1,2-a]pyridin-3-yl]-1,3-thiazol-2-amine hydrobromide | 405 | 0.88[b] | 100 |
| 197 | N-(4-bromophenyl)-4-(2-methylimidazo[1,2-a]pyridin-3-yl)-1,3-thiazol-2-amine hydrobromide | 386 | 0.68[b] | 96 |
| 198 | N-(3,4-dichlorophenyl)-4-(2-methylimidazo[1,2-a]pyridin-3-yl)-1,3-thiazol-2-amine hydrobromide | 376 | 0.69[b] | 96 |
| 199 | N-(4-chlorophenyl)-4-(2-methylimidazo[1,2-a]pyridin-3-yl)-1,3-thiazol-2-amine hydrobromide | 342 | 0.67[b] | 97 |
| 200 | N-(4-bromo-2-chlorophenyl)-4-(2-methylimidazo[1,2-a]pyridin-3-yl)-1,3-thiazol-2-amine hydrobromide | 421 | 0.70[b] | 100 |
| 201 | 4-{[4-(2-methylimidazo[1,2-a]pyridin-3-yl)-1,3-thiazol-2-yl]amino}benzene-1,2-diol hydrobromide | 339 | 0.50[b] | 95 |
| 202 | N-(3,4-dimethoxyphenyl)-4-(2-methylimidazo[1,2-a]pyridin-3-yl)-1,3-thiazol-2-amine hydrobromide | 367 | 0.59[b] | 100 |
| 203 | N-(2,4-difluorophenyl)-4-(2-methylimidazo[1,2-a]pyridin-3-yl)-1,3-thiazol-2-amine hydrobromide | 343 | 0.62[b] | 100 |
| 204 | N-(4-ethoxyphenyl)-4-(2-methylimidazo[1,2-a]pyridin-3-yl)-1,3-thiazol-2-amine | 351 | 0.65[b] | 100 |
| 205 | N-(2-bromo-4-methylphenyl)-4-(6-chloro-2-methylimidazo[1,2-a]pyridin-3-yl)-1,3-thiazol-2-amine hydrobromide | 435 | 0.75[b] | 100 |
| 206 | N'-[4-(6-chloro-2-methylimidazo[1,2-a]pyridin-3-yl)-1,3-thiazol-2-yl]-N,N-diethylbenzene-1,4-diamine hydrobromide | 413 | 0.56[b] | 100 |
| 207 | 4-(6-chloro-2-methylimidazo[1,2-a]pyridin-3-yl)-N-(3,4-dimethoxyphenyl)-1,3-thiazol-2-amine hydrobromide | 402 | 0.69[b] | 100 |
| 208 | N-(2-bromo-4-methoxyphenyl)-4-(6-chloro-2-methylimidazo[1,2-a]pyridin-3-yl)-1,3-thiazol-2-amine hydrobromide | 451 | 0.78[b] | 97 |
| 209 | 4-(6-chloro-2-methylimidazo[1,2-a]pyridin-3-yl)-N-(3-methylphenyl)-1,3-thiazol-2-amine hydrobromide | 356 | 0.78[b] | 100 |
| 210 | 3-{[4-(6-chloro-2-methylimidazo[1,2-a]pyridin-3-yl)-1,3-thiazol-2-yl]amino}phenol hydrobromide | 358 | 0.64[b] | 100 |
| 211 | 1-(3-{[4-(6-chloro-2-methylimidazo[1,2-a]pyridin-3-yl)-1,3-thiazol-2-yl]amino}phenyl)ethanone hydrobromide | 384 | 0.69[b] | 100 |
| 212 | N-(3-bromophenyl)-4-(6-chloro-2-methylimidazo[1,2-a]pyridin-3-yl)-1,3-thiazol-2-amine hydrobromide | 421 | 0.79[b] | 100 |
| 213 | 4-(6-chloro-2-methylimidazo[1,2-a]pyridin-3-yl)-N-(3-chlorophenyl)-1,3-thiazol-2-amine hydrobromide | 376 | 0.79[b] | 100 |
| 214 | 4-(6-chloro-2-methylimidazo[1,2-a]pyridin-3-yl)-N-(2,4-dimethylphenyl)-1,3-thiazol-2-amine hydrobromide | 369 | 0.80[b] | 100 |
| 215 | 4-(6-chloro-2-methylimidazo[1,2-a]pyridin-3-yl)-N-(3-fluorophenyl)-1,3-thiazol-2-amine hydrobromide | 359 | 0.76[b] | 100 |
| 216 | N-(4-bromo-2-methylphenyl)-4-(6-chloro-2-methylimidazo[1,2-a]pyridin-3-yl)-1,3-thiazol-2-amine hydrobromide | 435 | 0.85[b] | 100 |
| 217 | 4-(6-chloro-2-methylimidazo[1,2-a]pyridin-3-yl)-N-(3-methoxyphenyl)-1,3-thiazol-2-amine hydrobromide | 372 | 0.75[b] | 100 |
| 218 | 4-(6-chloro-2-methylimidazo[1,2-a]pyridin-3-yl)-N-(2,4-dichlorophenyl)-1,3-thiazol-2-amine hydrobromide | 411 | 0.87[b] | 100 |
| 219 | 4-(6-chloro-2-methylimidazo[1,2-a]pyridin-3-yl)-N-(2,2-dimethyl-1,3-benzodioxol-5-yl)-1,3-thiazol-2-amine hydrobromide | 413 | 1.12[a] | 98 |
| 220 | N-(1,3-benzodioxol-5-yl)-4-(6,8-dichloro-2-methylimidazo[1,2-a]pyridin-3-yl)-1,3-thiazol-2-amine hydrobromide | 419, 420 | 0.74[b] | 100 |
| 221 | N'-[4-(2,8-dimethylimidazo[1,2-a]pyridine-3-yl)-1,3-thiazol-2-yl]-N,N-dimethylbenzene-1,4-diamine hydrobromide | 364 | 0.57[b] | 100 |
| 222 | 4-(2,8-dimethylimidazo[1,2-a]pyridin-3-yl)-N-(4-methoxyphenyl)-1,3-thiazol-2-amine hydrobromide | 351 | 0.71[b] | 100 |
| 223 | 4-(2,8-dimethylimidazo[1,2-a]pyridin-3-yl)-N-(4-methylphenyl)-1,3-thiazol-2-amine hydrobromide | 335 | 0.76[b] | 98 |
| 224 | N-(4-chlorophenyl)-4-(2,8-dimethylimidazo[1,2-a]pyridin-3-yl)-1,3-thiazol-2-amine hydrobromide | 355 | 0.56[b] | 93 |
| 225 | 4-(2,8-dimethylimidazo[1,2-a]pyridin-3-yl)-N-(3-methoxyphenyl)-1,3-thiazol-2-amine hydrobromide | 351 | 0.71[b] | 100 |
| 226 | N-(1,3-benzodioxol-5-yl)-4-(2,8-dimethylimidazo[1,2-a]pyridin-3-yl)-1,3-thiazol-2-amine hydrobromide | 365 | 0.69[b] | 98 |
| 227 | N'-[4-(8-bromo-2-methylimidazo[1,2-a]pyridin-3-yl)-1,3-thiazol-2-yl]-N,N-dimethylbenzene-1,4-diamine hydrobromide | 428, 430 | 0.61[b] | 97 |

-continued

| Cpd | Name | MS | RT | UPLC |
|---|---|---|---|---|
| 228 | 4-(8-bromo-2-methylimidazo[1,2-a]pyridin-3-yl)-N-(4-methoxyphenyl)-1,3-thiazol-2-amine hydrobromide | 415, 417 | 0.77[b] | 100 |
| 229 | 4-(8-bromo-2-methylimidazo[1,2-a]pyridin-3-yl)-N-(4-methylphenyl)-1,3-thiazol-2-amine hydrobromide | 399, 400 | 0.84[b] | 100 |
| 230 | 4-(8-bromo-2-methylimidazo[1,2-a]pyridin-3-yl)-N-(4-chlorophenyl)-1,3-thiazol-2-amine hydrobromide | 419, 421 | 0.87[b] | 97 |
| 231 | 4-(8-bromo-2-methylimidazo[1,2-a]pyridin-3-yl)-N-phenyl-1,3-thiazol-2-amine hydrobromide | 385, 387 | 0.79[b] | 100 |
| 232 | 4-(8-bromo-2-methylimidazo[1,2-a]pyridin-3-yl)-N-(3-methoxyphenyl)-1,3-thiazol-2-amine hydrobromide | 415, 417 | 0.80[b] | 96 |
| 233 | 4-(8-bromo-2-methylimidazo[1,2-a]pyridin-3-yl)-N-(2-chlorophenyl)-1,3-thiazol-2-amine hydrobromide | 421 | 0.86[b] | 100 |
| 234 | 4-(8-bromo-2-methylimidazo[1,2-a]pyridin-3-yl)-N-(2-methoxyphenyl)-1,3-thiazol-2-amine hydrobromide | 415, 417 | 0.82[b] | 100 |
| 235 | N-(1,3-benzodioxol-5-yl)-4-(8-bromo-2-methylimidazo[1,2-a]pyridin-3-yl)-1,3-thiazol-2-amine hydrobromide | 429, 430 | 0.77[b] | 97 |
| 236 | 4-(6-fluoro-2-methylimidazo[1,2-a]pyridin-3-yl)-N-(3-methoxyphenyl)-1,3-thiazol-2-amine hydrobromide | 355 | 0.63[b] | 96 |
| 237 | 4-(6-fluoro-2-methylimidazo[1,2-a]pyridin-3-yl)-N-(4-methylphenyl)-1,3-thiazol-2-amine hydrobromide | 339 | 0.67[b] | 100 |
| 238 | 1-(3-{[4-(6-fluoro-2-methylimidazo[1,2-a]pyridin-3-yl)-1,3-thiazol-2-yl]amino}phenyl)ethanone hydrobromide | 331 | 0.93[b] | 86 |
| 239 | N-(2,6-dibromophenyl)-4-(6-fluoro-2-methylimidazo[1,2-a]pyridin-3-yl)-1,3-thiazol-2-amine hydrobromide | 482 | 0.66[b] | 100 |
| 240 | 4-(7-chloro-2-methylimidazo[1,2-a]pyridin-3-yl)-N-(4-chlorophenyl)-1,3-thiazol-2-amine hydrobromide | 375, 379 | 0.79[b] | 100 |
| 241 | 4-(7-chloro-2-methylimidazo[1,2-a]pyridin-3-yl)-N-(4-methoxyphenyl)-1,3-thiazol-2-amine hydrobromide | 371 | 0.72[b] | 98 |
| 242 | N'-[4-(7-chloro-2-methylimidazo[1,2-a]pyridin-3-yl)-1,3-thiazol-2-yl]-N,N-dimethylbenzene-1,4-diamine hydrobromide | 384 | 0.59[b] | 100 |
| 243 | 4-(7-chloro-2-methylimidazo[1,2-a]pyridin-3-yl)-N-(4-methylphenyl)-1,3-thiazol-2-amine hydrobromide | 355 | 0.77[b] | 100 |
| 244 | 1-(4-{[4-(7-chloro-2-methylimidazo[1,2-a]pyridin-3-yl)-1,3-thiazol-2-yl]amino}phenyl)ethanone hydrobromide | 383 | 0.69[b] | 100 |

Example 2

N-(4-methoxyphenyl)-4-(2-methylimidazo[1,2-a]pyrimidin-3-yl)pyrimidin-2-amine (Cpd 42)

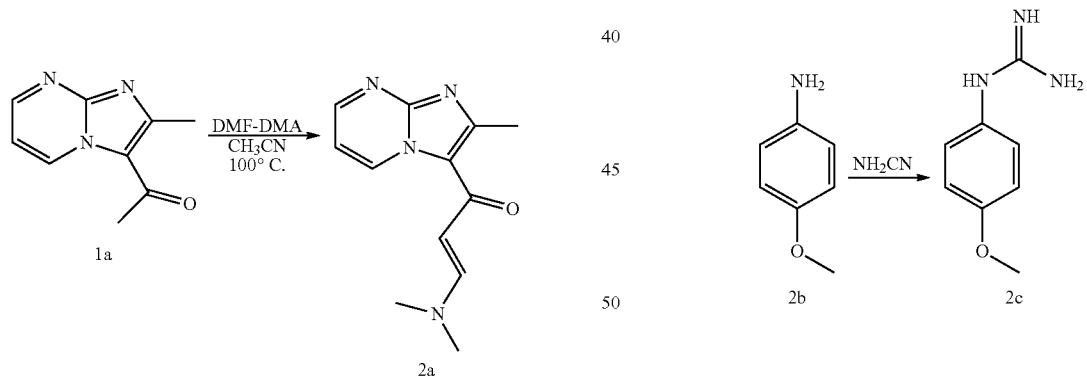

Step A. Preparation of (E)-3-(dimethylamino)-1-(2-methylimidazo[1,2-a]pyrimidin-3-yl)prop-2-en-1-one To ketone Compound 1a (0.695 g; 3.97 mmol) in 5 mL of dry CH$_3$CN was added 1.05 mL (7.94 mmol) of DMF-DMA. The mixture was heated at 100° C. in a sealed tube for 24 h, after which UPLC showed complete consumption of the starting material. The reaction mixture was diluted with Et$_2$O, and the pale yellow precipitate was collected giving a purified title Compound 2a (0.65 g, 71%). If the reaction does not go to completion (product is not purified), the product may be purified either by recrystallization from EtOH or by column chromatography.

Step B. Preparation of 1-(4-methoxyphenyl)guanidine

To a well-stirred suspension of amine Compound 2b (1.23 g, 1.0 mmol) and cyanamide (0.424 g, 1.01 mmol) in CH$_3$CN (1 mL) was added 4.0 M HCl in dioxane (1.0 Eq.). The reaction mixture was sealed under N$_2$ and heated at 100° C. until UPLC showed the disappearance of the starting material (usually 24-72 h). The reaction was quenched with aq. NaHCO$_3$, then the water fraction was extracted multiple times (up to 10) with CH$_2$Cl$_2$. The combined organic extracts were washed with brine, then dried over Na$_2$SO$_4$ and concentrated to give the title Compound 2c (1.3 g, 79%).

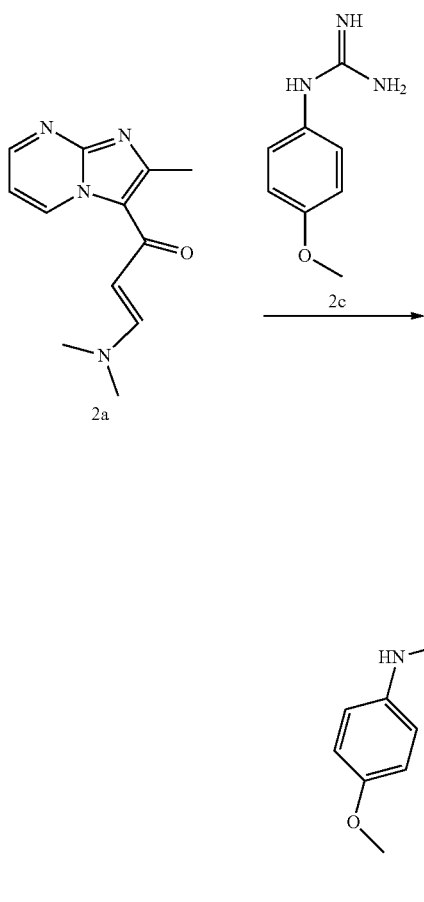

Step C. Preparation of N-(4-methoxyphenyl)-4-(2-methylimidazo[1,2-a]pyrimidin-3-yl)pyrimidin-2-amine Compound 2a (100 mg, 0.437 mmol) and Compound 2c (72 mg, 0.437 mmol) in 1 mL of dry $CH_3CN$ were heated at 100° C. in a sealed tube for 96 h, after which UPLC showed complete consumption of the starting material. The reaction mixture was concentrated and a white precipitate was collected to give the title Compound 42 (75 mg, 52%, 100% pure by UPLC); $^1$H NMR (500 MHz, DMSO-$d_6$) δ 2.70 (s, 3H), 3.76 (s, 3H), 6.93 (d, 2H, J=9.0 Hz), 7.07 (d, 1H, J=5.4 Hz), 7.15 (dd, 1H, J=6.5, 4.3 Hz), 7.59 (d, 2H, J=8.8 Hz), 8.50 (d, 1H, J=5.3 Hz), 8.64 (dd, 1H, J=4.0, 1.9 Hz), 9.48 (s, 1H), 10.2 (brs, 1H), mass spectrum (ESI): m/e (% relative intensity) 333 (100, retention time 0.91, ACQUITY 2 min).

Additional compounds may be prepared according to the procedure of Example 2 by substituting the appropriate starting materials, reagents and reaction conditions and include compounds selected from (wherein the LTPLC purity is shown as % value of sample and the retention time (RT) correlates to: [a]UPLC method: ACQUITY 2 min, or [b]UPLC method: ACQLTITY 1 min):

| Cpd | Name | MS | RT | UPLC |
|---|---|---|---|---|
| 28 | 4-(imidazo[1,2-a]pyridin-3-yl)-N-(3-methoxyphenyl)pyrimidin-2-amine | 318 | 0.92[a] | 100 |
| 43 | N,N-dimethyl-N'-[4-(2-methylimidazo[1,2-a]pyrimidin-3-yl)pyrimidin-2-yl]benzene-1,4-diamine | 346 | 0.74[a] | 100 |
| 47 | N-(4-methoxyphenyl)-N-methyl-4-(2-methylimidazo[1,2-a]pyrimidin-3-yl)pyrimidin-2-amine | 347 | 1.00[a] | 93 |
| 113 | N-(4-chlorophenyl)-4-(2-methylimidazo[1,2-a]pyridin-3-yl)pyrimidin-2-amine | 336 | 1.05[a] | 100 |
| 114 | N-(4-bromophenyl)-4-(2-methylimidazo[1,2-a]pyridin-3-yl)pyrimidin-2-amine | 381 | 1.01[a] | 98 |
| 115 | N-(4-methoxyphenyl)-4-(2-methylimidazo[1,2-a]pyridin-3-yl)pyrimidin-2-amine | 332 | 0.96[a] | 99 |
| 116 | N-(4-ethoxyphenyl)-4-(2-methylimidazo[1,2-a]pyridin-3-yl)pyrimidin-2-amine | 347 | 0.97[a] | 95 |
| 117 | 1-(4-{[4-(2-methylimidazo[1,2-a]pyridin-3-yl)pyrimidin-2-yl]amino}phenyl)ethanone | 344 | 0.93[a] | 100 |
| 118 | N,N-dimethyl-N'-[4-(2-methylimidazo[1,2-a]pyridin-3-yl)pyrimidin-2-yl]benzene-1,3-diamine | 345 | 0.79[a] | 98 |
| 119 | N-(4-iodophenyl)-4-(2-methylimidazo[1,2-a]pyridin-3-yl)pyrimidin-2-amine | 428 | 1.20[a] | 100 |
| 120 | N-(4-iodophenyl)-4-(2-methylimidazo[1,2-a]pyridin-3-yl)pyrimidin-2-amine | 429 | 1.18[a] | 98 |
| 123 | N-(1,3-benzodioxol-5-yl)-4-(2-methylimidazo[1,2-a]pyridin-3-yl)pyrimidin-2-amine | 346 | 1.01[a] | 100 |
| 124 | N-(1,3-benzodioxol-5-yl)-4-(2-methylimidazo[1,2-a]pyrimidin-3-yl)pyrimidin-2-amine | 347 | 0.99[a] | 98 |
| 125 | N-(4-iodophenyl)-N-methyl-4-(2-methylimidazo[1,2-a]pyrimidin-3-yl)pyrimidin-2-amine | 443 | 1.23[a] | 95 |
| 126 | N-(4-bromophenyl)-4-(2-methylimidazo[1,2-a]pyridin-3-yl)pyrimidin-2-amine | 381, 383 | 1.15[a] | 100 |
| 127 | N-(3-bromophenyl)-4-(2-methylimidazo[1,2-a]pyridin-3-yl)pyrimidin-2-amine | 380, 382 | 1.14[a] | 99 |

-continued

| Cpd | Name | MS | RT | UPLC |
|---|---|---|---|---|
| 128 | N-(4-ethoxyphenyl)-4-(2-methylimidazo[1,2-a]pyridin-3-yl)pyrimidin-2-amine | 380, 382 | 1.10[a] | 97 |
| 129 | N,N-dimethyl-N'-[4-(2-methylimidazo[1,2-a]pyridin-3-yl)pyrimidin-2-yl]benzene-1,4-diamine | 345 | 0.78[a] | 93 |
| 130 | N,N-diethyl-N'-[4-(2-methylimidazo[1,2-a]pyridin-3-yl)pyrimidin-2-yl]benzene-1,4-diamine | 373 | 0.80[a] | 95 |
| 131 | 1-(4-{[4-(2-methylimidazo[1,2-a]pyridin-3-yl)pyrimidin-2-yl]amino}phenyl)ethanone | 345 | 1.04[a] | 98 |
| 137 | N,N,N'-trimethyl-N'-[4-(2-methylimidazo[1,2-a]pyridin-3-yl)pyrimidin-2-yl]benzene-1,4-diamine | 359 | 0.92[a] | 91 |
| 138 | N,N-diethyl-N'-methyl-N'-[4-(2-methylimidazo[1,2-a]pyridin-3-yl)pyrimidin-2-yl]benzene-1,4-diamine | 387 | 1.00[a] | 94 |
| 139 | N-(1,3-benzodioxol-5-yl)-N-methyl-4-(2-methylimidazo[1,2-a]pyridin-3-yl)pyrimidin-2-amine | 360 | 1.08[a] | 97 |
| 140 | N-(2-chlorophenyl)-N-methyl-4-(2-methylimidazo[1,2-a]pyridin-3-yl)pyrimidin-2-amine | 351 | 1.11[a] | 90 |
| 141 | N-(4-methoxy-2,6-dimethylphenyl)-4-(2-methylimidazo[1,2-a]pyridin-3-yl)pyrimidin-2-amine | 360 | 1.09[a] | 100 |
| 142 | N-(4-ethoxyphenyl)-N-methyl-4-(2-methylimidazo[1,2-a]pyridin-3-yl)pyrimidin-2-amine | 360 | 1.02[a] | 100 |
| 143 | N-(4-iodophenyl)-N-methyl-4-(2-methylimidazo[1,2-a]pyridin-3-yl)pyrimidin-2-amine | 442 | 1.17[a] | 95 |
| 166 | N-(2-fluorophenyl)-4-(imidazo[1,2-a]pyridin-3-yl)pyrimidin-2-amine | 306 | 1.02[a] | 100 |
| 167 | 1-(4-{methyl[4-(2-methylimidazo[1,2-a]pyridin-3-yl)pyrimidin-2-yl]amino}phenyl)ethanone | 358 | 1.11[a] | 98 |
| 168 | 4-(2-methylimidazo[1,2-a]pyridin-3-yl)-N-(4-methylphenyl)pyrimidin-2-amine | 317 | 1.13[a] | 98 |
| 169 | 4-(2-methylimidazo[1,2-a]pyridin-3-yl)-N-(4-methylphenyl)pyrimidin-2-amine | 316 | 1.09[a] | 100 |
| 170 | N-methyl-4-(2-methylimidazo[1,2-a]pyridin-3-yl)-N-(4-methylphenyl)pyrimidin-2-amine | 331 | 1.18[a] | 93 |
| 189 | N-methyl-4-(2-methylimidazo[1,2-a]pyridin-3-yl)-N-(4-methylphenyl)pyrimidin-2-amine | 330 | 1.10[a] | 94 |
| 190 | 3-{[4-(2-methylimidazo[1,2-a]pyridin-3-yl)pyrimidin-2-yl]amino}phenol | 318 | 0.88[a] | 92 |
| 196 | 4-{[4-(2-methylimidazo[1,2-a]pyridin-3-yl)pyrimidin-2-yl]amino}benzoic acid | 346 | 1.32[a] | 94 |
| 245 | 4-(imidazo[1,2-a]pyridin-3-yl)-N-(4-methoxyphenyl)pyrimidin-2-amine | 318 | 0.59[b] | 100 |
| 246 | N-(3-chlorophenyl)-4-(imidazo[1,2-a]pyridin-3-yl)pyrimidin-2-amine | 322 | 0.69[b] | 100 |
| 247 | N-(2-chlorophenyl)-4-(imidazo[1,2-a]pyridin-3-yl)pyrimidin-2-amine | 322 | 0.65[b] | 93 |
| 248 | N-(4-fluorophenyl)-4-(imidazo[1,2-a]pyridin-3-yl)pyrimidin-2-amine | 306 | 0.89[b] | 100 |
| 249 | N-(2,6-dibromo-4-methoxyphenyl)-4-(imidazo[1,2-a]pyridin-3-yl)pyrimidin-2-amine | 476, 478 | 0.91[b] | 100 |
| 250 | 1-(4-{[4-(imidazo[1,2-a]pyridin-3-yl)pyrimidin-2-yl]amino}phenyl)ethanone | 330 | 0.87[b] | 100 |
| 251 | N-(1,3-benzodioxol-5-yl)-4-(imidazo[1,2-a]pyridin-3-yl)pyrimidin-2-amine | 332 | 0.87[b] | 99 |
| 252 | N-(4-ethoxyphenyl)-4-(imidazo[1,2-a]pyridin-3-yl)pyrimidin-2-amine | 332 | 0.64[b] | 100 |
| 253 | N,N-diethyl-N'-[4-(imidazo[1,2-a]pyridin-3-yl)pyrimidin-2-yl]benzene-1,4-diamine | 359 | 0.89[b] | 100 |
| 254 | N'-[4-(imidazo[1,2-a]pyridin-3-yl)pyrimidin-2-yl]-N,N-dimethylbenzene-1,4-diamine | 331 | 0.87[b] | 99 |
| 255 | N-(3-fluorophenyl)-4-(imidazo[1,2-a]pyridin-3-yl)pyrimidin-2-amine | 306 | 0.91[b] | 100 |
| 256 | N-(3-bromophenyl)-4-(imidazo[1,2-a]pyridin-3-yl)pyrimidin-2-amine | 368 | 0.94[b] | 97 |
| 257 | N-(2,6-dibromo-4-methoxyphenyl)-4-(imidazo[1,2-a]pyrimidin-3-yl)pyrimidin-2-amine | 477 | 0.97[b] | 100 |
| 258 | 1-(4-{[4-(imidazo[1,2-a]pyrimidin-3-yl)pyrimidin-2-yl]amino}phenyl)ethanone | 367 | 0.58[b] | 100 |
| 259 | N-(1,3-benzodioxol-5-yl)-4-(imidazo[1,2-a]pyrimidin-3-yl)pyrimidin-2-amine | 333 | 0.93[b] | 100 |
| 260 | 4-(imidazo[1,2-a]pyrimidin-3-yl)-N-(3-methoxyphenyl)pyrimidin-2-amine | 319 | 0.91[b] | 98 |
| 261 | 4-(imidazo[1,2-a]pyrimidin-3-yl)-N-(4-methoxyphenyl)pyrimidin-2-amine | 319 | 0.93[b] | 99 |
| 262 | N-(4-ethoxyphenyl)-4-(imidazo[1,2-a]pyrimidin-3-yl)pyrimidin-2-amine | 333 | 0.94[b] | 100 |
| 263 | N,N-diethyl-N'-[4-(imidazo[1,2-a]pyrimidin-3-yl)pyrimidin-2-yl]benzene-1,4-diamine | 360 | 0.87[b] | 100 |
| 264 | N'-[4-(imidazo[1,2-a]pyrimidin-3-yl)pyrimidin-2-yl]-N,N-dimethylbenzene-1,3-diamine | 332 | 0.90[b] | 100 |

-continued

| Cpd | Name | MS | RT | UPLC |
|---|---|---|---|---|
| 265 | N'-[4-(imidazo[1,2-a]pyrimidin-3-yl)pyrimidin-2-yl]-N,N-dimethylbenzene-1,4-diamine | 332 | 0.90$^b$ | 97 |
| 266 | N-(2-fluorophenyl)-4-(imidazo[1,2-a]pyrimidin-3-yl)pyrimidin-2-amine | 307 | 0.94$^b$ | 99 |
| 267 | N-(3-fluorophenyl)-4-(imidazo[1,2-a]pyrimidin-3-yl)pyrimidin-2-amine | 307 | 0.83$^b$ | 100 |
| 268 | N-(4-fluorophenyl)-4-(imidazo[1,2-a]pyrimidin-3-yl)pyrimidin-2-amine | 307 | 0.92$^b$ | 100 |
| 269 | N-(3-chlorophenyl)-4-(imidazo[1,2-a]pyrimidin-3-yl)pyrimidin-2-amine | 323 | 0.88$^b$ | 95 |
| 270 | N-(4-bromophenyl)-4-(imidazo[1,2-a]pyrimidin-3-yl)pyrimidin-2-amine | 369 | 0.89$^b$ | 96 |
| 271 | N-(4-bromophenyl)-4-(2-ethylimidazo[1,2-a]pyrimidin-3-yl)pyrimidin-2-amine | 395, 397 | 1.20$^a$ | 94 |

Biological Examples

The following biological examples demonstrate the usefulness of the compounds described herein for cancer by down-regulating Bmi-1 protein expression.

Example 1

Sandwich ELISA Assay

Cell Seeding and Compound Treatment (Day 1):

HT-1080 cells were seeded at 8000 cells/well (50 uL) in 96-well tissue culture plates. After the cells become adherent (3-4 hours), 2× diluted stocks of compounds in 50 uL DMEM containing 1% DMSO (final DMSO concentration was 0.5%) were added and the plates were incubated at 37° C. under 5% $CO_2$ for 40-48 hours ELISA Plate First Antibody Preparation (Day 2):

The First Antibody (Millipore Mouse, monoclonal to mouse Bmi-1, clone F6, catalog #05-637) diluted to 2 ug/mL in PBS was added (100 uL) to each well of a Nunc MaxiSorp 96-well ELISA plate. The plate was covered with a plate seal and allowed to stand overnight.

Cell Lysate Preparation (Day 3):

Fresh 1× Lysis buffer was prepared on the day of the assay as follows: 1 mM EDTA, 150 mM NaCl, 0.5% Triton-X 100, 10 mM NaF, 20 mM B-Glycerophosphate, 1 mM DTT (in PBS, pH 7.2-7.4) and 1×HALT protease inhibitor cocktail (Pierce #78410).

1× Lysis Buffer (40 uL) was added to each well and the plate was shaken for 5-10 minutes on an orbital shaker to allow cell lysis, then Diluent (1% BSA in PBS in 0.5% NP40) (100 uL) was added to each well.

The Bmi-1 standard curve was prepared in Diluent at the following concentrations of protein: 8000, 4000, 2000, 1000, 500, 250, 125, 0 pg/mL The Bmi-1 Recombinant Protein Standard (Novus Biologicals PCGF4 Recombinant Protein (P01), catalog #H00000648-P01) used in the standard curve was stored at −80° C., and on first thaw, diluted to 10 ug/uL in Blocking Buffer (1% BSA in PBS; BSA: Fisher Scientific Catalog #1600-100) before being aliquoted and refrozen at −80° C. Aliquots can be kept at 4° C. and reused after first thaw, but only for 1-2 weeks. The Bmi-1 Recombinant Protein Standard contains a GST-fusion tag and thus will show up on western blots around 70 Kda.

ELISA Assay (Day 3):

The prepared ELISA plate was washed 3× with Wash Buffer (0.05% Tween-20 in PBS). The final wash was removed from the plate and the plate was blotted dry on paper towels. Blocking Buffer (300 uL) (1% BSA in PBS) was added per well. The plate was covered with a plate seal and incubated at room temperature for 1 hour. The blocked plate was washed 3× with Wash Buffer, the final wash was removed and the plate was blotted dry on paper towels. The previously prepared samples and standards were added (at 100 uL/well) and the plate was covered with a plate seal and incubated at 4° C. overnight.

ELISA Assay (Day 4):

The prepared ELISA plate was removed from 4° C., incubated at room temperature for 30 minutes, then washed and blotted dry as previously described for Day 3. The Second Antibody (Cell Signaling Rabbit anti-Bmi-1, Cat#2830) diluted to 1:600 in Blocking Buffer was added (100 uL) to each well, except as needed for background control wells. The plate was covered with a plate seal and incubated for 1.5 hrs at room temperature.

The ELISA plate was washed and blotted dry as previously described. The Third Antibody (Cell Signaling HRP conjugated anti-rabbit IgG (CellSignaling, Cat#:7074) diluted to 1:300 in Blocking Buffer was added (100 uL) to each well, except as needed for background control wells. The plate was incubated for 1 hr at room temperature.

The plate was washed and blotted dry as previously described, then prepared TMB substrate (TMB substrate kit, Pierce catalog #34021) (prepared by mixing kit reagents 1:1) (100 uL) was added per well. The plate was incubated for 20-30 minutes at room temperature in the dark, then Stop Solution (2 M sulfuric acid in water) (50 uL) was added per well. The plates were read at OD450 (experimental) and OD570 (reference).

As shown in Table 1, test compounds described herein demonstrate Bmi-1 ELISA $IC_{50}$ values of greater than from about 1 μM to about 3 μM (*), an $IC_{50}$ value of greater than from about 0.5 μM to about 1 μM (), or an $IC_{50}$ value of less than about 0.5 μM (*).

TABLE 1

| Bmi-1 ELISA $IC_{50}$ (μM) | |
|---|---|
| Cpd | $IC_{50}$ |
| 1 | *** |
| 17 | *** |
| 12 | *** |
| 13 | *** |
| 14 | *** |
| 19 | ** |
| 20 | * |
| 21 | *** |
| 22 | *** |
| 23 | * |

TABLE 1-continued

Bmi-1 ELISA IC$_{50}$ (μM)

| Cpd | IC$_{50}$ |
|---|---|
| 24 | *** |
| 25 | *** |
| 26 | * |
| 27 | *** |
| 28 | *** |
| 29 | *** |
| 30 | *** |
| 31 | *** |
| 32 | *** |
| 33 | *** |
| 34 | *** |
| 35 | *** |
| 36 | *** |
| 37 | *** |
| 38 | *** |
| 39 | *** |
| 40 | *** |
| 41 | *** |
| 42 | *** |
| 43 | *** |
| 44 | *** |
| 45 | *** |
| 46 | *** |
| 47 | *** |
| 48 | *** |
| 49 | *** |
| 50 | *** |
| 51 | *** |
| 52 | *** |
| 53 | *** |
| 54 | *** |
| 55 | *** |
| 56 | *** |
| 57 | *** |
| 58 | *** |
| 59 | *** |
| 60 | *** |
| 61 | *** |
| 62 | *** |
| 63 | *** |
| 64 | *** |
| 65 | *** |
| 66 | *** |
| 67 | *** |
| 68 | *** |
| 69 | *** |
| 70 | *** |
| 71 | *** |
| 72 | *** |
| 73 | *** |
| 74 | *** |
| 75 | *** |
| 76 | *** |
| 77 | *** |
| 78 | *** |
| 79 | *** |
| 80 | *** |
| 81 | *** |
| 82 | *** |
| 83 | ** |
| 84 | *** |
| 85 | *** |
| 86 | *** |
| 87 | *** |
| 88 | *** |
| 89 | *** |
| 90 | *** |
| 91 | *** |
| 92 | *** |
| 93 | *** |
| 94 | *** |
| 95 | *** |
| 96 | *** |
| 97 | *** |
| 98 | *** |
| 99 | *** |
| 100 | *** |
| 101 | *** |
| 102 | *** |
| 103 | *** |
| 104 | *** |
| 105 | *** |
| 106 | *** |
| 107 | *** |
| 108 | *** |
| 109 | *** |
| 110 | *** |
| 111 | *** |
| 112 | *** |
| 113 | *** |
| 114 | *** |
| 115 | *** |
| 116 | *** |
| 117 | *** |
| 118 | *** |
| 119 | *** |
| 120 | *** |
| 121 | *** |
| 122 | *** |
| 123 | *** |
| 124 | *** |
| 125 | *** |
| 126 | *** |
| 127 | *** |
| 128 | *** |
| 129 | *** |
| 130 | *** |
| 131 | *** |
| 132 | *** |
| 133 | *** |
| 134 | *** |
| 135 | *** |
| 136 | ** |
| 137 | *** |
| 138 | *** |
| 139 | *** |
| 140 | *** |
| 141 | *** |
| 142 | *** |
| 143 | ** |
| 144 | *** |
| 145 | *** |
| 146 | *** |
| 147 | *** |
| 148 | *** |
| 149 | *** |
| 150 | *** |
| 151 | *** |
| 152 | *** |
| 153 | *** |
| 154 | *** |
| 155 | *** |
| 156 | *** |
| 157 | *** |
| 158 | *** |
| 159 | *** |
| 160 | *** |
| 161 | *** |
| 162 | *** |
| 163 | *** |
| 164 | *** |
| 165 | *** |
| 166 | *** |
| 167 | *** |
| 168 | *** |
| 169 | *** |
| 170 | *** |
| 171 | *** |
| 172 | *** |
| 173 | *** |
| 174 | *** |
| 175 | *** |

TABLE 1-continued

Bmi-1 ELISA IC$_{50}$ (µM)

| Cpd | IC$_{50}$ |
|---|---|
| 176 | *** |
| 177 | *** |
| 178 | *** |
| 179 | *** |
| 180 | *** |
| 181 | *** |
| 182 | *** |
| 183 | *** |
| 184 | *** |
| 185 | *** |
| 186 | *** |
| 187 | *** |
| 188 | *** |
| 189 | *** |
| 190 | *** |
| 191 | *** |
| 192 | *** |
| 193 | *** |
| 194 | *** |
| 195 | *** |
| 196 | *** |
| 197 | *** |
| 198 | *** |
| 199 | *** |
| 200 | *** |
| 201 | *** |
| 202 | *** |
| 203 | *** |
| 204 | *** |
| 205 | *** |
| 206 | *** |
| 207 | *** |
| 208 | *** |
| 209 | *** |
| 210 | *** |
| 211 | *** |
| 212 | *** |
| 213 | *** |
| 214 | *** |
| 215 | *** |
| 216 | *** |
| 217 | *** |
| 218 | *** |
| 219 | *** |
| 220 | *** |
| 221 | *** |
| 222 | *** |
| 223 | *** |
| 224 | *** |
| 225 | *** |
| 226 | *** |
| 227 | *** |
| 228 | *** |
| 229 | *** |
| 230 | *** |
| 231 | *** |
| 232 | *** |
| 233 | *** |
| 234 | *** |
| 235 | *** |
| 236 | *** |
| 237 | *** |
| 238 | *** |
| 239 | *** |
| 240 | *** |
| 241 | *** |
| 242 | *** |
| 243 | *** |
| 244 | *** |
| 245 | *** |
| 246 | *** |
| 247 | ** |
| 248 | *** |
| 249 | *** |
| 250 | *** |
| 251 | *** |
| 252 | *** |
| 253 | *** |
| 254 | *** |
| 255 | *** |
| 256 | *** |
| 257 | *** |
| 258 | *** |
| 259 | *** |
| 260 | *** |
| 261 | *** |
| 262 | *** |
| 263 | *** |
| 264 | *** |
| 265 | ** |
| 266 | *** |
| 267 | *** |
| 268 | *** |
| 269 | *** |
| 270 | *** |
| 271 | *** |

Example 2

In-Vivo Xenograft Model

A pharmacodynamic model that assesses intratumor Bmi-1 levels was used to demonstrate that the compounds described herein selectively inhibit Bmi-1 expression in vivo. HT1080 cells (human fibrosarcoma cells) were implanted subcutaneously in nude mice. After seven days, mice were administered compounds subcutaneously at 30 or 60 mg/kg/day for ten days. The tumors were then excised from mice and homogenized in Tris-HCl buffer containing a cocktail of proteinase inhibitors. Intratumor Bmi-1 levels were subsequently measured using the Bmi-1 ELISA assay of Example 1. Protein concentrations of the homogenates were measured with a Bio-Rad Protein assay kit and intratumor Bmi-1 levels were normalized to the protein concentrations. Treatment with the compound for ten days inhibited tumor growth by 35% as compared to the vehicle-treated control groups. In addition, Compound 1 significantly reduced intratumor Bmi-1 protein levels by 67% compared to the vehicle control ($p<0.002$). As a control, p27 levels were assessed to demonstrate that overall protein levels were not affected within the tumors. Since p27 expression is not regulated by Bmi-1 activity, no changes in the levels of this protein were observed within treated tumors. Meanwhile, no toxicity was observed within treated mice over the 10 day experiment.

Example 3

Cell Model Assays

Using assay conditions known to those skilled in the art, the ability of the compounds described herein to reduce Bmi-1 expression in HT1080 (fibrosarcoma), U87-MG (glioblastoma), T98G (glioblastoma), K562 (chronic myelogenous leukemia) and KG1 (acute myelogenous leukemia) cell lines was tested (at test compound concentrations calculated from the ELISA assay data shown in Example 1) compared to puromycin as a control to provide the EC$_{50}$ values shown in Table 2. The term "ND" means that data was not determined.

TABLE 2

| | | Bmi-1 EC$_{50}$ (µM) | | | |
|---|---|---|---|---|---|
| Cpd | HT1080 | U87-MG | T98G | K562 | KG1 |
| 1 | 0.390 | 0.420 | 0.220 | 0.374 | 0.321 |
| 12 | 0.039 | 0.110 | <0.004 | 0.010 | 0.216 |
| 14 | 0.003 | 0.008 | <0.004 | ND | ND |
| 24 | 0.310 | ND | ND | 0.076 | 0.120 |
| 25 | ND | ND | ND | 0.100 | >3 |
| 26 | ND | ND | ND | 0.234 | 0.317 |
| 27 | 0.410 | 1.200 | 0.091 | 0.055 | 0.128 |
| 28 | ND | ND | ND | 0.261 | 0.048 |
| 29 | ND | ND | ND | 0.005 | 0.304 |
| 30 | 0.004 | ND | ND | <0.004 | 0.048 |
| 39 | 0.005 | <0.004 | <0.004 | ND | ND |
| Control | 0.450 | 0.420 | 0.230 | 0.490 | 1.103 |

Example 4

Prostate Cancer Collagen Attachment Assay

The ability of the compounds described herein to reduce Bmi-1 expression in a small population of tumor initiating cells from a DU145 prostate cancer cell line was tested using a collagen attachment assay.

Cells were plated on Collagen I for 5 hours. Rapidly adhering cells have the phenotype of the CD44$^{high}$/α2β1$^{high}$ and have higher migration and higher invasion ability. The CD44$^{high}$/α2β1$^{high}$ cells when injected in nude mice can form tumors as compared to CD44$^{low}$/α2β1$^{low}$ cells. As shown in FIG. 1, the results of the collagen attachment assay demonstrated that these cells are resistant to certain chemotherapeutic drugs commonly used against prostate cancer. The data indicates that CD44$^{high}$/α2β1$^{high}$ cells have increased Bmi-1 levels. In this study, compounds described herein demonstrated inhibition of Bmi-1 in DU145 cells and also decreased the number of collagen attached cells, therefore suggesting that compounds described herein are useful in targeting prostate cancer stem cells for the treatment of prostate cancer.

Example 5

Mantle Cell Lymphoma Assay

DNA amplification of 10p12-p13 in MCL is associated with BMI-1 gene amplification and is accompanied by a significant increase in BMI-1 expression (5-7 fold) vs. normal HSC. In this assay, the results indicated that Bmi-1 inhibition with compounds described herein resulted in decreased survival of MCL cells.

MCL-derived Cell Lines and Reagents

MCL cell lines Jeko, Mino, and Rec-1 were provided by American Type Culture Collection: The Bioresource Center (Manassas, Va.). All MCL cell lines were cultured in RPMI-1640 (Invitrogen, Carlsbad, Calif.) supplemented with 20% Fetal Bovine Serum (Sigma Aldrich)/1% Penicillin-Streptomycin (Invitrogen; Carlsbad, Calif.) in T-75 culture flasks. Cell concentration was maintained between 2 to 3×10$^5$ cells/mL. Early passage cells (passages 2-4) were used for all experiments. Ficoll-Histopaque density sedimentation (Sigma Aldrich) was used for separation of debris and purification of cell lines prior to experiments. All cell lines were incubated at 37° C., 5% CO$_2$.

Test Compound Preparation

A test compound was dissolved in 100% DMSO and stored at −20° C. until use. Prior to experiments, test compounds were diluted in RPMI-1640 culture medium containing <0.1% DMSO.

Cytotoxicity Assays (Dose Response Curves)

MCL-cell lines were seeded in 24-well culture plates in RPMI-1640 media (20% FBS/1% Pen-Strep) at cell concentrations of 2×10$^5$ cells per milliliter (1 mL/well, in triplicates). Jeko, Mino and Rec-1 cell lines were treated with test compounds prepared in serial 3-fold drug dilutions, at concentrations ranging from 0 to 3 µm. The cytotoxic effect of test compounds on the MCL-cell lines was assessed by measuring cell concentration and cell viability using a Beckman Coulter Vi-Cell Counter. Controls and treated cells were harvested and counted at day 3.

As shown in Tables 3a-3f, test compounds were administered to MCL cell lines (Mino, Jeko, and Red.). After 72 hrs in culture, test compounds demonstrated significant reduction in cell viability (%) of the MCL cell lines.

TABLE 3A

| | Compound 1 | | | |
|---|---|---|---|---|
| | Cell Viability (%) and Concentration (×10$^6$) | | | |
| Dose | MCL-Mino | | MCL-Rec1 | |
| (µM) | Viability | Conc | Viability | Conc |
| 0 | 94.6 ± 0.6 | 1.58 ± 0.01 | 90.9 ± 0.4 | 1.69 ± 0.02 |
| 0.004 | 94.7 ± 0.2 | 1.53 ± 0.07 | 91.9 ± 0.5 | 1.66 ± 0.12 |
| 0.037 | 95.1 ± 0.2 | 1.53 ± 0.05 | 91.7 ± 0.4 | 1.74 ± 0.05 |
| 0.11 | 94.6 ± 0.2 | 1.55 ± 0.02 | 91.7 ± 0.2 | 1.73 ± 0.02 |
| 0.33 | 94.5 ± 0.3 | 1.50 ± 0.02 | 90.9 ± 0.2 | 1.66 ± 0.01 |
| 1 | 89.4 ± 0.4 | 0.74 ± 0.02 | 85.0 ± 0.6 | 0.96 ± 0.08 |
| 3 | 59.3 ± 0.5 | 0.20 ± 0.01 | 56.3 ± 0.4 | 0.32 ± 0.01 |

TABLE 3b

| | Compound 14 | | | | | |
|---|---|---|---|---|---|---|
| | Cell Viability (%) and Concentration (×10$^6$) | | | | | |
| Dose | MCL-Jeko | | MCL-Mino | | MCL-Rec1 | |
| (µM) | Viability | Conc | Viability | Conc | Viability | Conc |
| 0 | 76.7 ± 1.35 | 2.05 ± 0.07 | 92.83 ± 0.18 | 1.56 ± 0.10 | 90.87 ± 0.40 | 1.69 ± 0.02 |
| 0.004 | 74.9 ± 0.55 | 1.83 ± 0.03 | 92.27 ± 0.38 | 1.26 ± 0.01 | 88.10 ± 0.88 | 1.52 ± 0.02 |
| 0.037 | 69.4 ± 1.63 | 1.63 ± 0.05 | 64.47 ± 16.64 | 0.66 ± 0.24 | 84.50 ± 0.66 | 1.22 ± 0.02 |
| 0.11 | 6.5 ± 0.55 | 0.07 ± 0.01 | 40.63 ± 1.91 | 0.23 ± 0.01 | 34.43 ± 3.25 | 0.24 ± 0.03 |
| 0.33 | 1.9 ± 0.31 | 0.02 ± 0.00 | 18.10 ± 1.78 | 0.06 ± 0.01 | 8.93 ± 0.15 | 0.05 ± 0.00 |
| 1 | 1.6 ± 0.26 | 0.02 ± 0.00 | 13.53 ± 1.85 | 0.05 ± 0.01 | 9.83 ± 0.33 | 0.05 ± 0.00 |
| 3 | 2.5 ± 0.35 | 0.03 ± 0.00 | 14.07 ± 0.28 | 0.05 ± 0.00 | 9.50 ± 0.35 | 0.05 ± 0.00 |

TABLE 3c

Compound 24
Cell Viability (%) and Concentration (×10$^6$)

| Dose (μM) | MCL-Jeko Viability | Conc | MCL-Mino Viability | Conc | MCL-Rec1 Viability | Conc |
|---|---|---|---|---|---|---|
| 0 | 93.83 ± 0.24 | 1.95 ± 0.02 | 84.30 ± 0.36 | 0.63 ± 0.01 | 85.13 ± 0.55 | 0.35 ± 0.01 |
| 0.004 | 94.10 ± 0.15 | 1.95 ± 0.04 | 85.10 ± 0.67 | 0.63 ± 0.01 | 83.97 ± 1.18 | 0.36 ± 0.02 |
| 0.037 | 94.07 ± 0.23 | 1.94 ± 0.02 | 83.47 ± 0.48 | 0.63 ± 0.01 | 83.13 ± 0.47 | 0.34 ± 0.01 |
| 0.11 | 93.50 ± 0.13 | 1.92 ± 0.01 | 84.77 ± 0.50 | 0.62 ± 0.01 | 83.40 ± 1.19 | 0.34 ± 0.01 |
| 0.33 | 93.63 ± 0.06 | 1.80 ± 0.03 | 83.43 ± 0.73 | 0.55 ± 0.01 | 80.87 ± 0.33 | 0.31 ± 0.01 |
| 1 | 64.07 ± 16.28 | 0.76 ± 0.27 | 63.63 ± 2.63 | 0.28 ± 0.02 | 30.73 ± 4.15 | 0.06 ± 0.01 |
| 3 | 25.33 ± 1.19 | 0.14 ± 0.01 | 20.07 ± 1.06 | 0.05 ± 0.01 | 4.57 ± 0.08 | 0.01 ± 0.00 |

TABLE 3d

Compound 27
Cell Viability (%) and Concentration (×10$^6$)

| Dose (μM) | MCL-Jeko Viability | Conc | MCL-Mino Viability | Conc | MCL-Rec1 Viability | Conc |
|---|---|---|---|---|---|---|
| 0 | 93.83 ± 0.24 | 1.95 ± 0.02 | 84.30 ± 0.36 | 0.63 ± 0.01 | 91.63 ± 0.39 | 1.73 ± 0.02 |
| 0.004 | 93.77 ± 0.28 | 1.98 ± 0.03 | 84.67 ± 0.88 | 0.62 ± 0.02 | 90.30 ± 0.75 | 1.66 ± 0.06 |
| 0.037 | 94.40 ± 0.15 | 1.99 ± 0.02 | 84.90 ± 0.54 | 0.64 ± 0.01 | 90.37 ± 0.06 | 1.65 ± 0.03 |
| 0.11 | 93.77 ± 0.29 | 1.96 ± 0.05 | 84.47 ± 0.55 | 0.59 ± 0.03 | 90.43 ± 0.14 | 1.63 ± 0.04 |
| 0.33 | 93.67 ± 0.32 | 1.77 ± 0.02 | 83.00 ± 1.01 | 0.57 ± 0.01 | 90.37 ± 0.28 | 1.53 ± 0.01 |
| 1 | 88.20 ± 0.38 | 1.46 ± 0.02 | 75.13 ± 0.23 | 0.41 ± 0.00 | 84.73 ± 0.15 | 1.24 ± 0.03 |
| 3 | 46.23 ± 3.64 | 0.34 ± 0.04 | 29.73 ± 0.62 | 0.09 ± 0.00 | 16.77 ± 150 | 0.09 ± 0.01 |

TABLE 3e

Compound 49
Cell Viability (%) and Concentration (×10$^6$)

| Dose (μM) | MCL-Jeko Viability | Conc | MCL-Mino Viability | Conc | MCL-Rec1 Viability | Conc |
|---|---|---|---|---|---|---|
| 0 | 76.70 ± 1.35 | 2.05 ± 0.07 | 94.23 ± 0.43 | 2.12 ± 0.02 | 89.33 ± 0.84 | 0.85 ± 0.03 |
| 0.004 | 74.33 ± 0.53 | 1.83 ± 0.01 | 94.70 ± 0.44 | 1.87 ± 0.04 | 89.20 ± 0.33 | 0.83 ± 0.01 |
| 0.037 | 74.73 ± 1.08 | 1.94 ± 0.06 | 91.17 ± 1.00 | 1.72 ± 0.09 | 89.07 ± 0.33 | 0.87 ± 0.01 |
| 0.11 | 78.73 ± 0.33 | 2.06 ± 0.04 | 75.60 ± 1.49 | 0.97 ± 0.06 | 90.07 ± 0.10 | 0.84 ± 0.01 |
| 0.33 | 73.20 ± 0.58 | 1.82 ± 0.06 | 34.40 ± 2.46 | 0.15 ± 0.06 | 81.93 ± 0.03 | 0.58 ± 0.00 |
| 1 | 39.60 ± 2.28 | 0.66 ± 0.05 | 15.30 ± 1.13 | 0.07 ± 0.01 | 51.03 ± 1.83 | 0.21 ± 0.01 |
| 3 | 5.40 ± 0.61 | 0.06 ± 0.01 | 12.73 ± 1.47 | 0.06 ± 0.01 | 12.03 ± 0.95 | 0.04 ± 0.00 |

TABLE 3f

Compound 134
Cell Viability (%) and Concentration (×10$^6$)

| Dose (μM) | MCL-Jeko Viability | Conc | MCL-Mino Viability | Conc | MCL-Rec1 Viability | Conc |
|---|---|---|---|---|---|---|
| 0 | 93.83 ± 0.24 | 1.95 ± 0.02 | 84.3 ± 0.4 | 0.63 ± 0.01 | 89.33 ± 0.84 | 0.85 ± 0.03 |
| 0.004 | 94.10 ± 0.23 | 2.11 ± 0.04 | 84.8 ± 0.7 | 0.63 ± 0.01 | 89.43 ± 0.18 | 0.84 ± 0.02 |
| 0.037 | 94.37 ± 0.18 | 2.11 ± 0.03 | 86.2 ± 0.8 | 0.65 ± 0.01 | 88.90 ± 1.00 | 0.86 ± 0.02 |
| 0.11 | 93.77 ± 0.15 | 1.97 ± 0.11 | 84.6 ± 0.5 | 0.65 ± 0.01 | 90.20 ± 0.63 | 0.90 ± 0.01 |
| 0.33 | 93.67 ± 0.13 | 1.95 ± 0.02 | 83.8 ± 0.2 | 0.59 ± 0.01 | 88.63 ± 0.24 | 0.85 ± 0.02 |
| 1 | 93.87 ± 0.06 | 1.82 ± 0.05 | 81.4 ± 0.8 | 0.56 ± 0.02 | 88.43 ± 0.48 | 0.78 ± 0.03 |
| 3 | 92.40 ± 0.22 | 1.81 ± 0.02 | 79.0 ± 0.8 | 0.47 ± 0.02 | 86.67 ± 0.84 | 0.73 ± 0.02 |

Example 6

Multiple Myeloma Assay

DNA amplification of 10p12-p13 in MCL is associated with BMI-1 gene amplification and is accompanied by a significant increase in BMI-1 expression (5-7 fold) vs. normal HSC. In this assay, the results indicated that Bmi-1 inhibition using compounds described herein resulted in decreased survival of MCL cells.

As shown in Tables 4a and 4b, test compounds were administered to the MM cell line. After 72 hrs in culture, test compounds demonstrated significant reduction in cell viability (%) of the MM cell line.

TABLE 4a

| | \multicolumn{6}{c}{Cell Viability (%) and Concentration ($\times 10^6$)} |
| --- | --- | --- | --- | --- | --- | --- |
| Dose | Cpd 1 | | Cpd 14 | | Cpd 24 | |
| (µM) | Viability | Conc | Viability | Conc | Viability | Conc |
| 0 | 90.40 ± 0.44 | 1.16 ± 0.00 | 90.40 ± 0.44 | 1.16 ± 0.00 | 88.73 ± 0.06 | 1.43 ± 0.02 |
| 0.004 | 90.07 ± 0.34 | 1.02 ± 0.03 | 84.53 ± 0.40 | 0.84 ± 0.01 | 90.10 ± 0.40 | 1.37 ± 0.03 |
| 0.037 | 89.53 ± 0.71 | 1.06 ± 0.01 | 54.43 ± 0.98 | 0.22 ± 0.00 | 89.07 ± 0.13 | 1.38 ± 0.04 |
| 0.11 | 90.33 ± 0.10 | 1.13 ± 0.02 | 54.87 ± 2.79 | 0.21 ± 0.01 | 86.07 ± 0.21 | 1.23 ± 0.01 |
| 0.33 | 90.63 ± 0.28 | 1.10 ± 0.02 | 57.67 ± 1.33 | 0.21 ± 0.01 | 60.13 ± 2.25 | 0.59 ± 0.04 |
| 1 | 85.40 ± 0.58 | 0.54 ± 0.03 | 60.87 ± 1.26 | 0.24 ± 0.01 | 39.95 ± 13.47 | 0.34 ± 0.14 |
| 3 | 79.03 ± 0.45 | 0.39 ± 0.02 | 59.93 ± 1.32 | 0.25 ± 0.01 | 24.23 ± 0.86 | 0.17 ± 0.01 |

TABLE 4b

| | \multicolumn{6}{c}{Cell Viability (%) and Concentration ($\times 10^6$)} |
| --- | --- | --- | --- | --- | --- | --- |
| Dose | Cpd 27 | | Cpd 49 | | Cpd 134 | |
| (µM) | Viability | Conc | Viability | Conc | Viability | Conc |
| 0 | 88.73 ± 0.06 | 1.43 ± 0.02 | 90.40 ± 0.44 | 1.16 ± 0.00 | 88.73 ± 0.06 | 1.43 ± 0.02 |
| 0.004 | 89.13 ± 0.19 | 1.46 ± 0.01 | 89.63 ± 0.35 | 1.22 ± 0.05 | 91.17 ± 0.43 | 1.36 ± 0.01 |
| 0.037 | 87.53 ± 0.60 | 1.36 ± 0.07 | 89.53 ± 0.46 | 1.09 ± 0.05 | 90.27 ± 0.10 | 1.33 ± 0.01 |
| 0.11 | 86.00 ± 0.20 | 1.30 ± 0.01 | 84.70 ± 0.88 | 0.85 ± 0.05 | 87.93 ± 0.50 | 1.28 ± 0.01 |
| 0.33 | 69.27 ± 0.75 | 0.80 ± 0.01 | 69.57 ± 0.85 | 0.38 ± 0.01 | 86.10 ± 0.31 | 1.18 ± 0.04 |
| 1 | 24.1 ± 0.57 | 0.17 ± 0.00 | 55.50 ± 2.40 | 0.21 ± 0.01 | 83.47 ± 0.46 | 1.06 ± 0.01 |
| 3 | 21.7 ± 0.15 | 0.2 ± 0.05 | 55.53 ± 1.79 | 0.22 ± 0.01 | 76.50 ± 1.48 | 0.75 ± 0.03 |

Example 7

Western Blot Analysis

Whole Cell Extraction

Western Blot analysis was used to determine cytoplasmic protein levels of Bmi-1 and activation of key executioner proteins (Caspases 3, 7, 8, 9) involved in apoptosis. Protein levels were measured in Bmi-1 inhibitor-treated mantle cell lymphoma cell lines. Jeko, Mino and Rec 1 cells were each treated with Compounds 1 (data not shown), 14 and 49 (data not shown) for 24, 48 and 72 hours at concentrations based on the $IC_{50}$ values for each compound (refer to cell viability and concentration dose response results shown in Example 5). Cells were harvested at each time point, washed with ice-cold PBS, and lysed with 1× lysis buffer (20 mM Tris-HCl (pH 7.5), 150 mM NaCl, 1 mM $Na_2EDTA$, 1 mM EGTA, 1% Triton, 2.5 mM sodium pyrophosphate, 1 mM beta-glycerophosphate, 1 mM $Na_3VO_4$, 1 µg/ml leupeptin; Cell Signaling Technology; Danvers, Mass.). Protein concentrations were determined using Pierce BCA protein assay (Thermo Scientific; Rockford, Ill.). Electrophoresis of cell lysates (25 µg) were performed with Mini Protean Systems by Bio-Rad Laboratories and run in Bio-Rad Readymade Pre-Cast Gels (4-20% Tris-HCl gels). Proteins were transferred onto PVDF membrane (Bio-Rad), and immunoblotted with anti-Bmi-1-clone F6 antibody (Millipore; Temecula, Calif.) and Caspases 3, 7, 8 and 9 (Cell Signaling Technology; Danvers, Mass.).

Figure 2:
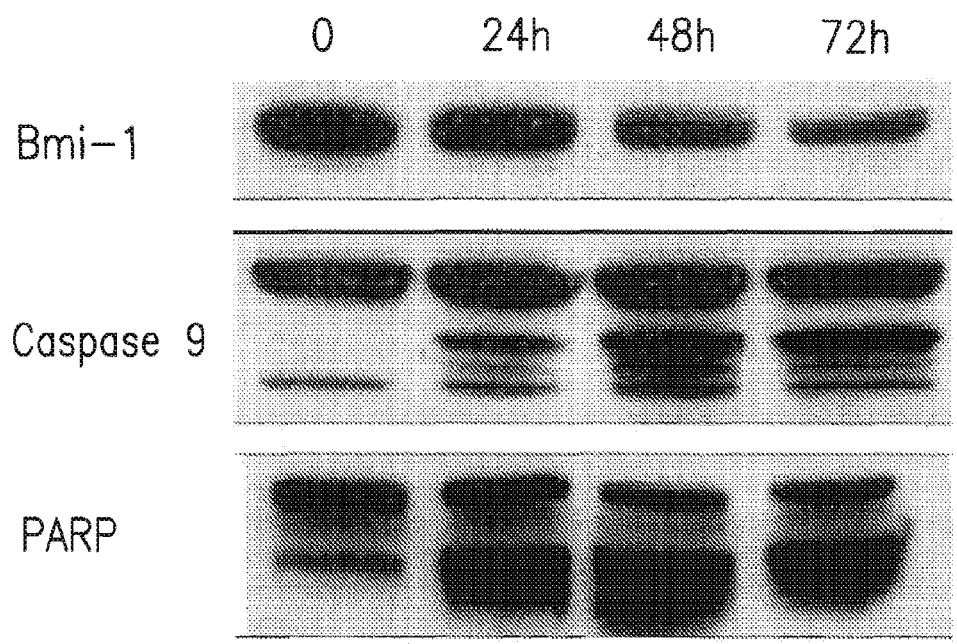
FIG. 2 shows that BMI-1 inhibitor compounds described herein affect activation of the apoptotic pathway.

As shown in FIG. 2, MCL cells cultured with Compound 14 for 72 hrs resulted in a time dependant decrease of Bmi-1 levels with a concomitant activation of Caspase-9 and PARP, indicating induction of the apoptotic pathway.

Example 8

Cell Cycle Analysis

Cell cycle analysis was performed for MCL-cell lines treated with Bmi-1 inhibitor Compounds 1 (data not shown), 14 and 49 (data not shown). For example, Jeko, Mino and Red cells treated with BMI-1 inhibitor Compound 14 at concentrations of 60 nM, 75 nM, and 60 nM, respectively were cultured in T-25 flasks for 24, 48 and 72 hours in 37° C. About $1 \times 10^6$ cells were harvested, washed with PBS, fixed with ice-cold 70% ethanol, and treated with 1 mg/ml RNase A (Invitrogen; Carlsbad, Calif.). Cells were then stained with 5 µL 1 mg/mL Propidium Iodide (Sigma-Aldrich; St. Louis, Mo.), incubated in ice for at least 1 hr, and the cell cycle profile was determined using flow cytometry analysis. The same protocol was followed for cell cycle analysis of Jeko, Mino, and Rec1 cell lines treated with Compounds 1 (data not shown) and 49 (data not shown).

Figure 3:
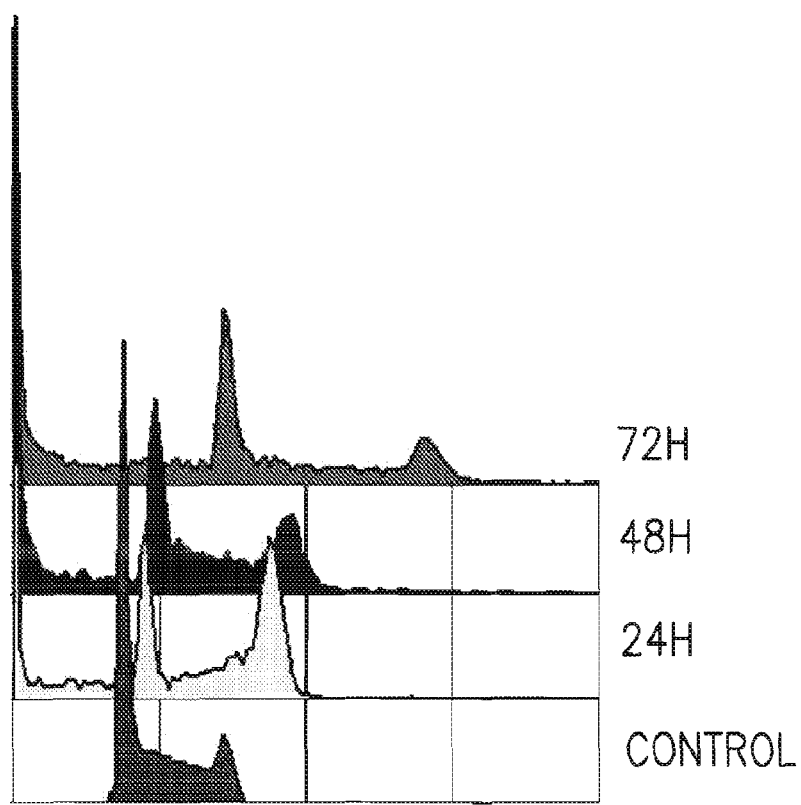
FIG. 3 shows that BMI-1 inhibitor compounds described herein effect a block of the tumor cell cycle.

As shown in FIG. 3, MCL cells were cultured with 60 nM of Compound 14 for 72 hrs, followed by flow cytometric analysis. Treated cells demonstrated a G2/M block at 24 hrs followed by an increase in DNA content at 48 and 72 hrs.

Example 9

Apoptosis Assay

Jeko, Mino and Rec-1 cells were treated with Bmi-1 inhibitor Compounds 1, 14 and 49 in an apoptosis assay used to quantify and detect apoptotic cells at 24, 48 and 72 hours of treatment. Vybrant® Apoptosis Assay Kit #2 was used for assaying apoptosis in this study (Molecular Probes, Invitrogen; Eugene, Oreg.). Jeko, Mino, and Rec-1 cell lines were treated with Compounds 1, 14 and 49 at concentrations of 80 nM, 75 nM and 80 nM, respectively. Cells were harvested ($1\times10^6$ cells) at 24, 28 and 72 hours, washed with ice-cold phosphate-buffered saline and resuspended in 1× annexin-binding buffer. Alexa-Fluor® 488 annexin V (5 µL) and 100 µg/mL PI (1 µL) were added, and incubated at room temperature for 15 min. After the addition of 1× annexin-binding buffer, Jeko, Mino and Rec1 cells treated with Compounds 1, 14 and 49 were harvested, placed in ice and analyzed by flow cytometry. Jeko, Mino and Rec-1 cells were treated with Bmi-1 inhibitor Compounds 1, 14 and 49 showed a substantial decrease in cell viability (~70-90%) after 3 days of treatment indicating significant cell death.

The following publications are incorporated by reference into the present application for any and all purposes to the same extent as if each individual publication was fully set forth herein:

1. M. J. Alkema, J. Wiegant, A. K. Raap, A. Berns, L. M. van, *Hum. Mol. Genet.* 2, 1597 (1993).
2. Y. Haupt, M. L. Bath, A. W. Harris, J. M. Adams, *Oncogene* 8, 3161-3164 (1993).
3. J. M. Adams, S. Cory, *Cancer Surv.* 15, 119 (1992).
4. Y. Haupt, G. Barri, J. M. Adams, *Mol. Biol. Rep.* 17, 17 (1992).
5. L. M. van, M. Frasch, E. Wientjens, A. Berns, *Nature* 353, 353 (1991).
6. L. M. van et al., *Cell* 65, 737 (1991).
7. J. J. Jacobs et al., *Genes Dev.* 13, 2678 (1999).
8. B. Scheijen, J. Jonkers, D. Acton, A. Berns, *J. Virol.* 71, 9 (1997).
9. J. J. Jacobs, K. Kieboom, S. Marino, R. A. DePinho, L. M. van, *Nature* 397, 164 (1999).
10. P. R. Solomon et al., *Indian J. Med. Res.* 127, 52 (2008).
11. B. Quesnel, C. Preudhomme, P. Fenaux, *Leuk. Lymphoma* 22, 11 (1996).
12. S. Faderl et al., *Cytokines Cell Mol. Ther.* 5, 159 (1999).
13. S. Faderl et al., *Clin. Cancer Res.* 5, 1855 (1999).
14. S. W. Bruggeman et al., *Cancer Cell* 12, 328 (2007).
15. S. J. Kuerbitz, J. Malandro, N. Compitello, S. B. Baylin, J. R. Graff, *Cell Growth Differ.* 10, 27 (1999).
16. S. Liu et al., *Cancer Res.* 66, 6063 (2006).
17. J. Wei, L. Zhai, J. Xu, H. Wang, *J. Biol. Chem.* 281, 22537 (2006).
18. M. Courel, L. Friesenhahn, J. A. Lees, *Dev. Dyn.* 237, 1232 (2008).
21. D. F. Dukers et al., *Am. J. Pathol.* 164, 873 (2004).
22. F. M. Raaphorst et al., *Am. J. Pathol.* 157, 709 (2000).
23. M. Sanchez-Beato et al., *J. Pathol.* 204, 528 (2004).
24. S. Bea et al., *Blood* 93, 4365 (1999).
25. M. S. Lindstrom, U. Klangby, K. G. Wiman, *Oncogene* 20, 2171 (2001).
26. F. J. van Kemenade et al., *Blood* 97, 3896 (2001).
27. F. M. Raaphorst, C. J. Meijer, A. P. Otte, *Cancer Res.* 62, 618 (2002).
28. F. M. Raaphorst et al., *Am. J. Pathol.* 164, 533 (2004).
29. V. Fernandez, E. Hartmann, G. Ott, E. Campo, A. Rosenwald, *J. Clin. Oncol.* 23, 6364 (2005).
30. B. T. Spike, K. F. Macleod, *Cell Cycle* 4, 42 (2005).
31. A. Dutton et al., *Blood* 109, 2597 (2007).
32. M. Chowdhury et al., *Leukemia* 21, 1116 (2007).
33. W. A. Dik et al., *Leukemia* 19, 1948 (2005).
34. M. Sawa et al., *Int. J. Hematol.* 82, 42-47 (2005).
35. J. Yang et al., *Proc. Natl. Acad. Sci. U. S. A* 104, 10494 (2007).
36. G. D. van et al., *Exp. Hematol.* 35, 1538 (2007).
37. J. C. van Galen et al., *J. Clin. Pathol.* 60, 167 (2007).
38. R. Kuppers, U. Klein, M. L. Hansmann, K. Rajewsky, *N. Engl. J. Med.* 341, 1520 (1999).
39. A. A. Alizadeh et al., *Nature* 403, 503 (2000).
40. C. P. Hans et al., *Blood* 103, 275 (2004).
41. W. P. de Boer, J. J. Oudejans, C. J. Meijer, J. Lankelma, *Bioinformatics.* 19, 2000 (2003).
42. S. Bea et al., *Cancer Res.* 61, 2409 (2001).
43. G. V. Glinsky, O. Berezovska, A. B. Glinskii, *J. Clin. Invest* 115, 1503-1521 (2005).
44. K. Mihara et al., *Rinsho Ketsueki* 48, 659 (2007).
45. J. B. Ames, K. Collett, L. A. Akslen, *Histopathology* 52, 370 (2008).
46.1. B. Engelsen et al., *Br. J. Cancer* 98, 1662 (2008).
47. V. Hayry et al., *Acta Neuropathol.* (2008).
48. V. Hayry et al., *Neuropathol. Appl. Neurobiol.* (2008).
49. K. H. Huang, J. H. Liu, X. X. Li, L. B. Song, M. S. Zeng, *Nan. Fang Yi. Ke. Da. Xue. Xue. Bao.* 27, 973 (2007).
50. E. M. Hurt, B. T. Kawasaki, G. J. Klarmann, S. B. Thomas, W. L. Farrar, *Br. J. Cancer* 98, 756 (2008).
51. J. H. Liu et al., *J. Surg. Oncol.* 97, 267 (2008).
52. K. Mihara et al., *Blood* 107, 305 (2006).
53. L. B. Song et al., *Cancer Res.* 66, 6225 (2006).
54. H. Vekony et al., *J. Clin. Pathol.* 61, 744 (2008).
55. H. Wang et al., *J. Cancer Res. Clin. Oncol.* 134, 535 (2008).
56. R. H. Breuer et al., *Neoplasia.* 6, 736 (2004).
57. S. Vonlanthen et al., *Br. J. Cancer* 84, 1372 (2001).
58. S. K. Li et al., *J. Biol. Chem.* (2008).
59. W. J. Guo, S. Datta, V. Band, G. P. Dimri, *Mol. Biol. Cell* 18, 536 (2007).
60. K. Nowak et al., *Nucleic Acids Res.* 34, 1745 (2006).
61. H. Cui et al., *Am. J. Pathol.* 170, 1370-1378 (2007).
62. G. P. Dimri et al., *Cancer Res.* 62, 4736 (2002).
63. M. K. Kang et al., *Br. J. Cancer* 96, 126 (2007).
64. J. H. Kim et al., *Cancer Lett.* 203, 217 (2004).
65. J. H. Kim et al., *Breast* 13, 383-388 (2004).
66. H. Koga et al., *Oncogene* 18, 3799 (1999).
67. N. Kozakowski, A. Soleiman, J. Pammer, *Pathol. Oncol. Res.* 14, 9 (2008).
68. F. Zhang, L. Sui, T. Xin, *Exp. Oncol.* 30, 70 (2008).
69. L. Liu, L. G. Andrews, T. O. Tollefsbol, *Oncogene* 25, 4370-4375 (2006).
76. Park et al., 2003, Nature. 423:302-305.
77. Lessard et al., 2003, Nature 423:255-260.
78. Wiederschain et al., 2007, Mol Cell Biol. 27(13):4968-4967.
79. Reinisch et al., 2006, Histol Histopathol. 21:1143-1149.
80. Breuer et al., 2005, Lung Cancer. 48:299-306.

Without regard to whether a document cited herein was specifically and individually indicated as being incorporated by reference, all documents referred to herein are incorporated by reference into the present application for any and all purposes to the same extent as if each individual reference was fully set forth herein.

Although certain embodiments have been described in detail above, those having ordinary skill in the art will clearly understand that many modifications are possible in the embodiments without departing from the teachings thereof. All such modifications are intended to be encompassed within the scope of the claims presented herein.

What is claimed is:

1. A compound of Formula (I):

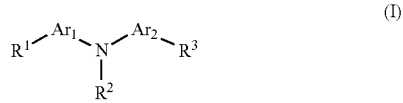

wherein,
Ar$_1$ is phenyl or benzo[1,3]dioxolyl;
Ar$_2$ is thiazolyl or pyrimidinyl substituted with R$^4$;
R$^1$ is hydrogen or one, two, three or four substituents each selected from halogen, cyano, hydroxy, C$_{1-8}$alkyl, C$_{2-8}$alkenyl, C$_{2-8}$alkynyl, C$_{1-8}$alkoxy, halo-C$_{1-8}$alkyl, halo-C$_{1-8}$alkoxy, hydroxy-C$_{1-8}$alkyl, C$_{1-8}$alkoxy-C$_{1-8}$alkyl, C$_{1-8}$alkoxy-C$_{1-8}$alkoxy, C$_{1-8}$alkoxy-C$_{1-8}$alkoxy-C$_{1-8}$alkyl, carboxy, amino, C$_{1-8}$alkyl-amino, amino-C$_{1-8}$alkyl, C$_{1-8}$alkyl-amino-C$_{1-8}$alkyl, C$_{1-8}$alkyl-carbonyl, C$_{1-8}$alkoxy-carbonyl, aminosulfonyl, C$_{1-8}$alkyl-aminosulfonyl, C$_{1-8}$alkyl-carbonyl-amino and C$_{1-8}$alkoxy-carbonyl-amino;
R$^2$ is hydrogen or C$_{1-8}$alkyl;
R$^3$ is imidazo[1,2-a]pyridin-3-yl or imidazo[1,2-a]pyrimidin-3-yl each substituted with R$^5$ and R$^6$;
R$^4$ and R$^5$ are each hydrogen, C$_{1-8}$alkyl or halo-C$_{1-8}$alkyl; and
R$^6$ is hydrogen or one, two, three or four substituents each selected from halogen, hydroxy or C$_{1-8}$alkyl;
or a free acid, free base, salt, ester, hydrate, solvate, chelate, clathrate, isotopologue, geometric isomer, stereoisomer, racemate, enantiomer, diastereomer or tautomer thereof,
with the proviso that the compound of Formula (I) is other than:
N-(2,6-dibromo-4-methoxyphenyl)-4-(2-methylimidazo[1,2-a]pyrimidin-3-yl)thiazol-2-amine,
N-(3-chloro-2-methylphenyl)-4-(2-methylimidazo[1,2-a]pyrimidin-3-yl)thiazol-2-amine,
N-(2,5-dimethoxyphenyl)-4-(2-methylimidazo[1,2-a]pyrimidin-3-yl)thiazol-2-amine,
N-(2-ethoxyphenyl)-4-(2-methylimidazo[1,2-a]pyrimidin-3-yl)thiazol-2-amine,
N-(2-chlorophenyl)-4-(2-methylimidazo[1,2-a]pyrimidin-3-yl)thiazol-2-amine,
4-(2-methylimidazo[1,2-a]pyrimidin-3-yl)-N-m-tolylthiazol-2-amine,
N,N-diethyl-N'-(4-(2-methylimidazo[1,2-a]pyrimidin-3-yl)thiazol-2-yl)benzene-1,4-diamine,
N-(2-methoxyphenyl)-4-(2-methylimidazo[1,2-a]pyrimidin-3-yl)thiazol-2-amine,
1-(3-(4-(2-methylimidazo[1,2-a]pyrimidin-3-yl)thiazol-2-ylamino)phenyl)ethanone,
4-(4-(2-methylimidazo[1,2-a]pyrimidin-3-yl)thiazol-2-ylamino)benzenesulfonamide,
N-(4-(4-(2-methylimidazo[1,2-a]pyrimidin-3-yl)thiazol-2-ylamino)phenyl)acetamide,
N,N-dimethyl-N'-(4-(2-methylimidazo[1,2-a]pyrimidin-3-yl)thiazol-2-yl)benzene-1,4-diamine,
N-(4-ethoxyphenyl)-4-(2-methylimidazo[1,2-a]pyrimidin-3-yl)thiazol-2-amine,
N-(4-methoxyphenyl)-4-(2-methylimidazo[1,2-a]pyrimidin-3-yl)thiazol-2-amine,
4-(4-(2-methylimidazo[1,2-a]pyrimidin-3-yl)thiazol-2-ylamino)benzoic acid,
4-(4-(2,7-dimethylimidazo[1,2-a]pyridin-3-yl)thiazol-2-ylamino)phenol,
4-(2,7-dimethylimidazo[1,2-a]pyridin-3-yl)-N-(4-methoxyphenyl)thiazol-2-amine, and
4-(2,7-dimethylimidazo[1,2-a]pyridin-3-yl)-N-(2-methoxyphenyl)thiazol-2-amine.

2. The compound of claim 1, wherein R$^1$ is hydrogen or one, two, three or four substituents each selected from halogen, hydroxy, C$_{1-8}$alkyl, C$_{1-8}$alkoxy, C$_{1-8}$alkoxy-C$_{1-8}$alkoxy, carboxy, C$_{1-8}$alkyl-amino, C$_{1-8}$alkyl-carbonyl, aminosulfonyl or C$_{1-8}$alkyl-carbonyl-amino.

3. The compound of claim 2, wherein R$^1$ is hydrogen or one, two or three substituents each selected from chloro, fluoro, bromo, iodo, hydroxy, methyl, ethyl, isopropyl, tert-butyl, methoxy, ethoxy, methoxy-ethoxy, carboxy, dimethylamino, diethyl-amino, methyl-carbonyl, aminosulfonyl or methyl-carbonyl-amino.

4. The compound of claim 1, wherein
R$^2$ is hydrogen or methyl;
R$^4$ and R$^5$ are each hydrogen, methyl, ethyl, n-propyl or trifluoromethyl; and
R$^6$ is hydrogen or one, two, three or four substituents each selected from fluoro, chloro, bromo, hydroxy, methyl or n-propyl.

5. A compound or a free acid, free base, salt, ester, hydrate, solvate, chelate, clathrate, isotopologue, geometric isomer, stereoisomer, racemate, enantiomer, diastereomer or tautomer thereof selected from:
N-(2,6-dichloro-4-methoxyphenyl)-4-(2-methylimidazo[1,2-a]pyrimidin-3-yl)thiazol-2-amine,
N-(2,6-difluoro-4-methoxyphenyl)-4-(2-methylimidazo[1,2-a]pyrimidin-3-yl)thiazol-2-amine,
N-(2,6-dibromo-4-methylphenyl)-4-(2-methylimidazo[1,2-a]pyrimidin-3-yl)thiazol-2-amine,
4-(2-methylimidazo[1,2-a]pyrimidin-3-yl)-N-(2,4,6-tribromophenyl)thiazol-2-amine,
N-(2,6-dibromo-4-(2-methoxyethoxy)phenyl)-4-(2-methylimidazo[1,2-a]pyrimidin-3-yl)thiazol-2-amine,
4-(6-chloroimidazo[1,2-a]pyridine-3-yl)-N-(2,6-dibromo-4-methoxyphenyl)thiazol-2-amine,
4-(6-chloroimidazo[1,2-a]pyridine-3-yl)-N-(2,6-dibromo-4-methylphenyl)thiazol-2-amine,
4-(6-chloroimidazo[1,2-a]pyridine-3-yl)-N-(2,6-dichloro-4-methoxyphenyl)thiazol-2-amine,
4-(6-chloroimidazo[1,2-a]pyridine-3-yl)-N-(4-methoxy-2,6-dimethylphenyl)thiazol-2-amine,
4-(imidazo[1,2-a]pyridine-3-yl)-N-(3-methoxyphenyl)pyrimidin-2-amine,
4-(6-chloro-2-methylimidazo[1,2-a]pyridin-3-yl)-N-(4-iodophenyl)thiazol-2-amine,
N-(benzo[d][1,3]dioxol-5-yl)-4-(6-chloro-2-methylimidazo[1,2-a]pyridin-3-yl)thiazol-2-amine,
3-{[4-(2,7-dimethylimidazo[1,2-a]pyridin-3-yl)-1,3-thiazol-2-yl]amino}phenol,
4-(2,7-dimethylimidazo[1,2-a]pyridin-3-yl)-N-(4-methylphenyl)-1,3-thiazol-2-amine,
1-(4-{[4-(2,7-dimethylimidazo[1,2-a]pyridin-3-yl)-1,3-thiazol-2-yl]amino}phenyl)ethanone,
1-(4-{[4-(2-methylimidazo[1,2-a]pyrimidin-3-yl)-1,3-thiazol-2-yl]amino}phenyl)ethanone,
3-{[4-(2-methylimidazo[1,2-a]pyridin-3-yl)-1,3-thiazol-2-yl]amino}phenol, 4-{[4-(2-methylimidazo[1,2-a]pyridin-3-yl)-1,3-thiazol-2-yl]amino}phenol,
N-(1,3-benzodioxol-5-yl)-4-(2-methylimidazo[1,2-a]pyrimidin-3-yl)-1,3-thiazol-2-amine,
N-(2,6-dichlorophenyl)-4-(2-methylimidazo[1,2-a]pyrimidin-3-yl)-1,3-thiazol-2-amine,
N-(4-iodophenyl)-4-(2-methylimidazo[1,2-a]pyrimidin-3-yl)-1,3-thiazol-2-amine,
N-(1,3-benzodioxol-5-yl)-N-methyl-4-(2-methylimidazo[1,2-a]pyrimidin-3-yl)-1,3-thiazol-2-amine,
N,N-dimethyl-N'-[4-(2-methylimidazo[1,2-a]pyridin-3-yl)-1,3-thiazol-2-yl]benzene-1,4-diamine,
N-(4-methoxyphenyl)-4-(2-methylimidazo[1,2-a]pyrimidin-3-yl)pyrimidin-2-amine,
N,N-dimethyl-N'-[4-(2-methylimidazo[1,2-a]pyrimidin-3-yl)pyrimidin-2-yl]benzene-1,4-diamine,
N-(4-methoxyphenyl)-4-(2-methylimidazo[1,2-a]pyridin-3-yl)-1,3-thiazol-2-amine,
N-(3-fluoro-4-methoxyphenyl)-4-(2-methylimidazo[1,2-a]pyrimidin-3-yl)-1,3-thiazol-2-amine,
N-(3-chloro-4-methoxyphenyl)-4-(2-methylimidazo[1,2-a]pyrimidin-3-yl)-1,3-thiazol-2-amine,
N-(4-methoxyphenyl)-N-methyl-4-(2-methylimidazo[1,2-a]pyrimidin-3-yl)pyrimidin-2-amine,
N-(4-bromophenyl)-4-(2-methylimidazo[1,2-a]pyrimidin-3-yl)-1,3-thiazol-2-amine,
N-(4-chlorophenyl)-4-(2-methylimidazo[1,2-a]pyrimidin-3-yl)-1,3-thiazol-2-amine,
N-(3-chloro-4-methoxyphenyl)-4-(2-methylimidazo[1,2-a]pyridin-3-yl)-1,3-thiazol-2-amine,
N-(3-fluoro-4-methoxyphenyl)-4-(2-methylimidazo[1,2-a]pyridin-3-yl)-1,3-thiazol-2-amine,
N-[4-(2-methoxyethoxy)phenyl]-4-(2-methylimidazo[1,2-a]pyridin-3-yl)-1,3-thiazol-2-amine,
N-(4-iodophenyl)-4-(2-methylimidazo[1,2-a]pyridin-3-yl)-1,3-thiazol-2-amine,
N-[2,6-dibromo-4-(2-methoxyethoxy)phenyl]-4-(2-methylimidazo[1,2-a]pyridin-3-yl)-1,3-thiazol-2-amine,
1-(4-{[4-(2-methylimidazo[1,2-a]pyridin-3-yl)-1,3-thiazol-2-yl]amino}phenyl)ethanone,
N-(1,3-benzodioxol-5-yl)-4-(2-methylimidazo[1,2-a]pyridin-3-yl)-1,3-thiazol-2-amine,
N-(2,6-difluoro-4-methoxyphenyl)-4-(2-methylimidazo[1,2-a]pyridin-3-yl)-1,3-thiazol-2-amine,
N'-[4-(6-chloro-2-methylimidazo[1,2-a]pyridin-3-yl)-1,3-thiazol-2-yl]-N,N-dimethylbenzene-1,4-diamine,
4-(6-chloro-2-methylimidazo[1,2-a]pyridin-3-yl)-N-(4-methoxyphenyl)-1,3-thiazol-2-amine,
4-(6-chloro-2-methylimidazo[1,2-a]pyridin-3-yl)-N-(4-chlorophenyl)-1,3-thiazol-2-amine,
N-(4-bromophenyl)-4-(6-chloro-2-methylimidazo[1,2-a]pyridin-3-yl)-1,3-thiazol-2-amine,
1-(4-{[4-(6-chloro-2-methylimidazo[1,2-a]pyridin-3-yl)-1,3-thiazol-2-yl]amino}phenyl)ethanone,
N-(1,3-benzodioxol-5-yl)-4-(2,7-dimethylimidazo[1,2-a]pyridin-3-yl)-1,3-thiazol-2-amine,
N'-[4-(2,7-dimethylimidazo[1,2-a]pyridin-3-yl)-1,3-thiazol-2-yl]-N,N-dimethylbenzene-1,4-diamine,
N-(4-chlorophenyl)-4-(2,7-dimethylimidazo[1,2-a]pyridin-3-yl)-1,3-thiazol-2-amine,
4-(2,7-dimethylimidazo[1,2-a]pyridin-3-yl)-N-(3-fluoro-4-methoxyphenyl)-1,3-thiazol-2-amine,
N-(3-chloro-4-methoxyphenyl)-4-(2,7-dimethylimidazo[1,2-a]pyridin-3-yl)-1,3-thiazol-2-amine,
N-(4-bromophenyl)-4-(2,7-dimethylimidazo[1,2-a]pyridin-3-yl)-1,3-thiazol-2-amine,
4-(2,7-dimethylimidazo[1,2-a]pyridin-3-yl)-N-(4-iodophenyl)-1,3-thiazol-2-amine,
N'-[4-(2,6-dimethylimidazo[1,2-a]pyridin-3-yl)-1,3-thiazol-2-yl]-N,N-dimethylbenzene-1,4-diamine,
4-(2,6-dimethylimidazo[1,2-a]pyridin-3-yl)-N-(4-methoxyphenyl)-1,3-thiazol-2-amine,
N-(1,3-benzodioxol-5-yl)-4-(2,6-dimethylimidazo[1,2-a]pyridin-3-yl)-1,3-thiazol-2-amine,
N-(3-chloro-4-methoxyphenyl)-4-(2,6-dimethylimidazo[1,2-a]pyridin-3-yl)-1,3-thiazol-2-amine,
4-(2,6-dimethylimidazo[1,2-a]pyridin-3-yl)-N-[4-(2-methoxyethoxy)phenyl]-1,3-thiazol-2-amine,
N'-[4-(2,6-dimethylimidazo[1,2-a]pyridin-3-yl)-1,3-thiazol-2-yl]-N,N-diethylbenzene-1,4-diamine,
4-(2,6-dimethylimidazo[1,2-a]pyridin-3-yl)-N-(4-iodophenyl)-1,3-thiazol-2-amine,
N-(4-bromophenyl)-4-(2,6-dimethylimidazo[1,2-a]pyridin-3-yl)-1,3-thiazol-2-amine,
N-(4-chlorophenyl)-4-(2,6-dimethylimidazo[1,2-a]pyridin-3-yl)-1,3-thiazol-2-amine,
4-(imidazo[1,2-a]pyridin-3-yl)-N-(4-iodophenyl)-1,3-thiazol-2-amine,
N-(4-bromophenyl)-N-methyl-4-(2-methylimidazo[1,2-a]pyrimidin-3-yl)-1,3-thiazol-2-amine,
N'-[4-(6-bromo-2-methylimidazo[1,2-a]pyridin-3-yl)-1,3-thiazol-2-yl]-N,N-dimethylbenzene-1,4-diamine,
N-(1,3-benzodioxol-5-yl)-4-(6-bromo-2-methylimidazo[1,2-a]pyridin-3-yl)-1,3-thiazol-2-amine,
4-(imidazo[1,2-a]pyrimidin-3-yl)-N-(4-iodophenyl)-1,3-thiazol-2-amine,
N-(3,4-dimethoxyphenyl)-4-(2-methylimidazo[1,2-a]pyrimidin-3-yl)-1,3-thiazol-2-amine,
4-(2-methylimidazo[1,2-a]pyrimidin-3-yl)-N-(4-methylphenyl)-1,3-thiazol-2-amine,
N-(4-ethylphenyl)-4-(2-methylimidazo[1,2-a]pyrimidin-3-yl)-1,3-thiazol-2-amine,
4-(2-methylimidazo[1,2-a]pyrimidin-3-yl)-N-[4-(propan-2-yl)phenyl]-1,3-thiazol-2-amine,
4-(6-chloro-2-methylimidazo[1,2-a]pyridin-3-yl)-N-(4-ethoxyphenyl)-1,3-thiazol-2-amine,
4-(6-chloro-2-methylimidazo[1,2-a]pyridin-3-yl)-N-(4-methylphenyl)-1,3-thiazol-2-amine,
4-(6-chloro-2-methylimidazo[1,2-a]pyridin-3-yl)-N-(4-ethylphenyl)-1,3-thiazol-2-amine,
4-(6-chloro-2-methylimidazo[1,2-a]pyridin-3-yl)-N-[4-(propan-2-yl)phenyl]-1,3-thiazol-2-amine,
4-{[4-(6-chloro-2-methylimidazo[1,2-a]pyridin-3-yl)-1,3-thiazol-2-yl]amino}phenol,
4-(6-chloro-2-methylimidazo[1,2-a]pyridin-3-yl)-N-[4-(2-methoxyethoxy)phenyl]-1,3-thiazol-2-amine,
3-[2-(1,3-benzodioxol-5-ylamino)-1,3-thiazol-4-yl]-2-methylimidazo[1,2-a]pyridin-8-ol,
N-(3-chloro-4-methoxyphenyl)-4-(6-chloro-2-methylimidazo[1,2-a]pyridin-3-yl)-1,3-thiazol-2-amine,
4-(6-chloro-2-methylimidazo[1,2-a]pyridin-3-yl)-N-(3-fluoro-4-methoxyphenyl)-1,3-thiazol-2-amine,
N-(4-{[4-(6-chloro-2-methylimidazo[1,2-a]pyridin-3-yl)-1,3-thiazol-2-yl]amino}phenyl)acetamide,
4-(6-chloro-2-methylimidazo[1,2-a]pyridin-3-yl)-N-(2,6-dichlorophenyl)-1,3-thiazol-2-amine,
1-(4-{[4-(6-bromo-2-methylimidazo[1,2-a]pyridin-3-yl)-1,3-thiazol-2-yl]amino}phenyl)ethanone,
4-(6-bromo-2-methylimidazo[1,2-a]pyridin-3-yl)-N-(4-chlorophenyl)-1,3-thiazol-2-amine,
4-(6-bromo-2-methylimidazo[1,2-a]pyridin-3-yl)-N-(4-iodophenyl)-1,3-thiazol-2-amine, 4-(6-bromo-2-methylimidazo[1,2-a]pyridin-3-yl)-N-(4-bromophenyl)-1,3-thiazol-2-amine,
4-(6-bromo-2-methylimidazo[1,2-a]pyridin-3-yl)-N-(3-chloro-4-methoxyphenyl)-1,3-thiazol-2-amine,
4-(6-bromo-2-methylimidazo[1,2-a]pyridin-3-yl)-N-(3-fluoro-4-methoxyphenyl)-1,3-thiazol-2-amine,
4-(6-chloroimidazo[1,2-a]pyridin-3-yl)-N-(4-methoxyphenyl)-1,3-thiazol-2-amine,
N'-[4-(6-chloroimidazo[1,2-a]pyridin-3-yl)-1,3-thiazol-2-yl]-N,N-dimethylbenzene-1,4-diamine,
1-(4-{[4-(6-chloroimidazo[1,2-a]pyridin-3-yl)-1,3-thiazol-2-yl]amino}phenyl)ethanone,
4-(6-chloroimidazo[1,2-a]pyridin-3-yl)-N-(4-iodophenyl)-1,3-thiazol-2-amine,
4-(6-chloroimidazo[1,2-a]pyridin-3-yl)-N-(3-chloro-4-methoxyphenyl)-1,3-thiazol-2-amine,
4-(6-chloroimidazo[1,2-a]pyridin-3-yl)-N-(3-fluoro-4-methoxyphenyl)-1,3-thiazol-2-amine,
4-(6-chloro-2-methylimidazo[1,2-a]pyridin-3-yl)-N-(3,4-dichlorophenyl)-1,3-thiazol-2-amine,
N-(4-tert-butylphenyl)-4-(6-chloro-2-methylimidazo[1,2-a]pyridin-3-yl)-1,3-thiazol-2-amine,
N-(4-chlorophenyl)-4-(2-methylimidazo[1,2-a]pyridin-3-yl)pyrimidin-2-amine,
N-(4-bromophenyl)-4-(2-methylimidazo[1,2-a]pyridin-3-yl)pyrimidin-2-amine,
N-(4-methoxyphenyl)-4-(2-methylimidazo[1,2-a]pyridin-3-yl)pyrimidin-2-amine,
N-(4-ethoxyphenyl)-4-(2-methylimidazo[1,2-a]pyrimidin-3-yl)pyrimidin-2-amine,
1-(4-{[4-(2-methylimidazo[1,2-a]pyridin-3-yl)pyrimidin-2-yl]amino}phenyl)ethanone,
N,N-dimethyl-N'-[4-(2-methylimidazo[1,2-a]pyridin-3-yl)pyrimidin-2-yl]benzene-1,3-diamine,
N-(4-iodophenyl)-4-(2-methylimidazo[1,2-a]pyridin-3-yl)pyrimidin-2-amine,
N-(4-iodophenyl)-4-(2-methylimidazo[1,2-a]pyridin-3-yl)pyrimidin-2-amine,
N-(4-bromophenyl)-5-methyl-4-(2-methylimidazo[1,2-a]pyrimidin-3-yl)-1,3-thiazol-2-amine,
N-(4-iodophenyl)-5-methyl-4-(2-methylimidazo[1,2-a]pyrimidin-3-yl)-1,3-thiazol-2-amine,
N-(1,3-benzodioxol-5-yl)-4-(2-methylimidazo[1,2-a]pyridin-3-yl)pyrimidin-2-amine,
N-(1,3-benzodioxol-5-yl)-4-(2-methylimidazo[1,2-a]pyrimidin-3-yl)pyrimidin-2-amine,
N-(4-iodophenyl)-N-methyl-4-(2-methylimidazo[1,2-a]pyrimidin-3-yl)pyrimidin-2-amine,
N-(4-bromophenyl)-4-(2-methylimidazo[1,2-a]pyrimidin-3-yl)pyrimidin-2-amine,
N-(3-bromophenyl)-4-(2-methylimidazo[1,2-a]pyridin-3-yl)pyrimidin-2-amine,
N-(4-ethoxyphenyl)-4-(2-methylimidazo[1,2-a]pyridin-3-yl)pyrimidin-2-amine,
N,N-dimethyl-N'-[4-(2-methylimidazo[1,2-a]pyridin-3-yl)pyrimidin-2-yl]benzene-1,4-diamine,
N,N-diethyl-N'-[4-(2-methylimidazo[1,2-a]pyridin-3-yl)pyrimidin-2-yl]benzene-1,4-diamine,
1-(4-{[4-(2-methylimidazo[1,2-a]pyrimidin-3-yl)pyrimidin-2-yl]amino}phenyl)ethanone,
N-(4-bromo-2-chlorophenyl)-4-(6-chloro-2-methylimidazo[1,2-a]pyridin-3-yl)-1,3-thiazol-2-amine,
4-(6-chloro-2-methylimidazo[1,2-a]pyridin-3-yl)-N-phenyl-1,3-thiazol-2-amine,
4-(6-chloroimidazo[1,2-a]pyridin-3-yl)-N-[2,6-dibromo-4-(2-methoxyethoxy)phenyl]-1,3-thiazol-2-amine,
4-(6-chloroimidazo[1,2-a]pyridin-3-yl)-N-(2,4,6-tribromophenyl)-1,3-thiazol-2-amine,
4-(6-chloroimidazo[1,2-a]pyridin-3-yl)-N-(2,4,6-trichlorophenyl)-1,3-thiazol-2-amine,
N,N,N'-trimethyl-N'-[4-(2-methylimidazo[1,2-a]pyridin-3-yl)pyrimidin-2-yl]benzene-1,4-diamine,
N,N-diethyl-N'-methyl-N'-[4-(2-methylimidazo[1,2-a]pyridin-3-yl)pyrimidin-2-yl]benzene-1,4-diamine,
N-(1,3-benzodioxol-5-yl)-N-methyl-4-(2-methylimidazo[1,2-a]pyridin-3-yl)pyrimidin-2-amine,
N-(2-chlorophenyl)-N-methyl-4-(2-methylimidazo[1,2-a]pyridin-3-yl)pyrimidin-2-amine,
N-(4-methoxy-2,6-dimethylphenyl)-4-(2-methylimidazo[1,2-a]pyridin-3-yl)pyrimidin-2-amine,
N-(4-ethoxyphenyl)-N-methyl-4-(2-methylimidazo[1,2-a]pyridin-3-yl)pyrimidin-2-amine,
N-(4-iodophenyl)-N-methyl-4-(2-methylimidazo[1,2-a]pyridin-3-yl)pyrimidin-2-amine,
4-(2-ethylimidazo[1,2-a]pyrimidin-3-yl)-N-(4-methoxyphenyl)-1,3-thiazol-2-amine,
N'-[4-(2-ethylimidazo[1,2-a]pyridin-3-yl)-1,3-thiazol-2-yl]-N,N-dimethylbenzene-1,4-diamine,
N-(2,6-dibromo-4-methoxyphenyl)-4-(2-ethylimidazo[1,2-a]pyridin-3-yl)-1,3-thiazol-2-amine,
N-(4-chlorophenyl)-4-(2-ethylimidazo[1,2-a]pyridin-3-yl)-1,3-thiazol-2-amine,
N-(4-bromophenyl)-4-(2-ethylimidazo[1,2-a]pyridin-3-yl)-1,3-thiazol-2-amine,
4-(2-ethylimidazo[1,2-a]pyridin-3-yl)-N-(4-iodophenyl)-1,3-thiazol-2-amine,
1-(4-{[4-(2-ethylimidazo[1,2-a]pyridin-3-yl)-1,3-thiazol-2-yl]amino}phenyl)ethanone,
N-(1,3-benzodioxol-5-yl)-4-(2-ethylimidazo[1,2-a]pyrimidin-3-yl)-1,3-thiazol-2-amine,
4-(2-ethylimidazo[1,2-a]pyrimidin-3-yl)-N-(3-fluoro-4-methoxyphenyl)-1,3-thiazol-2-amine,
N-(3-chloro-4-methoxyphenyl)-4-(2-ethylimidazo[1,2-a]pyrimidin-3-yl)-1,3-thiazol-2-amine,
N-(1,3-benzodioxol-5-yl)-4-[2-(trifluoromethyl)imidazo[1,2-a]pyridin-3-yl]-1,3-thiazol-2-amine,
N-(3-fluoro-4-methoxyphenyl)-4-(6-fluoro-2-methylimidazo[1,2-a]pyridin-3-yl)-1,3-thiazol-2-amine,
4-(6-fluoro-2-methylimidazo[1,2-a]pyridine-3-yl)-N-(4-iodophenyl)-1,3-thiazol-2-amine,
N'-[4-(6-fluoro-2-methylimidazo[1,2-a]pyridin-3-yl)-1,3-thiazol-2-yl]-N,N-dimethylbenzene-1,4-diamine,
N-(1,3-benzodioxol-5-yl)-4-(6-fluoro-2-methylimidazo[1,2-a]pyridin-3-yl)-1,3-thiazol-2-amine,
1-(4-{[4-(6-fluoro-2-methylimidazo[1,2-a]pyridin-3-yl)-1,3-thiazol-2-yl]amino}phenyl)ethanone,
4-(6-fluoro-2-methylimidazo[1,2-a]pyridin-3-yl)-N-(4-methoxyphenyl)-1,3-thiazol-2-amine,
N-(4-chlorophenyl)-4-(6-fluoro-2-methylimidazo[1,2-a]pyridin-3-yl)-1,3-thiazol-2-amine,
N-(4-bromophenyl)-4-(6-fluoro-2-methylimidazo[1,2-a]pyridin-3-yl)-1,3-thiazol-2-amine,
N-(4-ethoxyphenyl)-4-(6-fluoro-2-methylimidazo[1,2-a]pyridin-3-yl)-1,3-thiazol-2-amine,
N-(4-tert-butylphenyl)-4-(6-fluoro-2-methylimidazo[1,2-a]pyridin-3-yl)-1,3-thiazol-2-amine,
N-(4-bromo-2-chlorophenyl)-4-(6-fluoro-2-methylimidazo[1,2-a]pyridin-3-yl)-1,3-thiazol-2-amine,
N-(2-fluorophenyl)-4-(imidazo[1,2-a]pyridin-3-yl)pyrimidin-2-amine,
1-(4-{methyl[4-(2-methylimidazo[1,2-a]pyridin-3-yl)pyrimidin-2-yl]amino}phenyl)ethanone, 4-(2-methylimidazo[1,2-a]pyrimidin-3-yl)-N-(4-methylphenyl)pyrimidin-2-amine,
4-(2-methylimidazo[1,2-a]pyridin-3-yl)-N-(4-methylphenyl)pyrimidin-2-amine,
N-methyl-4-(2-methylimidazo[1,2-a]pyrimidin-3-yl)-N-(4-methylphenyl)pyrimidin-2-amine,
N-(3-fluoro-4-methoxyphenyl)-4-(2-propylimidazo[1,2-a]pyridin-3-yl)-1,3-thiazol-2-amine,
N-(3-chloro-4-methoxyphenyl)-4-(2-propylimidazo[1,2-a]pyridin-3-yl)-1,3-thiazol-2-amine,
N-(4-ethoxyphenyl)-4-(2-propylimidazo[1,2-a]pyridin-3-yl)-1,3-thiazol-2-amine,
N-(4-iodophenyl)-4-(2-propylimidazo[1,2-a]pyridin-3-yl)-1,3-thiazol-2-amine,
N-(1,3-benzodioxol-5-yl)-4-(2-propylimidazo[1,2-a]pyridin-3-yl)-1,3-thiazol-2-amine,
N,N-dimethyl-N'-[4-(2-propylimidazo[1,2-a]pyridin-3-yl)-1,3-thiazol-2-yl]benzene-1,4-diamine,
1-(4-{[4-(2-propylimidazo[1,2-a]pyridin-3-yl)-1,3-thiazol-2-yl]amino}phenyl)ethanone,
N-(4-chlorophenyl)-4-(2-propylimidazo[1,2-a]pyridin-3-yl)-1,3-thiazol-2-amine,
N-(4-bromophenyl)-4-(2-propylimidazo[1,2-a]pyridin-3-yl)-1,3-thiazol-2-amine,
N-(4-methoxyphenyl)-4-(2-propylimidazo[1,2-a]pyridin-3-yl)-1,3-thiazol-2-amine,
N-(3-fluoro-4-methoxyphenyl)-4-(2-propylimidazo[1,2-a]pyrimidin-3-yl)-1,3-thiazol-2-amine,
N-(1,3-benzodioxol-5-yl)-4-(2-propylimidazo[1,2-a]pyrimidin-3-yl)-1,3-thiazol-2-amine,
N,N-dimethyl-N'-[4-(2-propylimidazo[1,2-a]pyrimidin-3-yl)-1,3-thiazol-2-yl]benzene-1,4-diamine,
N-(4-bromophenyl)-4-(2-propylimidazo[1,2-a]pyrimidin-3-yl)-1,3-thiazol-2-amine,
N-(4-iodophenyl)-4-(2-propylimidazo[1,2-a]pyrimidin-3-yl)-1,3-thiazol-2-amine,
N-(4-methoxyphenyl)-4-(2-propylimidazo[1,2-a]pyrimidin-3-yl)-1,3-thiazol-2-amine,
N-phenyl-4-(2-propylimidazo[1,2-a]pyrimidin-3-yl)-1,3-thiazol-2-amine,
N-(3-methoxyphenyl)-4-(2-methylimidazo[1,2-a]pyridin-3-yl)-1,3-thiazol-2-amine,
N-methyl-4-(2-methylimidazo[1,2-a]pyridin-3-yl)-N-(4-methylphenyl)pyrimidin-2-amine,
3-{[4-(2-methylimidazo[1,2-a]pyridin-3-yl)pyrimidin-2-yl]amino}phenol,
4-(2-methylimidazo[1,2-a]pyridin-3-yl)-N-(4-methylphenyl)-1,3-thiazol-2-amine,
N-(4-ethylphenyl)-4-(2-methylimidazo[1,2-a]pyridin-3-yl)-1,3-thiazol-2-amine,
N,N-diethyl-N'-[4-(2-methylimidazo[1,2-a]pyridin-3-yl)-1,3-thiazol-2-yl]benzene-1,4-diamine,
N-(4-{[4-(2-methylimidazo[1,2-a]pyridin-3-yl)-1,3-thiazol-2-yl]amino}phenyl)acetamide,
N-(1,3-benzodioxol-5-yl)-4-[2-(trifluoromethyl)imidazo[1,2-a]pyridin-3-yl]-1,3-thiazol-2-amine,
4-{[4-(2-methylimidazo[1,2-a]pyridin-3-yl)pyrimidin-2-yl]amino}benzoic acid,
N-(4-bromophenyl)-4-(2-methylimidazo[1,2-a]pyridin-3-yl)-1,3-thiazol-2-amine,
N-(3,4-dichlorophenyl)-4-(2-methylimidazo[1,2-a]pyridin-3-yl)-1,3-thiazol-2-amine,
N-(4-chlorophenyl)-4-(2-methylimidazo[1,2-a]pyridin-3-yl)-1,3-thiazol-2-amine,
N-(4-bromo-2-chlorophenyl)-4-(2-methylimidazo[1,2-a]pyridin-3-yl)-1,3-thiazol-2-amine,
4-{[4-(2-methylimidazo[1,2-a]pyridin-3-yl)-1,3-thiazol-2-yl]amino}benzene-1,2-diol,
N-(3,4-dimethoxyphenyl)-4-(2-methylimidazo[1,2-a]pyridin-3-yl)-1,3-thiazol-2-amine,
N-(2,4-difluorophenyl)-4-(2-methylimidazo[1,2-a]pyridin-3-yl)-1,3-thiazol-2-amine,
N-(4-ethoxyphenyl)-4-(2-methylimidazo[1,2-a]pyridin-3-yl)-1,3-thiazol-2-amine,
N-(2-bromo-4-methylphenyl)-4-(6-chloro-2-methylimidazo[1,2-a]pyridin-3-yl)-1,3-thiazol-2-amine,
N'-[4-(6-chloro-2-methylimidazo[1,2-a]pyridin-3-yl)-1,3-thiazol-2-yl]-N,N-diethylbenzene-1,4-diamine,
4-(6-chloro-2-methylimidazo[1,2-a]pyridin-3-yl)-N-(3,4-dimethoxyphenyl)-1,3-thiazol-2-amine,
N-(2-bromo-4-methoxyphenyl)-4-(6-chloro-2-methylimidazo[1,2-a]pyridin-3-yl)-1,3-thiazol-2-amine,
4-(6-chloro-2-methylimidazo[1,2-a]pyridin-3-yl)-N-(3-methylphenyl)-1,3-thiazol-2-amine,
3-{[4-(6-chloro-2-methylimidazo[1,2-a]pyridin-3-yl)-1,3-thiazol-2-yl]amino}phenol,
1-(3-{[4-(6-chloro-2-methylimidazo[1,2-a]pyridin-3-yl)-1,3-thiazol-2-yl]amino}phenyl)ethanone,
N-(3-bromophenyl)-4-(6-chloro-2-methylimidazo[1,2-a]pyridin-3-yl)-1,3-thiazol-2-amine,
4-(6-chloro-2-methylimidazo[1,2-a]pyridin-3-yl)-N-(3-chlorophenyl)-1,3-thiazol-2-amine,
4-(6-chloro-2-methylimidazo[1,2-a]pyridin-3-yl)-N-(2,4-dimethylphenyl)-1,3-thiazol-2-amine,
4-(6-chloro-2-methylimidazo[1,2-a]pyridin-3-yl)-N-(3-fluorophenyl)-1,3-thiazol-2-amine,
N-(4-bromo-2-methylphenyl)-4-(6-chloro-2-methylimidazo[1,2-a]pyridin-3-yl)-1,3-thiazol-2-amine,
4-(6-chloro-2-methylimidazo[1,2-a]pyridin-3-yl)-N-(3-methoxyphenyl)-1,3-thiazol-2-amine,
4-(6-chloro-2-methylimidazo[1,2-a]pyridin-3-yl)-N-(2,4-dichlorophenyl)-1,3-thiazol-2-amine,
4-(6-chloro-2-methylimidazo[1,2-a]pyridin-3-yl)-N-(2,2-dimethyl-1,3-benzodioxol-5-yl)-1,3-thiazol-2-amine,
N-(1,3-benzodioxol-5-yl)-4-(6,8-dichloro-2-methylimidazo[1,2-a]pyridin-3-yl)-1,3-thiazol-2-amine,
N'-[4-(2,8-dimethylimidazo[1,2-a]pyridin-3-yl)-1,3-thiazol-2-yl]-N,N-dimethylbenzene-1,4-diamine,
4-(2,8-dimethylimidazo[1,2-a]pyridin-3-yl)-N-(4-methoxyphenyl)-1,3-thiazol-2-amine,
4-(2,8-dimethylimidazo[1,2-a]pyridin-3-yl)-N-(4-methylphenyl)-1,3-thiazol-2-amine,
N-(4-chlorophenyl)-4-(2,8-dimethylimidazo[1,2-a]pyridin-3-yl)-1,3-thiazol-2-amine,
4-(2,8-dimethylimidazo[1,2-a]pyridin-3-yl)-N-(3-methoxyphenyl)-1,3-thiazol-2-amine,
N-(1,3-benzodioxol-5-yl)-4-(2,8-dimethylimidazo[1,2-a]pyridin-3-yl)-1,3-thiazol-2-amine,
N'-[4-(8-bromo-2-methylimidazo[1,2-a]pyridin-3-yl)-1,3-thiazol-2-yl]-N,N-dimethylbenzene-1,4-diamine,
4-(8-bromo-2-methylimidazo[1,2-a]pyridin-3-yl)-N-(4-methoxyphenyl)-1,3-thiazol-2-amine,
4-(8-bromo-2-methylimidazo[1,2-a]pyridin-3-yl)-N-(4-methylphenyl)-1,3-thiazol-2-amine,
4-(8-bromo-2-methylimidazo[1,2-a]pyridin-3-yl)-N-(4-chlorophenyl)-1,3-thiazol-2-amine,
4-(8-bromo-2-methylimidazo[1,2-a]pyridin-3-yl)-N-phenyl-1,3-thiazol-2-amine,
4-(8-bromo-2-methylimidazo[1,2-a]pyridin-3-yl)-N-(3-methoxyphenyl)-1,3-thiazol-2-amine,
4-(8-bromo-2-methylimidazo[1,2-a]pyridin-3-yl)-N-(2-chlorophenyl)-1,3-thiazol-2-amine, 4-(8-bromo-2-methylimidazo[1,2-a]pyridin-3-yl)-N-(2-methoxyphenyl)-1,3-thiazol-2-amine,
N-(1,3-benzodioxol-5-yl)-4-(8-bromo-2-methylimidazo[1,2-a]pyridin-3-yl)-1,3-thiazol-2-amine,
4-(6-fluoro-2-methylimidazo[1,2-a]pyridin-3-yl)-N-(3-methoxyphenyl)-1,3-thiazol-2-amine,
4-(6-fluoro-2-methylimidazo[1,2-a]pyridin-3-yl)-N-(4-methylphenyl)-1,3-thiazol-2-amine,
1-(3-{[4-(6-fluoro-2-methylimidazo[1,2-a]pyridin-3-yl)-1,3-thiazol-2-yl]amino}phenyl)ethanone,
N-(2,6-dibromophenyl)-4-(6-fluoro-2-methylimidazo[1,2-a]pyridin-3-yl)-1,3-thiazol-2-amine,
4-(7-chloro-2-methylimidazo[1,2-a]pyridin-3-yl)-N-(4-chlorophenyl)-1,3-thiazol-2-amine,
4-(7-chloro-2-methylimidazo[1,2-a]pyridin-3-yl)-N-(4-methoxyphenyl)-1,3-thiazol-2-amine,
N'-[4-(7-chloro-2-methylimidazo[1,2-a]pyridin-3-yl)-1,3-thiazol-2-yl]-N,N-dimethylbenzene-1,4-diamine,
4-(7-chloro-2-methylimidazo[1,2-a]pyridin-3-yl)-N-(4-methylphenyl)-1,3-thiazol-2-amine,
1-(4-{[4-(7-chloro-2-methylimidazo[1,2-a]pyridin-3-yl)-1,3-thiazol-2-yl]amino}phenyl)ethanone,
4-(imidazo[1,2-a]pyridin-3-yl)-N-(4-methoxyphenyl)pyrimidin-2-amine,
N-(3-chlorophenyl)-4-(imidazo[1,2-a]pyridin-3-yl)pyrimidin-2-amine,
N-(2-chlorophenyl)-4-(imidazo[1,2-a]pyridin-3-yl)pyrimidin-2-amine,
N-(4-fluorophenyl)-4-(imidazo[1,2-a]pyridin-3-yl)pyrimidin-2-amine,
N-(2,6-dibromo-4-methoxyphenyl)-4-(imidazo[1,2-a]pyridin-3-yl)pyrimidin-2-amine,
1-(4-{[4-(imidazo[1,2-a]pyridin-3-yl)pyrimidin-2-yl]amino}phenyl)ethanone,
N-(1,3-benzodioxol-5-yl)-4-(imidazo[1,2-a]pyridin-3-yl)pyrimidin-2-amine,
N-(4-ethoxyphenyl)-4-(imidazo[1,2-a]pyridin-3-yl)pyrimidin-2-amine,
N,N-diethyl-N'-[4-(imidazo[1,2-a]pyridin-3-yl)pyrimidin-2-yl]benzene-1,4-diamine,
N'-[4-(imidazo[1,2-a]pyridin-3-yl)pyrimidin-2-yl]-N,N-dimethylbenzene-1,4-diamine,
N-(3-fluorophenyl)-4-(imidazo[1,2-a]pyridin-3-yl)pyrimidin-2-amine,
N-(3-bromophenyl)-4-(imidazo[1,2-a]pyridin-3-yl)pyrimidin-2-amine,
N-(2,6-dibromo-4-methoxyphenyl)-4-(imidazo[1,2-a]pyrimidin-3-yl)pyrimidin-2-amine,
1-(4-{[4-(imidazo[1,2-a]pyrimidin-3-yl)pyrimidin-2-yl]amino}phenyl)ethanone,
N-(1,3-benzodioxol-5-yl)-4-(imidazo[1,2-a]pyrimidin-3-yl)pyrimidin-2-amine,
4-(imidazo[1,2-a]pyrimidin-3-yl)-N-(3-methoxyphenyl)pyrimidin-2-amine,
4-(imidazo[1,2-a]pyrimidin-3-yl)-N-(4-methoxyphenyl)pyrimidin-2-amine,
N-(4-ethoxyphenyl)-4-(imidazo[1,2-a]pyrimidin-3-yl)pyrimidin-2-amine,
N,N-diethyl-N'-[4-(imidazo[1,2-a]pyrimidin-3-yl)pyrimidin-2-yl]benzene-1,4-diamine,
N'-[4-(imidazo[1,2-a]pyrimidin-3-yl)pyrimidin-2-yl]-N,N-dimethylbenzene-1,3-diamine,
N'-[4-(imidazo[1,2-a]pyrimidin-3-yl)pyrimidin-2-yl]-N,N-dimethylbenzene-1,4-diamine,
N-(2-fluorophenyl)-4-(imidazo[1,2-a]pyrimidin-3-yl)pyrimidin-2-amine,
N-(3-fluorophenyl)-4-(imidazo[1,2-a]pyrimidin-3-yl)pyrimidin-2-amine,
N-(4-fluorophenyl)-4-(imidazo[1,2-a]pyrimidin-3-yl)pyrimidin-2-amine,
N-(3-chlorophenyl)-4-(imidazo[1,2-a]pyrimidin-3-yl)pyrimidin-2-amine,
N-(4-bromophenyl)-4-(imidazo[1,2-a]pyrimidin-3-yl)pyrimidin-2-amine, and
N-(4-bromophenyl)-4-(2-ethylimidazo[1,2-a]pyrimidin-3-yl)pyrimidin-2-amine.

6. A method for inhibiting Bmi-1 expression in a subject in need thereof comprising administering an effective amount of a compound of Formula (I) or a free acid, free base, salt, ester, hydrate, solvate, chelate, clathrate, isotopologue, geometric isomer, stereoisomer, racemate, enantiomer, diastereomer or tautomer thereof to the subject:

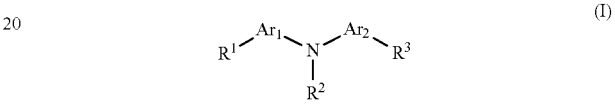

wherein,
$Ar_1$ is phenyl or benzo[1,3]dioxolyl;
$Ar_2$ is thiazolyl or pyrimidinyl substituted with $R^4$;
$R^1$ is hydrogen or one, two, three or four substituents each selected from halogen, cyano, hydroxy, $C_{1-8}$alkyl, $C_{2-8}$alkenyl, $C_{2-8}$alkynyl, $C_{1-8}$alkoxy, halo-$C_{1-8}$alkyl, halo-$C_{1-8}$alkoxy, hydroxy-$C_{1-8}$alkyl, $C_{1-8}$alkoxy-$C_{1-8}$alkyl, $C_{1-8}$alkoxy-$C_{1-8}$alkoxy, $C_{1-8}$alkoxy-$C_{1-8}$alkoxy-$C_{1-8}$alkoxy, carboxy, amino, $C_{1-8}$alkyl-amino, amino-$C_{1-8}$alkyl, $C_{1-8}$alkyl-amino-$C_{1-8}$alkyl, $C_{1-8}$alkyl-carbonyl, $C_{1-8}$alkoxy-carbonyl, aminosulfonyl, $C_{1-8}$alkyl-aminosulfonyl, $C_{1-8}$alkyl-carbonyl-amino and $C_{1-8}$alkoxy-carbonyl-amino;
$R^2$ is hydrogen or $C_{1-8}$alkyl;
$R^3$ is imidazo[1,2-a]pyridin-3-yl or imidazo[1,2-a]pyrimidin-3-yl each substituted with $R^5$ and $R^6$;
$R^4$ and $R^5$ are each hydrogen, $C_{1-8}$alkyl or halo-$C_{1-8}$alkyl; and
$R^6$ is hydrogen or one, two, three or four substituents each selected from halogen, hydroxy or $C_{1-8}$alkyl.

7. The method of claim 6, further comprising contacting a cancer cell having elevated Bmi-1 expression or a cancer stem cell having elevated Bmi-1 expression from the subject with an amount of the compound or a form thereof, determining an effective amount of the compound or a form thereof that inhibits Bmi-1 expression in the cell and subsequently administering the effective amount of the compound or a form thereof to the subject.

8. A method for inhibiting Bmi-1 expression in a subject in need thereof comprising administering an effective amount of a compound of claim 5 or a form thereof to the subject.

9. The method of claim 8, further comprising contacting a cancer cell having elevated Bmi-1 expression or a cancer stem cell having elevated Bmi-1 expression from the subject with an amount of the compound or a form thereof, determining an effective amount of the compound or a form thereof that inhibits Bmi-1 expression in the cell and subsequently administering the effective amount of the compound or a form thereof to the subject.

10. The method of either of claim 7 or claim 9, wherein the effective amount of the compound or a form thereof determined to inhibit Bmi-1 expression in the contacted cell blocks the $G_2/M$ phase of the cell cycle in the contacted cell.

11. The method of claim 10, wherein the effective amount of the compound or a form thereof is in a range of from about 0.001 mg/Kg/day to about 500 mg/Kg/day.

12. The method of claim 6, further comprising administering a compound of claim 1 or a form thereof in combination with one or more additional agents and optionally with radiation therapy.

13. A pharmaceutical composition comprising an effective amount of a compound of claim 1 or a form thereof in admixture with a pharmaceutically acceptable excipient.

14. The method of claim 12, wherein the one or more additional agents are an anti-cancer agent, anti-proliferative agent, immunomodulatory agent, anti-angiogenic agent, anti-inflammatory agent, pain reliever, β2-agonist, anticholinergic agent, antihistamine, anti-malarial agent, anti-viral agent or an antibiotic.

15. The method of claim 12, wherein the one or more additional agents are leukotreine antagonist, sulphasalazine or penicillamine.

16. The method of claim 12, wherein the one or more additional agents is dapsone.

* * * * *